United States Patent
Rajasekaran et al.

(10) Patent No.: US 10,799,845 B2
(45) Date of Patent: Oct. 13, 2020

(54) SUBSTRATES, SYSTEMS, AND METHODS FOR ARRAY SYNTHESIS AND BIOMOLECULAR ANALYSIS

(71) Applicant: Vibrant Holdings, LLC, San Carlos, CA (US)

(72) Inventors: John J. Rajasekaran, Hillsborough, CA (US); Vasanth Jayaraman, San Mateo, CA (US); Tianhao Wang, San Mateo, CA (US); Kang Bei, San Mateo, CA (US); Hari Krishnan Krishnamurthy, San Mateo, CA (US); Punitha Vedantham, San Carlos, CA (US)

(73) Assignee: Vibrant Holdings, LLC, San Carlos, CA (US)

( * ) Notice: Subject to any disclaimer, the term of this patent is extended or adjusted under 35 U.S.C. 154(b) by 0 days.

(21) Appl. No.: 16/287,968

(22) Filed: Feb. 27, 2019

(65) Prior Publication Data
US 2019/0366291 A1    Dec. 5, 2019

Related U.S. Application Data

(63) Continuation of application No. 14/442,389, filed as application No. PCT/US2013/070207 on Nov. 14, (Continued)

(51) Int. Cl.
| | |
|---|---|
| *B01J 19/00* | (2006.01) |
| *G01N 33/68* | (2006.01) |
| *C40B 50/18* | (2006.01) |

(52) U.S. Cl.
CPC ........... *B01J 19/0046* (2013.01); *C40B 50/18* (2013.01); *G01N 33/6842* (2013.01); (Continued)

(58) Field of Classification Search
CPC combination set(s) only.
See application file for complete search history.

(56) References Cited

U.S. PATENT DOCUMENTS

| | | | |
|---|---|---|---|
| 5,069,996 | A | 12/1991 | Rogler |
| 5,143,854 | A | 9/1992 | Pirrung et al. |
| | | (Continued) | |

FOREIGN PATENT DOCUMENTS

| | | |
|---|---|---|
| CN | 103675291 A | 3/2014 |
| JP | H05-294995 A | 11/1993 |
| | (Continued) | |

OTHER PUBLICATIONS

Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.
(Continued)

*Primary Examiner* — Jeremy C Flinders
(74) *Attorney, Agent, or Firm* — Goodwin Procter LLP

(57) ABSTRACT

Disclosed herein are formulations, substrates, and arrays. In certain embodiments, substrates and arrays comprise a porous layer for synthesis and attachment of polymers or biomolecules. Also disclosed herein are methods for manufacturing and using the formulations, substrates, and arrays, including porous arrays. Also disclosed herein are formulations and methods for one-step coupling, e.g., for synthesis of peptides in an N→C orientation. In some embodiments, disclosed herein are formulations and methods for high efficiency coupling of biomolecules to a substrate.

10 Claims, 12 Drawing Sheets

Specification includes a Sequence Listing.

Related U.S. Application Data 2013, now Pat. No. 10,286,376, which is a continuation-in-part of application No. PCT/US2013/062773, filed on Sep. 30, 2013, which is a continuation-in-part of application No. PCT/US2013/025190, filed on Feb. 7, 2013.

(60) Provisional application No. 61/726,515, filed on Nov. 14, 2012, provisional application No. 61/732,221, filed on Nov. 30, 2012, provisional application No. 61/765,584, filed on Feb. 15, 2013, provisional application No. 61/805,884, filed on Mar. 27, 2013, provisional application No. 61/866,512, filed on Aug. 15, 2013, provisional application No. 61/761,347, filed on Feb. 6, 2013.

(52) U.S. Cl.
CPC ............. *B01J 2219/00596* (2013.01); *B01J 2219/00637* (2013.01); *B01J 2219/00711* (2013.01); *B01J 2219/00725* (2013.01)

(56) References Cited

U.S. PATENT DOCUMENTS

| | | | |
|---|---|---|---|
| 5,240,811 | A | 8/1993 | Taylor et al. |
| 5,310,687 | A | 5/1994 | Bard et al. |
| 5,866,434 | A | 2/1999 | Massey et al. |
| 5,919,523 | A | 7/1999 | Sundberg et al. |
| 6,017,696 | A | 1/2000 | Heller |
| 6,040,138 | A | 3/2000 | Lockhart et al. |
| 6,083,697 | A | 7/2000 | Beecher et al. |
| 6,140,045 | A | 10/2000 | Wohlstadter et al. |
| 6,319,726 | B1 | 11/2001 | Schuppan et al. |
| 6,506,558 | B1 | 1/2003 | Fodor et al. |
| 6,521,181 | B1 | 2/2003 | Northrup et al. |
| 6,943,034 | B1 | 9/2005 | Winkler et al. |
| 7,510,841 | B2 | 3/2009 | Stuelpnagel et al. |
| 7,544,638 | B2 | 6/2009 | Gao et al. |
| 8,128,908 | B2 | 3/2012 | Santra et al. |
| 9,216,399 | B2 | 12/2015 | Rajasekaran et al. |
| 9,417,236 | B2 | 8/2016 | Rajasekaran et al. |
| 10,006,909 | B2 | 6/2018 | Rajasekaran et al. |
| 10,040,818 | B2 | 8/2018 | Rajasekaran et al. |
| 2002/0076834 | A1 | 6/2002 | Detlef et al. |
| 2002/0086319 | A1 | 7/2002 | Ellson et al. |
| 2003/0068446 | A1 | 4/2003 | Mirkin et al. |
| 2003/0082294 | A1 | 5/2003 | Bruhn et al. |
| 2003/0124029 | A1 | 7/2003 | Webb et al. |
| 2003/0148401 | A1 | 8/2003 | Agrawal et al. |
| 2003/0228605 | A1 | 12/2003 | Sloostra et al. |
| 2004/0038388 | A1 | 2/2004 | Yamamoto et al. |
| 2005/0221351 | A1 | 10/2005 | Ryu |
| 2005/0240811 | A1 | 10/2005 | Safford et al. |
| 2005/0244863 | A1 | 11/2005 | Mir |
| 2005/0260611 | A1 | 11/2005 | Wang et al. |
| 2006/0088863 | A1 | 4/2006 | Yamamoto et al. |
| 2006/0172340 | A1 | 8/2006 | Wohlstadter et al. |
| 2007/0122841 | A1 | 5/2007 | Rajasekaran et al. |
| 2007/0122842 | A1 | 5/2007 | Rajasekaran et al. |
| 2007/0154946 | A1 | 7/2007 | Rajasekaran et al. |
| 2007/0231794 | A1 | 10/2007 | Dill et al. |
| 2008/0108149 | A1 | 5/2008 | Sundararajan et al. |
| 2009/0311727 | A1 | 12/2009 | Watkins et al. |
| 2009/0325816 | A1 | 12/2009 | Mirkin et al. |
| 2010/0028559 | A1 | 2/2010 | Yan et al. |
| 2010/0093554 | A1 | 4/2010 | Chu |
| 2010/0120630 | A1 | 5/2010 | Huang et al. |
| 2010/0240555 | A1 | 9/2010 | Sundararajan et al. |
| 2011/0097762 | A1 | 4/2011 | Gao et al. |
| 2011/0190210 | A1 | 8/2011 | Adini et al. |
| 2011/0281766 | A1 | 11/2011 | Cooper |
| 2011/0293644 | A1 | 12/2011 | Anderson et al. |
| 2011/0303027 | A1 | 12/2011 | Shirazi et al. |
| 2012/0172309 | A1 | 7/2012 | Dal Farra et al. |
| 2012/0183981 | A1 | 7/2012 | Norman et al. |
| 2012/0245057 | A1 | 9/2012 | Albert et al. |
| 2014/0072963 | A1 | 3/2014 | Qin |
| 2017/0168047 | A1 | 6/2017 | Aghvanyan et al. |

FOREIGN PATENT DOCUMENTS

| | | |
|---|---|---|
| JP | H06-500308 A | 1/1994 |
| JP | 2002-500362 A | 1/2002 |
| JP | 2002-502698 A | 1/2002 |
| JP | 2002-525577 A | 8/2002 |
| JP | 2003-517149 A | 5/2003 |
| JP | 2003-523348 A | 8/2003 |
| JP | 2003-342354 A | 12/2003 |
| JP | 2005-512032 A | 4/2005 |
| JP | 2005-513999 A | 5/2005 |
| JP | 2005-521032 A | 7/2005 |
| JP | 2005-264156 A | 9/2005 |
| JP | 2005-530983 A | 10/2005 |
| JP | 2007-504462 A | 3/2007 |
| JP | 2008-170449 A | 7/2008 |
| JP | 2009-075131 A | 4/2009 |
| JP | 2009-534200 A | 9/2009 |
| JP | 2010-507099 A | 3/2010 |
| JP | 2010-215816 A | 9/2010 |
| JP | 2011-017711 A | 1/2011 |
| JP | 2011-519168 A | 6/2011 |
| JP | 2011-234723 A | 11/2011 |
| JP | 2012-163491 A | 8/2012 |
| JP | 2012-518294 A | 8/2012 |
| WO | WO 1994/28075 A1 | 12/1994 |
| WO | WO 1998/03872 A2 | 1/1998 |
| WO | WO 1998/12539 A1 | 3/1998 |
| WO | WO 1999/41007 A2 | 8/1999 |
| WO | WO 2000/16089 A2 | 3/2000 |
| WO | WO 2001/43870 A2 | 6/2001 |
| WO | WO 2003/001889 A2 | 1/2003 |
| WO | WO 2003/023360 A2 | 3/2003 |
| WO | WO 2003/038033 A2 | 5/2003 |
| WO | WO 2003/104273 A2 | 12/2003 |
| WO | WO 2004/027093 A1 | 4/2004 |
| WO | WO 2005/014696 A1 | 2/2005 |
| WO | WO 2007/038647 A2 | 4/2007 |
| WO | WO 2007/078868 A1 | 7/2007 |
| WO | WO 2008/097370 A2 | 8/2008 |
| WO | WO 2008/118167 A1 | 10/2008 |
| WO | WO 2008/151146 A2 | 12/2008 |
| WO | WO 2009/132321 A1 | 10/2009 |
| WO | WO 2010/060155 A1 | 6/2010 |
| WO | WO 2010/085763 A1 | 7/2010 |
| WO | WO 2010/096593 A2 | 8/2010 |
| WO | WO 2011/027048 A1 | 3/2011 |
| WO | WO 2011/034620 A2 | 3/2011 |
| WO | WO 2011/058136 A1 | 5/2011 |
| WO | WO 2012/122929 A1 | 9/2012 |
| WO | WO 2012/122959 A1 | 9/2012 |
| WO | WO 2012/154594 A1 | 11/2012 |
| WO | WO 2012/174479 A1 | 12/2012 |
| WO | WO 2013/119845 A1 | 8/2013 |
| WO | WO 2014/052989 A2 | 4/2014 |
| WO | WO 2014/078606 A2 | 5/2014 |
| WO | WO 2015/016315 A1 | 2/2015 |
| WO | WO 2015/029691 A1 | 3/2015 |

OTHER PUBLICATIONS

Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.

Choung, R.S. et al., "Determination of B-Cell Epitopes in Patients with Celiac Disease: Peptide Microarrays," PLOS One, e0147777, Jan. 29, 2016, pp. 1-16, vol. 11, No. 1.

Fathalla, E. et al., "Efficient Synthesis of 1-Substituted-4-phenyl-1, 4-dihydro-5H-tetrazole-5-thione and (1-Phenyl-1H-tetrazol-5-yl)thiozcetyl Derivatives," Heteroatom Chemistry, 2007, vol. 18, No. 6, pp. 637-643.

(56) References Cited

OTHER PUBLICATIONS

Gomez-Zavaglia, A., et al., "Molecular structure, vibrational spectra and photochemistry of 5-mercapto-1- methyltetrazole," Journal of Molecular Structure, 2006, vol. 786, pp. 182-192.
Sun, X. et al., Bicyclic Guanidinium Tetraphenylborate: A Photobase Generator and a Photocatalyst for Living Anionic, J. Am. Chem. Soc., 2008, vol. 130, No. 26, pp. 8130-8131.
United States Office Action, U.S. Appl. No. 14/941,404, dated Dec. 11, 2018, 9 pages.
United States Office Action, U.S. Appl. No. 15/120,452, dated Sep. 18, 2017, 14 pages.
United States Office Action, U.S. Appl. No. 15/977,951, dated Aug. 30, 2019, 21 pages.
United States Office Action, U.S. Appl. No. 16/019,449, Apr. 29, 2019, 7 pages.
Alawode, O. E. et al., "Clean Photodecompositionof 1-Methyl-4-Phenyl-1HTetrazole-5(4H)-Thiones to Carbodiimides Proceeds Via a Biradical," The Journal of Organic Chemistry, Jan. 7, 2011, pp. 216-222, vol. 76, No. 1.
Arimatsu, K., "Development of Highly Sensitive Photoreactive Materials Utilizing Photo Base-Generating Reactions and Base Proliferation Reactions," Yuki Gosei Kagaku Kyokaishi—Journal of Synthetic Organic Chemistry, Jan. 2012, pp. 508-516, vol. 70, No. 5.
Beyer, M. et al., "Combinatorial Synthesis of Peptide Arrays Onto a Microchip," Science, Dec. 21, 2007, p. 1888, vol. 318, No. 5858.
Camarero, J. A., "Review Article: Recent Developments in the Site-Specific Immobilization of Proteins Onto Solid Supports," Biopolymers (PeptideScience), 2008, pgs. 450-458, vol. 90, No. 3.
Canadian First Office Action, Canadian Application No. 2,864,080, dated Nov. 19, 2015, 6 pages.
Canadian Office Action, Canadian Application No. 2,864,080, dated Jul. 10, 2017, 5 pages.
Canadian Office Action, Canadian Application No. 2,885,839, dated Jul. 22, 2016, 4 pages.
Canadian Office Action, Canadian Application No. 2,885,839, dated Sep. 15, 2017, 4 pages.
Canadian Office Action, Canadian Application No. 2,891,651, dated Jun. 2, 2016, 5 pages.
Canadian Office Action, Canadian Application No. 2,891,651, dated Sep. 15, 2017, 4 pages.
Canadian Office Action, Canadian Application No. 2,901,029, dated Dec. 2, 2016, 7 pages.
Canadian Office Action, Canadian Application No. 2,901,029, dated Jul. 5, 2017, 8 pages.
Canadian Office Action, Canadian Application No. 2,901,029, dated May 5, 2016, 7 pages.
Canadian Office Action, Canadian Application No. 2,901,029, dated Mar. 21, 2018, 8 pages.
Canadian Office Action, Canadian Application No. 2,901,029, dated Sep. 8, 2015, 4 pages.
Canadian Second Office Action, Canadian Application No. 2,864,080, dated Dec. 1, 2016, 5 pages.
Canadian Second Office Action, Canadian Application No. 2,885,839, dated Apr. 20, 2017, 4 pages.
Canadian Second Office Action, Canadian Application No. 2,891,651, dated Feb. 10, 2017, 4 pages.
Carra, C. et al., "Proton-Coupled Electron Transfer in a Model for Tyrosine Oxidation in Photosystem II," Journal of the American Chemical Society, 2003, pp. 10429-10436, vol. 125.
Compound Summary for: CID 44140583, Tris(2,2'-bipyridine)ruthenium(II) dicholoride, 2009, 2 pages, [Online] [Retrieved dated Jun. 29, 2014] Retrieved from the InternetURL:http://pubchem.ncbi.nlm.nih.gov/summary/summary.cgi?cid=44140593&loc=ec_rcs>.
European Communication Under Rule 164(2)(a) EPC, European Application No. 13798499.3, dated Jun. 29, 2016, 4 pages.
European Examination Report, European Application No. 13747275.9, dated Sep. 21, 2017, 6 pages.

European Examination Report, European Application No. 13783134.3, dated Jun. 29, 2016, 12 pages.
European Examination Report, European Application No. 13783134.3, dated Apr. 1, 2016, 4 pages.
European Examination Report, European Application No. 13783134.3, dated Dec. 19, 2017, 5 pages.
European Examination Report, European Application No. 13798499.3, dated Sep. 23, 2016, 10 pages.
European Examination Report, European Application No. 14751871.6, dated Jul. 20, 2017, 5 pages.
European Extended Search Report, European Application No. 13747275.9, dated Sep. 25, 2015, 9 pages.
European Extended Search Report, European Application No. 14751871.6, dated Aug. 2, 2016, 6 pages.
European Invitation to Pay Additional Search Fees, European Application No. 13783134.3, dated May 2, 2016, 4 pages.
European Second Examination Report, European Application No. 13798499.3, dated May 23, 2017, 6 pages.
Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet<URL:http://krex.kstate.edu/dspace/handle/2097/12022>.
Han, S-Y. et al., "Recent Development of Peptide Coupling Reagents in Organic Synthesis," Tetrahedron, 2004, pp. 2447-2467, vol. 60.
Japanese Office Action, Japanese Application No. 2014-556684, dated Apr. 4, 2016, 5 pages.
Japanese Office Action, Japanese Application No. 2015-534809, dated Aug. 28, 2017, 6 pages.
Japanese Office Action, Japanese Application No. 2015-558184, dated Jan. 25, 2016, 4 pages.
Japanese Office Action, Japanese Application No. 2016-126181, dated May 22, 2017, 10 pages.
Japanese Office Action, Japanese Application No. 2016-148004, dated Jun. 21, 2017, 7 pages.
Lim, J-H. et al., "Direct-Write Dip-Pen Nanolithography of Proteins on Modified Silicon Oxide Surfaces," Angewandte Chemie International Edition, Wile-V CH Verlag GmbH * Co. KGAA, DE, May 25, 2003, pp. 2309-2312, vol. 42, No. 20.
Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).
Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.
Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.
PCT International Preliminary Report on Patentability for PCT International Application No. PCT/US13/62773, Dec. 18, 2014, 7 pages.
PCT International Preliminary Report on Patentability for PCT International Application No. PCT/US14/16737, Feb. 24, 2015, 6 pages.
PCT International Preliminary Report on Patentability for PCT International Application No. PCT/US13/25190, Apr. 4, 2014, 18 pages.
PCT International Preliminary Report on Patentability, PCT Application No. PCT/US2013/070207, Mar. 30, 2015, 12 pages.
PCT International Search Report and Written Opinion, PCT Application No. PCT/US2013/062773, dated May 28, 2014, 20 pages.
PCT International Search Report and Written Opinion, PCT Application No. PCT/US14/16737, dated Aug. 11, 2014, 17 pages.
PCT International Search Report and Written Opinion, PCT Application No. PCT/US13/25190, dated Jun. 26, 2013, 22 pages.
PCT International Search Report and Written Opinion, PCT Application No. PCT/US15/017173, dated Jun. 3, 2015, 15 pages.
PCT International Search Report and Written Opinion, PCT Application No. PCT/US15/49528, dated Feb. 1, 2016, 18 pages.

(56) References Cited

OTHER PUBLICATIONS

PCT International Search Report and Written Opinion, PCT Application No. PCT/US2013/070207, dated Jun. 23, 2014, 19 pages.
PCT Invitation to Pay Additional Fees, PCT Application No. PCT/US2013/062773, Mar. 7, 2014, 9 pages.
PCT Invitation to Pay Additional Fees, PCT Application No. PCT/US14/16737, May 19, 2014, 2 pages.
PCT Invitation to Pay Additional Fees, PCT Application No. PCT/US13/25190, May 1, 2013, 4 pages.
PCT Invitation to Pay Additional Fees, PCT Application No. PCT/US15/49528, Nov. 20, 2015, 3 pages.
PCT Invitation to Pay Additional Fees, PCT Application No. PCT/US2013/070207, Mar. 14, 2014, 8 pages.
PCT Written Opinion of the International Preliminary Examining Authority, PCT Application No. PCT/US2013/070207, Feb. 12, 2015, 13 pages.
Pellois, J.P. et al., "Individually Addressable Parallel Peptide Synthesis on Microchips". Nature Biotechnology, Sep. 2002, pp. 922-926, vol. 20, No. 9.
Piehler, J. et al., "Protein Interactions in Covalently Attached Dextran Layers," Colloids and Surfaces B: Biointerfaces Jul. 13, 1999, pps. 325-336.
"Proteomics 2010: Solid-Phase Peptide Synthesis (SPPS) and Applications of Synthetic Peptides," Jan. 2010, 63 pages [Online] [Retrieved on Sep. 16, 2015] Retrieved from the Internet<URL:http://bas.niu.edu.tw/download.php?filename=12155_cf09f16c.ppt&dir=communicty_forum/31&title=Topic+ 10-SPPS>.
Resch-Genger et al., "Quantum Dots Versus Organic Dyes as Fluorescent Labels," Nature Methods, Sep. 2008, pp. 763-775, vol. 5, No. 9.
Sardesai, N. P., et al., "A Microfluidic Electrochemiluminescent Device for Detecting Cancer Biomarker Proteins," Anal Bioanal Chem., 2013, pp. 3831-3838; vol. 405, No. 11.
Shin, D-S. et al., "Automated Maskless Photolithography System for Peptide Microarray Synthesis on a Chip," J. Comb. Chem., 2010, pp. 463-471, vol. 12.
Sun, X. et al., "Bicyclic Guanidinium Tetraphenylborate: a Photobase Generator and a Photocatalyst for Living Anionic Ring-Opening Polymerization and Cross-Linking of Polymeric Materials Containing Ester and Hydroxy Groups," Journal of the American Chemical Society, Jul. 2008, pp. 8130-8131, vol. 130, No. 26.
Suyama, K. et al., "Photobase Generators: Recent Progress and Application Trend in Polymers Systems," Progress in Polymer Science, Pergamon Press, Oxford, GB, Feb. 2009, pp. 194-209, vol. 34, No. 2.
Tapia, V. et al., "Evaluating the Coupling Efficiency of Phosphorylated Amino Acids for SPOT Synthesis," Journal of Peptide Science, 2008, pp. 1309-1314, vol. 14.
Uddayasankar, U., "Towards a Surface Microarray Based Multiplexed Immunoassay on a Digital Microfluidics Platform," 2010, pgs. 1-69, Master of Science Thesis. Retrieved from the Internet Jun. 29, 2014: <https://cipweb.cardinal-ip.com/PCTSRS/PCTSRS DAT A/PCT-US%2014-16737/PRIOR_ART PCTPCTUS14-16737 Uddavasankar Master Thesis 2010.pdf>.
United States Office Action, U.S. Application No. 14/432,200, Jul. 19, 2017, 17 pp.
United States Office Action, U.S. Application No. 14/454,554, Mar. 16, 2015, 14 pp.
United States Office Action, U.S. Application No. 14/672, 123, Dec. 21, 2015, 10 pp.
United States Office Action, U.S. Application No. 14/768,196, Sep. 22, 2017, 18 pp.
United States Office Action, U.S. Patent Application No. 14/768,196, May 30, 2018, 16 pp.
United States Office Action, U.S. Patent Application No. 14/941,404, May 30, 2018, 10 pp.
Wagner, J., "Quality Control for Peptide Chop Array Production," Ph.D. Thesis, University of Heidelberg, Germany, Oct. 2011, 140 pp.
Wang et al, Microfluidic Dna microarray analysis: a review, 2011, Analytica Chimica Acta, 687, 12-27.
\Nei, H. et al., "Electrochemiluminescence of tris(2,2'-bipyridyl)ruthenium and Its Applications in Bioanalysis: a Review," Luminescence, Mar.-Apr. 2011, pp. 77-85, vol. 26, Issue 2.
Young, et al., Peptide Research, Jul. 1990, pp. 194-200, vol. 3, No. 4.
Yuan, L., et al., "Integrated Tyramide and Polymerization-Assisted Signal Amplification for a Highly-Sensitive Immunoassay," Anal. Chem., 2012, pp. 10737-10744, vol. 84, No. 24.
Zhao, Y. et al., "A Fluorescent Amino Acid Probe to Monitor Efficiency of Peptide Conjugation to Glass Surfaces for High Density Microarrays," Molecular Biosystems, 2012, pp. 879-887. vol. 83.
Fodor, et al., "Light-Direct, Spatially Addressable Parallel Chemical Synthesis", Science, 1991, vol. 251, No. 4995: pp. 767-773.
Frija, et al., "Photochemical Transformations of Tetrazole Derivatives: Applications in Organic Synthesis", Molecules, 2010, vol. 15, No. 5: pp. 3757-3774.
Gutheil, et al., "N-to-C Solid-Phase Peptide and Peptide Trifluoromethylketone Synthesis Using Amino Acid tert-Butyl Esters", Chem. Pharm. Bull, 2002, vol. 50, No. 5: pp. 688-691.
Pellois, et al., "Peptide Synthesis Based on t-Boc Chemistry and Solution Photogenerated Acids", J. Combinatorial Chem., 2000, vol. 2, No. 4: pp. 355-360.

SUBSTRATES, SYSTEMS, AND METHODS FOR ARRAY SYNTHESIS AND BIOMOLECULAR ANALYSIS

CROSS-REFERENCE TO RELATED APPLICATIONS

This application is a continuation of U.S. patent application Ser. No. 14/442,389, filed May 12, 2015, which is the National Stage of International Patent Application No. PCT/US/2013/070207, filed Nov. 14, 2013, which claims the benefit of U.S. Provisional Patent Application No. 61/726,515 filed Nov. 14, 2012, U.S. Provisional Patent Application No. 61/732,221, filed Nov. 30, 2012, U.S. Provisional Patent Application No. 61/805,884, filed Mar. 27, 2013, U.S. Provisional Patent Application No. 61/765,584, filed Feb. 15, 2013, U.S. Provisional Patent Application No. 61/866,512, filed Aug. 15, 2013; PCT/US2013/070207 is also a continuation-in-part of International Patent Application No. PCT/US2013/062773, filed Sep. 30, 2013, which is a continuation-in-part of PCT/US2013/025190, filed Feb. 7, 2013, which claims the benefit of U.S. Provisional Patent Application No. 61/761,347, filed Feb. 6, 2013.

SEQUENCE LISTING

The instant application contains a Sequence Listing which has been submitted via EFS-Web and is hereby incorporated by reference in its entirety. Said ASCII copy, created on Jul. 14, 2020, is named VIB-007C1_sequence_listing.txt, and is 3,567 bytes in size.

BACKGROUND

A typical microarray system is generally comprised of biomolecular probes, such as DNA, proteins, or peptides, formatted on a solid planar surface like glass, plastic, or silicon chip, plus the instruments needed to handle samples (automated robotics), to read the reporter molecules (scanners) and analyze the data (bioinformatic tools). Microarray technology can facilitate monitoring of many probes per square centimeter. Advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

Recent advances in genomics have culminated in sequencing of entire genomes of several organisms, including humans. Genomics alone, however, cannot provide a complete understanding of cellular processes that are involved in disease, development, and other biological phenomena; because such processes are often directly mediated by polypeptides often as participants in ligand-receptor binding reactions. Given the large numbers of polypeptides are encoded by the genome of an organism, the development of high throughput technologies for analyzing polypeptides is of paramount importance.

Peptide arrays with distinct analyte-detecting regions or probes can be assembled on a single substrate by techniques well known to one skilled in the art. A variety of methods are available for creating a peptide microarray. These methods include: (a) chemo selective immobilization methods; and (b) in situ parallel synthesis methods which can be further divided into (1) SPOT synthesis and (2) photolithographic synthesis. However, chemo selective immobilization methods of the prior art tend to be cumbersome, requiring multiple steps, or are difficult to control spatially, limiting the feature density that can be achieved using these methods, and in situ parallel synthesis methods of the prior art suffer from deficiencies relating to low or inconsistent coupling efficiencies across multiple coupling cycles. The methods in the prior art suffer from slow feature synthesis. The present invention addresses these and other shortcomings of the prior art by providing substrates, systems, and methods for array synthesis and biomolecular analysis as described in detail below.

SUMMARY

Embodiments of the invention include formulations, substrates, and arrays. Embodiments also include methods for manufacturing and using the formulations, substrates, and arrays. One embodiment includes an array that is manufactured using a photoactive coupling formulation, a carboxylic acid activating compound, and a substrate comprising carboxylic acid groups. In some embodiments, the photoactive coupling formulation comprises a photoactive compound, a coupling molecule, a polymer, and a solvent. Another embodiment includes an array that is manufactured using a coupling formulation, a photoactive carboxylic acid activating compound, and a substrate comprising carboxylic acid groups. In some embodiments, the coupling formulation comprises a coupling molecule, a polymer, and a solvent. In some embodiments, attaching the coupling molecule to the substrate comprises selectively exposing either the photoactive compound or the photoactive carboxylic acid activating compound to light. In some embodiments, the photoactive compound is about 0.5-5% by weight of the total formulation.

Examples of coupling molecules include, but are not limited to, amino acids, peptides, proteins, DNA binding sequences, antibodies, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. In one embodiment, the coupling molecule comprises a naturally occurring or artificial amino acid or polypeptide. In some embodiments, the artificial amino acid is a D-amino acid. In some embodiments, the coupling molecule is 1-2% by weight of the total formulation. In some embodiments, the coupling molecule comprises a protected group. In some embodiments, the group is protected by Fmoc.

In some embodiments, the photoactive carboxylic acid activating compound comprises a carbodiimide precursor compound of formula (I):

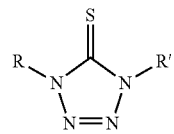

wherein
R is selected from a group comprising hydrogen, substituted or unsubstituted alkyl, substituted or unsubstituted alkenyl, and substituted or unsubstituted heterocyclyl, and
R further comprises a water-solubilizing group; and
R' is substituted or unsubstituted alkyl, substituted or unsubstituted alkenyl, substituted or unsubstituted aryl, substituted or unsubstituted cycloalkyl, and substituted or unsubstituted heterocyclyl.

In other embodiments, the photoactive compound comprises a photobase generator. Some embodiments comprises a photobase generator compound of formula (II):

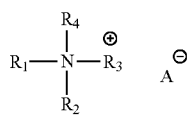

wherein

is an anion selected from the group consisting of:

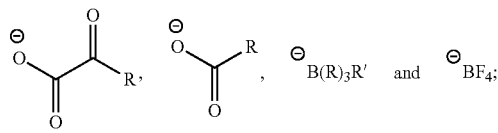

R is a substituted or unsubstituted aryl;
R' is an aryl, alkyl, alkenyl, alkoxy, cyano, —NO$_2$ or fluoro, said aryl, said alkyl, said alkenyl, and said alkoxy being optionally substituted;

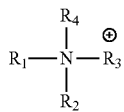

is a nitrogen-containing cation, the nitrogen-containing cation comprising a heteroaryl or heterocyclyl, said heteraryl or heterocyclyl containing one or more nitrogen atoms.

In some embodiments, the photoactive compound comprises a photobase generator compound of formula (II), wherein

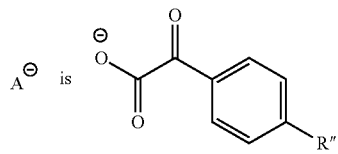

or tetraphenylborate;
R" is hydrogen or —NO$_2$;

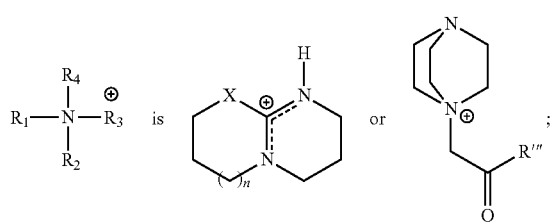

X is NH or CH$_2$;
n is an integer from 0 to 3; and
R'" is aryl or heteroaryl.

In some embodiments, the photobase generator is 1,3-Bis[(2-nitrobenzyl)oxycarbonyl-4-piperidyl]propane or 1,3-Bis[1-(9-fluorenylmethoxycarbonyl)-4-piperidyl]propane. In some embodiments, the photobase generator is carbamate, O-acyloxime, ammonium salt, amineimide, α-aminoketone, amidine precursor, or aromatic urea.

Particular embodiments of photobase generator compounds and carbodiimide precursor compounds are shown in Tables 1-4. More particular embodiments of photoactive coupling formulations are shown in Table 5.

In certain embodiments, the carboxylic acid activating compound, also referred to as a "coupling reagent" herein, is a carbodiimide. In some embodiments, the coupling reagent is diisopropylcarbodiimide or N-hydroxy-5-norbornene-2,3-dicarboximide. In some embodiments, the polymer is polymethyl methacrylate.

In some embodiments, the formulations are miscible with water. In some embodiments, the solvent is water, an organic solvent, or a combination thereof. In certain embodiments, the organic solvent comprises ethyl lactate or methylpyrrolidone. In some embodiments, the solvent is about 80-90% by weight of the total formulation.

Also encompassed is a substrate, comprising: a first layer, wherein the layer comprises a plurality of unprotected carboxylic acid groups. In some embodiments, the first layer is a porous layer. In some embodiments, the carboxylic acid groups are oriented in multiple directions on the surface of the porous layer.

In an embodiment, the first layer is coupled to a support layer. In an embodiment, the first layer is coupled to a silicon wafer. In certain embodiments, the porous layer comprises dextran. In other embodiments, the porous layer comprises porous silica. In an embodiment, the porous layer comprises pores of a pore size of about 2 nm to 100 μm. In an embodiment, the porous layer comprises a porosity of about 10-80%. In an embodiment, the porous layer comprises a thickness of about 0.01 μm to about 10,000 μm.

In some embodiments, the substrate further comprises a planar layer comprising a metal having an upper surface and a lower surface. In some embodiments, the first layer is coupled to the planar layer. In some embodiments, the first layer is coated on top of the planar layer. In some embodiments, the substrate further comprises a plurality of wells.

In an embodiment, the substrate further comprises a plurality of pillars operatively coupled to the planar layer in positionally-defined locations, wherein each pillar has a planar surface extended from the planar layer, wherein the distance between the surface of each pillar and the upper surface of the layer is between 1,000-5,000 angstroms, and wherein the plurality of pillars are present at a density of greater than 10,000/cm$^2$, and wherein the first layer is deposited on the planar surface of the pillars. In some embodiments, the surface area of each pillar surface is at least 1 μm$^2$. In some embodiments, the surface area of each pillar surface has a total area of less than 10,000 μm$^2$. In some embodiments, the distance between the surface of each pillar and the lower surface of the layer is 2,000-7,000 angstroms. In some embodiments, the planar layer is 1,000-2,000 angstroms thick. In some embodiments, the center of each pillar is at least 2,000 angstroms from the center of any other pillar. In some embodiments, the surface of each pillar is parallel to the upper surface of the planar layer. In some embodiments, the surface of each pillar is substantially parallel to the upper surface of the planar layer. In certain embodiments, the metal is chromium. In some embodiments, the metal is chromium, titanium, aluminum, tungsten, gold, silver, tin, lead, thallium, or indium. In some embodiments, the planar layer is at least 98.5-99% metal by weight. In some embodiments, the planar layer is a homogenous layer of metal. In some embodiments, each pillar comprises silicon dioxide or silicon nitride. In some embodiments, each pillar is at least 98-99% silicon dioxide by weight.

In an embodiment, the substrate further comprises a linker molecule having a free amino terminus attached to at least one of the carboxylic acid groups. In some embodiments, the substrate further comprises a linker molecule having a free carboxylic acid group attached to at least one of the carboxylic acid groups. In some embodiments, the substrate further comprises a coupling molecule attached to at least one of the carboxylic acid groups. In some embodiments, the substrate further comprises a polymer chain attached to at least one of the carboxylic acid groups.

In an embodiment, the polymer chain comprises a peptide chain. In some embodiments, the polymer chain is attached to at least one of the carboxylic acid groups via a covalent bond.

Another embodiment encompasses a three-dimensional array of features attached to a surface at positionally-defined locations, the features each comprising: a collection of peptide chains of determinable sequence and intended length, wherein within an individual feature, the fraction of peptide chains within the collection having the intended length is characterized by an average coupling efficiency for each coupling step of at least 98%.

In an embodiment, the array comprises a porous layer. In some embodiments, the porous layer comprises a plurality of free carboxylic acid groups. In some embodiments, the porous layer comprises a plurality of coupling molecules each attached to the array via a carboxylic acid group. In some embodiments, the porous layer comprises a plurality of peptide chains each attached to the array via a carboxylic acid group.

In certain embodiments, the average coupling efficiency of each coupling step is at least 98.5%. In some embodiments, the average coupling efficiency of each coupling step is at least 92%, 93%, 94%, 95%, 96%, 97%, 98%, or 99%. In some embodiments, each peptide chain is from 6 to 60 amino acids in length. In some embodiments, each peptide chain is at least 6 amino acids in length. In some embodiments, each peptide chain is at least 6, 10, 15, 20, 25, 30, 35, 40, 45, 50, 55, or 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids. In some embodiments, the array comprises at least 1,000 different peptide chains attached to the surface. In some embodiments, the array comprises at least 10,000 different peptide chains attached to the surface.

In an embodiment, each of the positionally-defined locations is at a different, known location that is physically separated from each of the other positionally-defined locations. In some embodiments, each of the positionally-defined locations comprises a plurality of identical sequences. In some embodiments, each positionally-defined location comprises a plurality of identical sequences unique from the other positionally-defined locations. In some embodiments, each of the positionally-defined locations is a positionally-distinguishable location. In certain embodiments, each determinable sequence is a known sequence. In certain embodiments, each determinable sequence is a distinct sequence. In some embodiments, the features are covalently attached to the surface. In some embodiments, peptide chains are attached to the surface through a linker molecule or a coupling molecule.

In certain embodiments, the features comprise a plurality of distinct, nested, overlapping peptide chains comprising subsequences derived from a source protein having a known sequence. In an embodiment, each peptide chain in the plurality is at least 5 amino acids in length. In some embodiments, each peptide chain in the plurality is at least 5, 10, 15, 20, 25, 30, 35, 40, 45, 50, 55, or 60 amino acids in length.

In some embodiments, the features comprise a plurality of peptide chains each having a random, determinable sequence of amino acids.

One embodiment includes a method of attaching a coupling molecule to a substrate, comprising: obtaining a substrate comprising a plurality of carboxylic acid groups for linking to a coupling molecule; contacting the substrate a carboxylic acid activating compound; contacting the substrate with a photoactive coupling formulation comprising a photoactive compound, a protected coupling molecule, a polymer, and a solvent; selectively exposing the photoactive coupling formulation to light, thereby deprotecting the protected coupling molecule at a selectively exposed area; coupling the unprotected coupling molecule to at least one of the plurality of carboxylic acid groups at the selectively exposed area; and optionally repeating the method to produce a desired polymer at the at least one carboxylic acid group.

Another embodiment includes a method of attaching a coupling molecule to a substrate, comprising: obtaining a substrate comprising a plurality of carboxylic acid groups for linking to a coupling molecule; contacting the substrate with a photoactive carboxylic acid activating compound; selectively exposing the photoactive carboxylic acid activating compound to light, thereby generating carbodiimide at a selectively exposed area and activating the carboxylic acid groups on the substrate; contacting the substrate with a coupling formulation comprising an unprotected coupling molecule, a polymer, and a solvent; coupling the unprotected coupling molecule to at least one of the plurality of carboxylic acid groups at the selectively exposed area; and optionally repeating the method to produce a desired polymer at the at least one carboxylic acid group.

In an embodiment, the coupling step has an efficiency of at least 98%. In an embodiment, the coupling molecule is an amino acid. In an embodiment, the polymer is a polypeptide. In an embodiment, the substrate comprises a porous layer comprising a plurality of attachment sites extending in multiple dimensions from the surface of the porous layer within and around the porous layer. In an embodiment, the attachment site comprises an unprotected carboxylic acid group for binding to the coupling molecule.

In some embodiments, the substrate comprises a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than 10,000/cm$^2$, and wherein the attachment site is coupled to the upper surface of the pillar.

Another embodiment includes a method of producing a three-dimensional array of features, comprising: obtaining a porous layer comprising a plurality of unprotected carboxylic acid groups; and attaching the features to the unprotected carboxylic acid groups, the features each comprising a collection of peptide chains of determinable sequence and intended length. In some embodiments, the carboxylic acid groups are oriented in multiple directions.

In some embodiments, within an individual feature, the fraction of peptide chains within the collection having the intended length is characterized by an average coupling efficiency for each coupling step of at least 98%. In some embodiments, the features are attached to the surface using a coupling formulation comprising a solvent, a polymer, a coupling molecule, a neutralization reagent, and a coupling reagent.

One further embodiment includes a method of detecting biomolecules in a sample, comprising: providing a substrate comprising at least one porous layer, wherein the layer comprises a plurality of peptide chains attached to carboxylic acid groups, wherein the peptide chains have a known sequence according to positionally-defined locations; contacting the substrate with the sample; and detecting binding events of biomolecules within the sample to the peptide chains. In some embodiments, the carboxylic acid groups are oriented in multiple directions.

In an embodiment, the sample is a biological sample. In an embodiment, the biological sample is a bodily fluid. In some embodiments, the bodily fluid is amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine. In some embodiments, the biomolecule is a protein. In some embodiments, the biomolecule is an antibody.

In some embodiments, the method has a greater than 40 fold increase in sensitivity of biomolecule detection as compared to a substrate comprising peptide chains attached to a planar layer.

BRIEF DESCRIPTION OF THE SEVERAL VIEWS OF THE DRAWINGS

These and other features, embodiments, and advantages of the present invention will become better understood with regard to the following description, and accompanying drawings, where.

DETAILED DESCRIPTION

Figure 1:
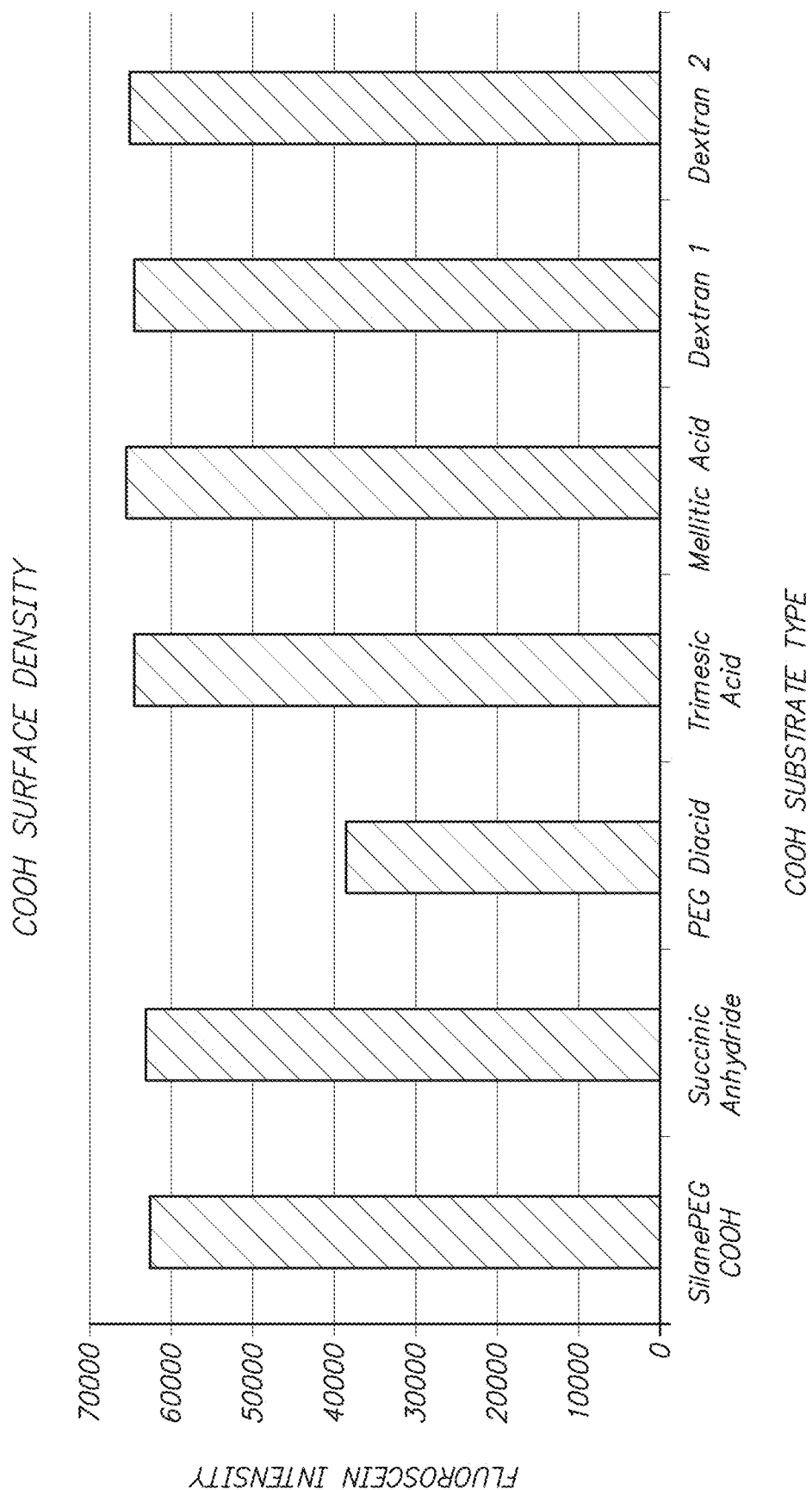
FIG. 1 shows a measure of density of activated carboxylic acid groups on the surface of a wafer synthesized by selected methods as described herein.

Terms used in the claims and specification are defined as set forth below unless otherwise specified.

As used herein the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 µm to 775 µm.

As used herein the term "photoresist" or "resist" or "photoactive material" refers to a light-sensitive material that changes its solubility in a solution when exposed to ultra violet or deep ultra violet radiation. Photoresists are organic or inorganic compounds that are typically divided into two types: positive resists and negative resists. A positive resist is a type of photoresist in which the portion of the photoresist that is exposed to light becomes soluble to the photoresist developer. The portion of the photoresist that is unexposed remains insoluble to the photoresist developer. A negative resist is a type of photoresist in which the portion of the photoresist that is exposed to light becomes insoluble to the photoresist developer. The unexposed portion of the photoresist is dissolved by the photoresist developer.

As used herein the term "photomask" or "reticle" or "mask" refers to an opaque plate with transparent patterns or holes that allow light to pass through. In a typical exposing process, the pattern on a photomask is transferred onto a photoresist As used herein the term "photoactive compound" refers to compounds that are modified when exposed to electromagnetic radiation. These compounds include, for example, cationic photoinitiators such as photoacid or photobase generators, which generate an acid or a base, respectively, when exposed to electromagnetic radiation. A photoinitiator is a compound especially added to a formulation to convert electromagnetic radiation into chemical energy in the form of initiating species, e.g., free radicals or cations. The acid, base, or other product of a photoactive compound exposed to electromagnetic radiation may then react with another compound in a chain reaction to produce a desired chemical reaction. The spatial orientation of the occurrence of these chemical reactions is thus defined according to the pattern of electromagnetic radiation the solution or surface comprising photoactive compounds is exposed to. This pattern may be defined, e.g., by a photomask or reticle.

As used herein the term "coupling molecule" or "monomer molecule" includes any natural or artificially synthesized amino acid with its amino group protected with a fluorenylmethyloxycarbonyl (Fmoc or F-Moc) group or a t-butoxycarbonyl (tboc or Boc) group. These amino acids may have their side chains protected as an option. Examples of coupling molecules include Boc-Gly-OH, Fmoc-Trp-OH. Other examples are described below.

As used here in the term "coupling" or "coupling process" or "coupling step" refers to a process of forming a bond between two or more molecules such as a linking molecule or a coupling molecule. A bond can be a covalent bond such as a peptide bond. A peptide bond is a chemical bond formed between two molecules when the carboxyl group of one coupling molecule reacts with the amino group of the other coupling molecule, releasing a molecule of water ($H_2O$). This is a dehydration synthesis reaction (also known as a condensation reaction), and usually occurs between amino acids. The resulting —C(=O)NH— bond is called a peptide bond, and the resulting molecule is an amide.

As used herein the term "coupling efficiency" refers to the probability of successful addition of a monomer to a reaction site (e.g., at the end of a polymer) available for binding to the monomer. For example, during the growth of a peptide chain in the N to C orientation, a polypeptide having a free carboxyl group would bind to an amino acid having a free amine group under appropriate conditions. The coupling efficiency gives the probability of the addition of a free amino acid to the free carboxyl group under certain conditions. It may be determined in bulk, e.g., by monitoring single monomer additions to several unique reaction sites simultaneously.

As used herein the terms "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some embodiments, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "biomarkers" includes, but is not limited to DNA, RNA, proteins (e.g., enzymes such as kinases), peptides, sugars, salts, fats, lipids, ions and the like.

As used herein the term "linker molecule" or "spacer molecule" includes any molecule that does not add any functionality to the resulting peptide but spaces and extends the peptide out from the substrate, thus increasing the distance between the substrate surface and the growing peptide. This generally reduces steric hindrance with the substrate for reactions involving the peptide (including uni-molecular folding reactions and multi-molecular binding reactions) and so improves performance of assays measuring one or more embodiments of peptide functionality.

As used herein the term "developer" refers to a solution that can selectively dissolve the materials that are either exposed or not exposed to light. Typically developers are water-based solutions with minute quantities of a base added. Examples include tetramethyl ammonium hydroxide in water-based developers. Developers are used for the initial pattern definition where a commercial photoresist is used.

As used herein the term "protecting group" includes a group that is introduced into a molecule by chemical modification of a functional group to obtain chemoselectivity in a subsequent chemical reaction. Chemoselectivity refers to directing a chemical reaction along a desired path to obtain a pre-selected product as compared to another. For example, the use of tboc as a protecting group enables chemoselectivity for peptide synthesis using a light mask and a photoacid generator to selectively remove the protecting group and direct pre-determined peptide coupling reactions to occur at locations defined by the light mask.

As used herein the term "microarray," "array" or "chip" refers to a substrate on which a plurality of probe molecules of protein or specific DNA binding sequences have been affixed at separate locations in an ordered manner thus forming a microscopic array. Protein or specific DNA binding sequences may be bound to the substrate of the chip through one or more different types of linker molecules. A "chip array" refers to a plate having a plurality of chips, for example, 24, 96, or 384 chips.

As used herein the term "probe molecules" refers to, but is not limited to, proteins, DNA binding sequences, antibodies, peptides, oligonucleotides, nucleic acids, peptide nucleic acids ("PNA"), deoxyribonucleic acids (DNA), ribonucleic acids (RNA), peptide mimetics, nucleotide mimetics, chelates, biomarkers and the like. As used herein, the term "feature" refers to a particular probe molecule that has been attached to a microarray. As used herein, the term "ligand" refers to a molecule, agent, analyte or compound of interest that can bind to one or more features.

As used herein the term "microarray system" or a "chip array system" refers to a system usually comprised of bio molecular probes formatted on a solid planar surface like glass, plastic or silicon chip plus the instruments needed to handle samples (automated robotics), to read the reporter molecules (scanners) and analyze the data (bioinformatic tools).

As used herein the term "patterned region" or "pattern" or "location" refers to a region on the substrate on which are grown different features. These patterns can be defined using photomasks.

As used herein the term "derivatization" refers to the process of chemically modifying a surface to make it suitable for biomolecular synthesis. Typically derivatization includes the following steps: making the substrate hydrophilic, adding an amino silane group, and attaching a linker molecule.

As used herein the term "capping" or "capping process" or "capping step" refers to the addition of a molecule that prevents the further reaction of the molecule to which it is attached. For example, to prevent the further formation of a peptide bond, the amino groups are typically capped with an acetic anhydride molecule. In other embodiments, ethanolamine is used.

As used herein the term "diffusion" refers to the spread of, e.g., photoacid or photobase through random motion from regions of higher concentration to regions of lower concentration.

As used herein the term "dye molecule" refers to a dye which typically is a colored substance that can bind to a substrate. Dye molecules can be useful in detecting binding between a feature on an array and a molecule of interest.

As used herein, the terms "immunological binding" and "immunological binding properties" refer to the non-covalent interactions of the type which occur between an immunoglobulin molecule and an antigen for which the immunoglobulin is specific.

As used herein the term "biological sample" refers to a sample derived from biological tissue or fluid that can be assayed for an analyte(s) of interest. Such samples include, but are not limited to, sputum, amniotic fluid, blood, blood cells (e.g., white cells), tissue or fine needle biopsy samples, urine, peritoneal fluid, and pleural fluid, or cells therefrom. Biological samples may also include sections of tissues such as frozen sections taken for histological purposes. Although the sample is typically taken from a human patient, the assays can be used to detect analyte(s) of interest in samples from any organism (e.g., mammal, bacteria, virus, algae, or yeast) or mammal, such as dogs, cats, sheep, cattle, and pigs. The sample may be pretreated as necessary by dilution in an appropriate buffer solution or concentrated, if desired.

As used herein, the term "assay" refers to a type of biochemical test that measures the presence or concentration of a substance of interest in solutions that can contain a complex mixture of substances.

The term "antigen" as used herein refers to a molecule that triggers an immune response by the immune system of a subject, e.g., the production of an antibody by the immune system. Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies.

Any such distinct molecular feature can constitute an epitope. Therefore, antigens have the potential to be bound by several distinct antibodies, each of which is specific to a particular epitope.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

Unless otherwise noted, "alkyl" as used herein, whether used alone or as part of a substituent group, refers to a saturated, branched, or straight-chain monovalent hydrocarbon radical derived by the removal of one hydrogen atom from a single carbon atom of a parent alkane. Typical alkyl groups include, but are not limited to, methyl; ethyls; propyls such as propan-1-yl, propan-2-yl; butyls such as butan-1-yl, butan-2-yl, 2-methyl-propan-1-yl, 2-methyl-propan-2-yl, and the like. In preferred embodiments, the alkyl groups are $C_{1-6}$alkyl, with $C_{1-3}$alkyl being particularly preferred. "Alkoxyl" radicals are oxygen ethers formed from the previously described straight or branched chain alkyl groups.

As used herein, "halo" or "halogen" shall mean chlorine, bromine, fluorine and iodine. "Halo substituted" shall mean a group substituted with at least one halogen atom, preferably substituted with a least one fluoro atom. Suitable examples include, but are not limited to $—CF_3$, and the like.

The term "cycloalkyl," as used herein, refers to a stable, saturated or partially saturated monocyclic or bicyclic ring system containing from 3 to 8 ring carbons and preferably 5 to 7 ring carbons. Examples of such cyclic alkyl rings include cyclopropyl, cyclobutyl, cyclopentyl, cyclohexyl or cycloheptyl.

The term "alkenyl" refers to an unsaturated branched, straight-chain or cyclic monovalent hydrocarbon radical, which has at least one carbon-carbon double bond, derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic. Heteroaromatic rings may contain 1-4 heteroatoms selected from O, N, and S. Examples include but are not limited to, radicals derived from carbazole, furan, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

The term "aryl," as used herein, refers to aromatic groups comprising a stable six-membered monocyclic, or ten-membered bicyclic or fourteen-membered tricyclic aromatic ring system which consists of carbon atoms. Examples of aryl groups include, but are not limited to, phenyl or naphthalenyl.

The term "heterocyclyl" is a 3- to 12-member saturated or partially saturated single (monocyclic), bicyclic, or fused ring system which consists of carbon atoms and from 1 to 6 heteroatoms selected from N, O and S. The heterocyclyl group may be attached at any heteroatom or carbon atom which results in the creation of a stable structure. The bicyclic heterocyclyl group includes systems where one or both rings include heteroatoms. Examples of heterocyclyl groups include, but are not limited to, 2-imidazoline, imidazolidine; morpholine, oxazoline, oxazolidine, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone, thiomorpholine, tetrahydropyran, tetrahydroquinoline, tetrahydroquinazoline, [1,2,5]thiadiazolidine 1,1-dioxide, [1,2,3] oxathiazolidine 2,2-dioxide, and the like.

The term "cis-trans isomer" refers to stereoisomeric olefins or cycloalkanes (or hetero-analogues) which differ in the positions of atoms (or groups) relative to a reference plane: in the cis-isomer the atoms of highest priority are on the same side; in the trans-isomer they are on opposite sides.

The term "substituted" refers to a radical in which one or more hydrogen atoms are each independently replaced with the same or different substituent(s).

With reference to substituents, the term "independently" means that when more than one of such substituent is possible, such substituents may be the same or different from each other.

The term "oxo" whether used alone or as part of a substituent group refers to an O=bounded to either a carbon or a sulfur atom. For example, phthalimide and saccharin are examples of compounds with oxo substituents.

It must be noted that, as used in the specification and the appended claims, the singular forms "a," "an," and "the" include plural referents unless the context clearly dictates otherwise.

Compositions
Compounds

In some embodiments, the photoactive carboxylic acid activating compound comprises a carbodiimide precursor compound of formula (I):

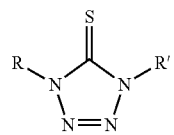

wherein
R is selected from a group comprising hydrogen, substituted or unsubstituted alkyl, substituted or unsubstituted alkenyl, and substituted or unsubstituted heterocyclyl, and R further comprises a water-solubilizing group; and
R' is substituted or unsubstituted alkyl, substituted or unsubstituted alkenyl, substituted or unsubstituted aryl, substituted or unsubstituted cycloalkyl, and substituted or unsubstituted heterocyclyl.

In other embodiments, the photoactive compound comprises a photobase generator. Some embodiments comprises a photobase generator compound of formula (II):

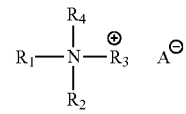

wherein

is an anion selected from the group consisting of:

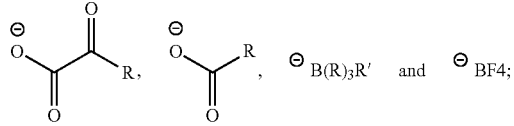

R is a substituted or unsubstituted aryl;
R' is an aryl, alkyl, alkenyl, alkoxy, cyano, —NO$_2$ or fluoro, said aryl, said alkyl, said alkenyl, and said alkoxy being optionally substituted;

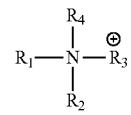

is a nitrogen-containing cation, the nitrogen-containing cation comprising a heteroaryl or heterocyclyl, said heteraryl or heterocyclyl containing one or more nitrogen atoms.

In some embodiments, the photoactive compound comprises a photobase generator compound of formula (II), wherein

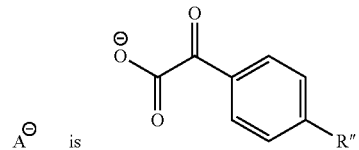

or tetraphenylborate;
R" is hydrogen or —NO$_2$;

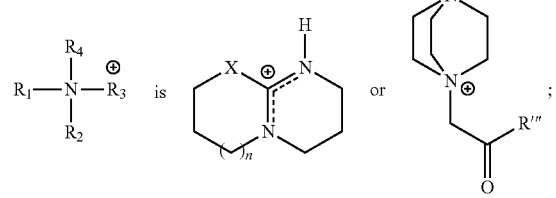

X is NH or CH$_2$;

n is an integer from 0 to 3; and

R''' is aryl or heteroaryl.

In some embodiments, the photobase generator is carbamate, O-acyloxime, ammonium salt, amineimide, α-aminoketone, amidine precursor, or aromatic urea.

In certain embodiments, the carboxylic acid activating compound, also referred to as a "coupling reagent" herein, is a carbodiimide. In some embodiments, the coupling reagent is diisopropylcarbodiimide or N-hydroxy-5-norbornene-2,3-dicarboximide. In some embodiments, the polymer is polymethyl methacrylate.

Representative photoactive carboxylic acid activating compound related to the present invention are listed in Table 1 below:

TABLE 1

Carbodiimide Precursor Compounds

| Compound # | R | R' | Name |
|---|---|---|---|
| 1 | HO—CH$_2$CH$_2$— | phenyl | 1-(hydroxymethyl)-4-phenyl-1,4-dihydro-5H-tetrazole-5-thione |
| 2 | (2,2-dimethyl-1,3-dioxolan-4-yl)methyl | (2,2-dimethyl-1,3-dioxolan-4-yl)methyl | 1,4-Bis(2,2-dimethyl-1,3-dioxolan-4-ylmethyl)-1,4-dihydro-5H-tetrazole-5-thione |
| 3 | (CH$_3$)$_2$N(CH$_2$)$_3$— | ethyl | 1-(3-(dimethylamino)propyl)-4-ethyl-1,4-dihydro-5H-tetrazole-5-thione |
| 4 | H | cyclohexyl | 1-cyclohexyl-1,4-dihydro-5H-tetrazole-5-thione |
| 5 | piperidin-1-ylmethyl | phenyl | 1-phenyl-4-(piperidin-1-ylmethyl)-1,4-dihydro-5H-tetrazole-5-thione |
| 6 | (Et)$_2$N(CH$_2$)$_3$— | 2-methoxyphenyl | 1-(3-(diethylamino)propyl)-4-(2-methoxyphenyl)-1,4-dihydro-5H-tetrazole-5-thione |
| 7 | (Et)$_2$NCH$_2$— | phenyl | 1-((diethylamino)methyl)-4-phenyl-1,4-dihydro-5H-tetrazole-5-thione |

Representative photoactive compounds related to the present invention are listed in Table 2 below:

TABLE 2

Nonionic Photobase Generator Compounds

| Compound # | Structure | Name |
|---|---|---|
| 8 | 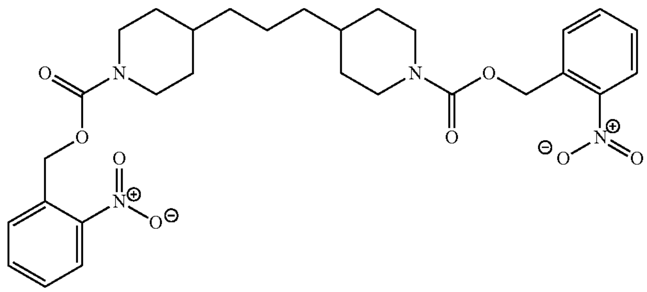 [SMILES: O=C(OCc1ccccc1[N+](=O)[O-])N1CCC(CCCC2CCN(C(=O)OCc3ccccc3[N+](=O)[O-])CC2)CC1] | 1,3-Bis[(2-nitrobenzyl)oxycarbonyl-4-piperidyl]propane |
| 9 | 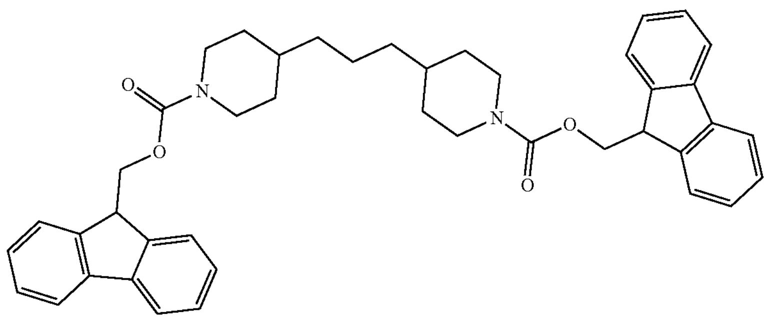 [SMILES: O=C(OCC1c2ccccc2-c2ccccc21)N1CCC(CCCC2CCN(C(=O)OCC3c4ccccc4-c4ccccc43)CC2)CC1] | 1,3-Bis[1-(9-fluorenylmethoxycarbonyl)-4-piperidyl]propane |

Representative photoactive compounds related to the present invention are listed in Table 3 below:

TABLE 3

Ionic Photobase Generator Compounds

| Compound # | R | $R_1$—$\overset{R_4}{\underset{R_2}{N}}$—$R_3$ ⊕ | Name |
|---|---|---|---|
| 10 | H | | 1,5,7-triazabicyclo[4.4.0]dec-5-enyl-phenylglyoxylate |
| 11 | $NO_2$ | | 1,5,7-triazabicyclo[4.4.0]dec-5-enyl-4-nitrophenylglyoxylate |

TABLE 3-continued

Ionic Photobase Generator Compounds

| Compound # | $R_1$—N(+)(R_4)(R_3)—R_2 | Name |
|---|---|---|
| 12 | (protonated 1,5,7-triazabicyclo[4.4.0]dec-5-ene cation) | 1,5,7-triazabicyclo[4.4.0]dec-5-enyl-tetraphenylborate |
| 13 | (protonated 1,8-diazabicyclo[5.4.0]undec-7-ene cation) | 1,8-Diazabicyclo[5.4.0]undec-7-enyl-tetraphenylborate |
| 14 | (1-phenacyl-DABCO cation) | 1-Phenacyl-(1-azonia-4-azabicyclo[2,2,2]octane)-tetraphenylborate |
| 15 | (1-naphthoylmethyl-DABCO cation) | 1-Naphthoylmethyl-(1-azonia-4-azabicyclo[2,2,2]octane)-tetraphenylborate |

Photoactive carboxylic acid activating compound related to the present invention are listed in Table 4 below:

TABLE 4

Carbodiimide Precursor Compounds

| Compound # | R | R' | Name |
|---|---|---|---|
| 16 | —(CH_2)_3N(Et)_2 | —C_6H_5 | 1-(3-(diethylamino)propyl)-4-phenyl-1,4-dihydro-5H-tetrazole-5-thione |

TABLE 4-continued

Carbodiimide Precursor Compounds

[Structure: 1,4-disubstituted tetrazole-5-thione with R and R' groups on N atoms]

| Compound # | R | R' | Name |
|---|---|---|---|
| 17 | 3-(diethylamino)propyl | 4-methoxyphenyl | 1-(3-(diethylamino)propyl)-4-(methoxyphenyl)-1,4-dihydro-5H-tetrazole-5-thione |
| 18 | 3-(diethylamino)propyl | 4-(dimethylamino)phenyl | 1-(3-(diethylamino)propyl)-4-(dimethylamino-phenyl)-1,4-dihydro-5H-tetrazole-5-thione |
| 19 | 3-(diethylamino)propyl | 4-(methylthio)phenyl | 1-(3-(diethylamino)propyl)-4-(methylthio-phenyl)-1,4-dihydro-5H-tetrazole-5-thione |
| 20 | 3-(diethylamino)propyl | 4-nitrophenyl | 1-(3-(diethylamino)propyl)-4-(nitrophenyl)-1,4-dihydro-5H-tetrazole-5-thione |
| 21 | 3-(diethylamino)propyl | 4-ethoxyphenyl | 1-(3-(diethylamino)propyl)-4-(ethoxyphenyl)-1,4-dihydro-5H-tetrazole-5-thione |
| 22 | 3-(diethylamino)propyl | [1,1'-biphenyl]-4-yl | 1-([1,1'-biphenyl]-4-yl)-4-(3-(diethylamino)propyl)-1,4-dihydro-5H-tetrazole-5-thione |
| 23 | 3-(diethylamino)propyl | 4-methoxynaphthalen-1-yl | 1-(3-(diethylamino)propyl)-4-(4-methoxynaphthalen-1-yl)-1,4-dihydro-5H-tetrazole-5-thione |
| 24[1] | 3-(diethylamino)propyl | alkyl, aryl, heteroaryl, cycloalkyl, or heterocyclyl, each substituted or unsubstituted | |
| 25 | alkyl, alkenyl and heterocyclyl, each substituted or unsubstituted and comprising a water solubilizing group | alkyl, alkenyl, cycloalkyl, heterocyclyl and aryl, e.g. phenyl, biphenyl, naphthyl, each substituted or unsubstituted | |

[1] commercially available

Synthesis

This application provides methods of making the disclosed compounds according to traditional organic synthetic methods as well as matrix or combinatorial synthetic methods. Scheme 1 describe suggested synthetic routes. Using the scheme, the guidelines below, and the examples, a person of skill in the art may develop analogous or similar methods for a given compound that is within the invention. These methods are representative of the synthetic schemes, but are not to be construed as limiting the scope of the invention.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by techniques such as preparative chromatography. The compounds may be prepared in racemic form or as individual enantiomers or diastereomers by either stereospecific synthesis or by resolution. The compounds may, for example, be resolved into their component enantiomers or diastereomers by techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Scheme 1 and Examples 1 through 12. Compounds analogous to the target compounds of these examples can be made according to similar routes. The disclosed compounds are useful in the manufacture of microarrays as described herein.

General Guidance

Scheme 1

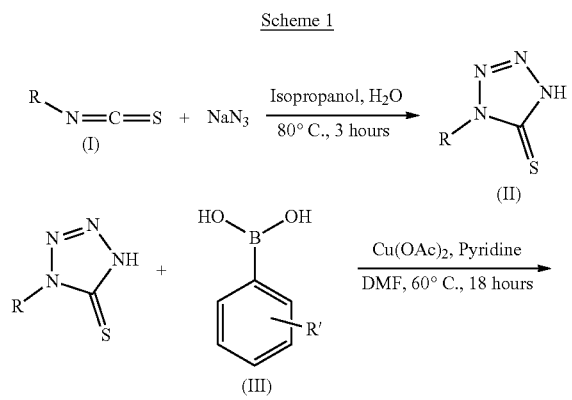

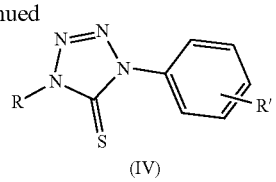

(IV)

The compound (I), wherein R is hydroxymethyl, 2,2-dimethyl-1,3-dioxolan-4-ylmethyl, piperidin-1-ylmethyl, hydrogen, 2,2-dimethyl-1,3-dioxolan-4-yl, piperidin-1-ylmethyl, 3-(diethylamino)propyl, alkyl, aryl, heterocyclyl, cycloalkyl or as defined in the above formula (I), can be synthesized as outlined by the general synthetic route illustrated in Scheme 1. Treatment of an appropriate isothiocyanate (I) with sodium azide, an known compound prepared by known methods in water solution of isopropanol at 800 Celsius for 3 hours yields the R-substituted 1-hydro-5H-tetrazole-5-thione (II) following a 1,3 dipolar cycloaddition. Copper mediated cross-coupling of the R-substituted 1-hydro-5H-tetrazole-5-thione (II) with phenylboronic acid (III) in the presence of copper acetate, pyridine and dimethylformamide (DMF) at a temperature of 60° Celsius for 18 hours yields compound (IV).

Scheme 1 provides a 70% yield of compound (II) and 33% yield of compound (IV) when R is diethylaminopropyl. The amine of compound (IV) is protonated in the presence of hydrochloride in methanol according to:

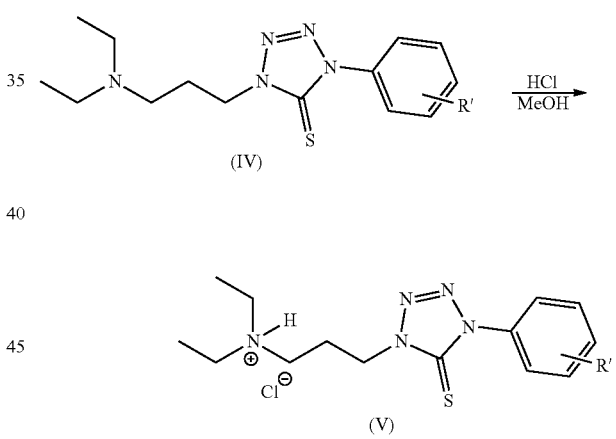

Scheme 2 provides the general scheme of photoactivated carbodiimide formation, e.g. photoinduced formation of hydroxymethyl-phenyl-carbodiimide or 1,3-Bis(2,2-dimethyl-1,3-dioxolan-4-ylmethyl)-carbodiimide.

Scheme 2

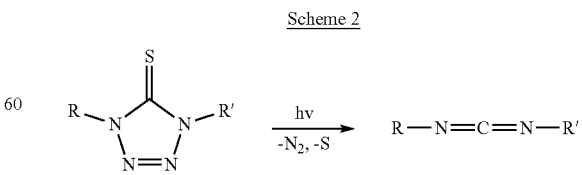

Scheme 3 provides the general scheme of photoactivated base formation, e.g. 1,3-di(piperidin-4-yl)propane, from a non-ionic photobase generator compounds.

Scheme 3

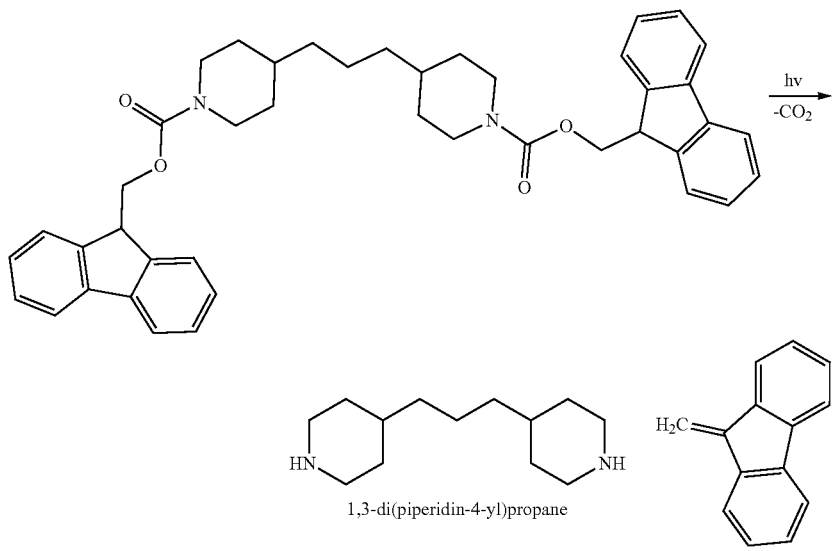

1,3-di(piperidin-4-yl)propane

Formulations

Disclosed herein are formulations such as photoactive coupling formulations and linker formulations. These formulations can be useful in the manufacture and/or use of, e.g., substrates and/or peptide arrays disclosed herein. Generally the components of each formulation disclosed herein are soluble in water at room temperature (app. 25° C.).

Photoactive Coupling Formulations

Disclosed herein are photoactive coupling formulations. In some embodiments, a photoactive coupling formulation can include components such as a solvent, a coupling reagent, a coupling molecule, a photoactive compound, and a polymer. In some embodiments, photoactive coupling formulations are shown in Table 5.

In one aspect, a photoactive coupling formulation can include a photoactive compound. Photoactive compounds may include photobase or photoacid generators. Exposure of the photoactive compounds to electromagnetic radiation is a primary photochemical event that produces a compound that goes on to induce material transforming secondary reactions within a diffusion-limited radius. A photoactive coupling formulation may comprise a photoactive compound comprising a radiation-sensitive catalyst precursor, e.g., a photoacid generator (PAG); a plurality of chemical groups that can react by elimination, addition, or rearrangement in the presence of catalyst; and optional additives to improve performance or processability, e.g., surfactants, photosensitizers, and etch resistors.

In some embodiments, a photoactive coupling formulation includes a photobase generator and a photo sensitizer in a polymer matrix dispersed in a solvent. In some embodiments, the polymer in the composition of the photoresist is generally inert and non-crosslinking but the photoactive compounds will readily generate sufficient quantities of photobase upon exposure to electromagnetic radiation to bring about a desired reaction to produce a product at acceptable yield.

In some embodiments, a photoactive coupling formulation can include various components such as a photosensitizer, a photoactive compound, a polymer, and a solvent. Specific examples of photoactive coupling formulations are shown in Table 5.

In some embodiments, a photoactive compound can be a photoacid generator (PAG) or a photobase generator (PBG). Photoacid generators (or PAGs) are cationic photoinitiators. A photoinitiator is a compound especially added to a formulation to convert absorbed light energy, UV or visible light, into chemical energy in the form of initiating species, e.g., free radicals or cations. Cationic photoinitiators are used extensively in optical lithography. The ability of some types of cationic photo initiators to serve as latent photochemical sources of very strong protonic or Lewis acids is generally the basis for their use in photo imaging applications. In some embodiments, a photoacid generator is an iodonium salt, a polonium salt, or a sulfonium salt. In some embodiments, a photoacid generator is (4-Methoxyphenyl) phenyliodonium or trifluoromethanesulfonate. In some embodiments, a photoacid generator is (2,4-dihydroxyphenyl)dimethylsulfonium triflate or (4 methoxyphenyl)dimethylsulfonium triflate, shown below:

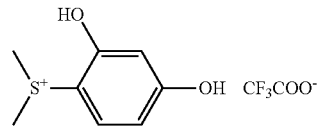

In some embodiments, a photoacid generator is iodonium and sulfonium salts of triflates, phosphates and/or antimonates. In some embodiments, a photoacid generator is about 0.5-5% by weight of the total formulation concentration. In some embodiments, a photoacid generator is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a photobase generator is 1,3-Bis [(2-nitrobenzyl)oxycarbonyl-4-piperidyl]propane or 1,3-Bis [(1-(9-fluorenylmethoxycarbonyl)-4-piperidyl]propane. The photobase generator should be present in a composition of the invention in an amount sufficient to enable deprotection of the monomer so that they are available for binding to the substrate. In some embodiments, a photobase generator is about 0.5-5% by weight of the total formulation concentration. In some embodiments, a photobase generator is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a polymer is a non-crosslinking inert polymer. In some embodiments, a polymer is a polyvinyl pyrrolidone. The general structure of polyvinyl pyrrolidone is as follows, where n is any positive integer greater than 1:

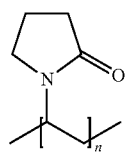

In some embodiments, a polymer is a polymer of vinyl pyrrolidone. In some embodiments, a polymer is polyvinyl pyrrollidone. Poly vinyl pyrrollidone is soluble in water and other polar solvents. When dry it is a light flaky powder, which generally readily absorbs up to 40% of its weight in atmospheric water. In solution, it has excellent wetting properties and readily forms films. In some embodiments, a polymer is a vinyl pyrrolidone or a vinyl alcohol. In some embodiments, a polymer is a polymethyl methacrylate.

In some embodiments, a polymer is 2.5-5% by weight of the total formulation concentration. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a solvent is water, ethyl lactate, n methyl pyrrollidone or a combination thereof. In some embodiments, ethyl lactate can be dissolved in water to more than 50% to form a solvent. In some embodiments, a solvent can be about 10% propylene glycol methyl ether acetate (PGMEA) and about 90% DI water. In some embodiments, a solvent can include up to about 20% PGMEA. In some embodiments, a solvent can include 50% ethyl lactate and 50% n methyl pyrrollidone. In some embodiments, a solvent is n methyl pyrrollidone. In some embodiments, a solvent is water, an organic solvent, or combination thereof. In some embodiments, the organic solvent is N Methyl pyrrolidone, di methyl formamide or combinations thereof.

In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

The photoactive coupling formulation comprises coupling molecules. The coupling molecules can include amino acids. In some instances all peptides on an array described herein are composed of naturally occurring amino acids. In others, peptides on an array described herein can be composed of a combination of naturally occurring amino acids and non-naturally occurring amino acids. In other cases, peptides on an array can be composed solely from non-naturally occurring amino acids. Non-naturally occurring amino acids include peptidomimetics as well as D-amino acids. The R group can be found on a natural amino acid or a group that is similar in size to a natural amino acid R group. Additionally, unnatural amino acids, such as beta-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, omithine, penicillamine, pyroglutamic acid, sarcosine, and thienylalanine can also be incorporated. These and other natural and unnatural amino acids are available from, for example, EMD Biosciences, Inc., San Diego, Calif. In some embodiments, a coupling molecule comprises a naturally occurring or artificial amino acid or polypeptide. Examples of coupling molecules include Boc-Glycine-OH and Boc-Histidine-OH. In some embodiments, the artificial amino acid is a D-amino acid. In some embodiments, a coupling molecule is 1-2% by weight of the total formulation concentration. In some embodiments, a coupling molecule is about 0.5-5% by weight of the total formulation concentration. In some embodiments, a coupling molecule is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration. In some embodiments, a coupling molecule comprises a protected group, e.g., a group protected via t-Boc or F-Moc chemistry. In most instances, increasing the concentration of a coupling molecule provides the best performance.

In some embodiments, a coupling reagent is carbodiimide or triazole. In some embodiments, a coupling reagent is N-Hydroxysuccinimide (NHS). In some embodiments, a coupling reagent is 2-4% by weight of the total formulation concentration. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In any of the combinations above, the formulation can be completely water strippable. Thus, in some embodiments, water can be used to wash away the photoactive coupling formulation after exposure.

Carboxylic Acid Activating Formulations

Disclosed herein are activating formulations for activating carboxylic acid so that it reacts with a free amino group of a biomolecule, e.g., an amino acid, peptide, or polypeptide. An activating formulation can include components such as a carboxylic acid group activating compound and a solvent. In some embodiments, the carboxylic acid group activating compound is a carbodiimide or a carbodiimide precursor. In some embodiments, the carbodiimide is 1-ethyl-3-(3-dimethylaminopropyl) carbodiimide. In some embodiments, the carboxylic acid group activating compound is N-Hydroxysuccinimide (NHS). In some embodiments, the carboxylic acid group activating compound is selected from: 1-Ethyl-3-(3-dimethylaminopropyl)carbodiimide [EDC], N-hydroxysuccinimide [NHS], 1,3-Diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], and N,N-Diisopropylethylamine [DIEA]. In some embodiments, the solvent is water. In some embodiments, the solvent is N-methylpyrrolidone (NMP). In some embodiments, the carboxylic acid group activating compound converts the carboxylic acid to a carbonyl group (i.e., carboxylic acid group activation). In some embodiments, the carboxylic acid group is activated for 5, 10, 15, 20, 30, 45, or 60 minutes after exposure to an activation formulation.

In some embodiments, the activating formulation comprises 4% by weight of 1-ethyl-3-(3-dimethylaminopropyl) carbodiimide and 2% by weight of N-hydroxysuccinimide (NHS) dissolved in deionized water. In some embodiments, the activating formulation comprises 4% by weight of 1,3-Diisopropylcarbodiimide (DIC) and 2% by weight of hydroxybenzotriazole (HOBt) dissolved in NMP. In some embodiments, the activating formulation comprises 4% by weight of (O-(7-azabenzotriazol-1-yl)-N,N,N',N'-tetramethyluronium hexafluorophosphate) (HATU) and 2% by weight of N,N-Diisopropylethylamine (DIEA) dissolved in NMP. In some embodiments, the activating formulation comprises 4% by weight of Benzotriazol-1-yl-oxytripyrrolidinophosphonium hexafluorophosphate (PyBOP) and 2% by weight of DIEA dissolved in NMP.

In some embodiments, the carboxylic acid group activating compound is a carbodiimide precursor. In one aspect, the carbodiimide precursor is converted to a carbodiimide through exposure to radiation, e.g., ultraviolet radiation. In one embodiment, the carbodiimide precursor is a thione. The carbodiimide precursor can also be referred to as a photoactivated carbodiimide. In one embodiment, photoactivated carbodiimides are used to provide site-specific activation of carboxylic acid groups on an array by spatially controlling exposure of the photoactivated carbodiimide solution to electromagnetic radiation at a preferred activation wavelength. In some embodiments, the preferred activation wavelength is 248 nm.

In one embodiment, the carbodiimide precursor is a thione that is converted to carbodiimide via photoactivation. In one aspect, the thione is converted to a hydroxymethyl phenyl carbodiimide after exposure to electromagnetic radiation. In some embodiments, the thione is 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, 1,4-Bis(2,2-dimethyl-1,3-dioxolan-4-ylmethyl)-1,4-dihydro-5H-tetrazole-5-thione, 4-cyclohexyl-1H-tetrazole-5(4H)-thione, or 1-phenyl-4-(piperidinomethyl)tetrazole-5(4H)-thione, and others as shown in Tables 1 and 4.

In some embodiments, the activating solution comprises a carbodiimide precursor, a solvent, and a polymer. In one embodiment, the carbodiimide precursor is 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, or 1,4-Bis(2,2-dimethyl-1,3-dioxolan-4-ylmethyl)-1,4-dihydro-5H-tetrazole-5-thione. In some embodiments, the carbodiimide precursor is present in the activation solution at a concentration of 2.5% by weight. In some embodiments the carbodiimide precursor is present in the activation solution at a concentration of 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or 5.0% by weight of the total formulation concentration.

In some embodiments, the solvent is water. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

In some embodiments, a coupling reagent is a carbodiimide. In some embodiments, a coupling reagent is a triazole. In some embodiments, a coupling reagent is 1-ethyl-3-(3-dimethylaminopropyl) carbodiimide. In some embodiments, a coupling reagent is about 0.5-5% by weight of the total formulation concentration. In some embodiments, a coupling reagent is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

Linker Formulations

Also disclosed herein is a linker formulation. A linker formulation can include components such as a solvent, a polymer, a linker molecule, and a coupling reagent. In some embodiments, the polymer is 1% by weight polyvinyl alcohol and 2.5% by weight poly vinyl pyrrollidone, the linker molecule is 1.25% by weight polyethylene oxide, the coupling reagent is 1% by weight 1-ethyl-3-(3-dimethylaminopropyl) carbodiimide, and the solvent includes water. In some embodiments, the polymer is 0.5-5% by weight polyvinyl alcohol and 0.5-5% by weight poly vinyl pyrrollidone, the linker molecule is 0.5-5% by weight polyethylene oxide, the coupling reagent is 0.5-5% by weight 1-ethyl-3-(3-dimethylaminopropyl) carbodiimide, and the solvent includes water.

In some embodiments, the solvent is water, an organic solvent, or a combination thereof. In some embodiments, the organic solvent is N methyl pyrrolidone, dimethyl formamide, dichloromethane, dimethyl sulfoxide, or a combination thereof. In some embodiments, the solvent is about 80-90% by weight of the total formulation concentration. In some embodiments, the solvent is about less than 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or greater than 99% by weight of the total formulation concentration.

In some embodiments, a polymer is a polyvinyl pyrrolidone and/or a polyvinyl alcohol. The general structure of polyvinyl alcohol is as follows, where n is any positive integer greater than 1:

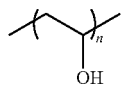

In some embodiments, a polymer is about 0.5-5% by weight of the total formulation concentration. In some embodiments, a polymer is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

A linker molecule can be a molecule inserted between a surface disclosed herein and peptide that is being synthesized via a coupling molecule. A linker molecule does not necessarily convey functionality to the resulting peptide, such as molecular recognition functionality, but can instead elongate the distance between the surface and the peptide to enhance the exposure of the peptide's functionality region(s) on the surface. In some embodiments, a linker can be about 4 to about 40 atoms long to provide exposure. The linker molecules can be, for example, aryl acetylene, ethylene glycol oligomers containing 2-10 monomer units (PEGs), diamines, diacids, amino acids, and combinations thereof. Examples of diamines include ethylene diamine and diamino propane. Alternatively, linkers can be the same molecule type as that being synthesized (e.g., nascent polymers or various coupling molecules), such as polypeptides and polymers of amino acid derivatives such as for example, amino hexanoic acids. In some embodiments, a linker molecule is a molecule having a carboxylic group at a first end of the molecule and a protecting group at a second end of the molecule. In some embodiments, the protecting group is a t-Boc protecting group or an Fmoc protecting group. In some embodiments, a linker molecule is or includes an aryl acetylene, a polyethyleneglycol, a nascent polypeptide, a diamine, a diacid, a peptide, or combinations thereof. In some embodiments, a linker molecule is about 0.5-5% by weight of the total formulation concentration. In some embodiments, a linker molecule is about less than 0.1, 0.1, 0.2, 0.3, 0.4, 0.5, 0.6, 0.7, 0.8, 0.9, 1.0, 1.1, 1.2, 1.3., 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, or greater than 5.0% by weight of the total formulation concentration.

The unbound (or free end) portion of a linker molecule can have a reactive functional group which is blocked, protected, or otherwise made unavailable for reaction by a removable protecting group. The protecting group can be bound to a linker molecule to protect a reactive functionality on the linker molecule. Protecting groups that can be used include all acid- and base-labile protecting groups. For example, linker amine groups can be protected by t-butoxycarbonyl (t-BOC or BOC) or benzyloxycarbonyl (CBZ), both of which are acid labile, or by 9-fluorenylmethoxycarbonyl (FMOC), which is base labile.

Additional protecting groups that can be used include acid-labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha,alpha-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9 fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio) carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid-labile groups for protecting carboxylic acids: tert-butyl ester; acid labile groups for protecting hydroxyl groups: dimethyltrityl. See also, Greene, T. W., Protective Groups in Organic Synthesis, Wiley-Interscience, NY, (1981).

Photobase Generator Compositions

Disclosed herein are photobase generator compositions. Photobase generator compositions can be used to deprotect an Fmoc protected amino acid upon exposure to light, e.g., through a reticle. In some embodiments, the photobase generator comprises an amine. In some embodiments, the anion is a borate. In some embodiments, the anion is a phenylglyoxylate. In some embodiments, the amine has the formula $NR_1R_2R_3$ with $R_1$, $R_2$ and $R_3$ defined above in formula (II). In some embodiments, the photobase generator comprises an amine attached to a polymer. In some embodiments, the amine is bound to a counter ion. In one embodiment, the counter ion is a carboxylate. In one aspect, the carboxylate undergoes photodecarboxylation upon exposure to radiation. In some embodiments, the counter ion is a borate. In some embodiments, the anion is a phenylglyoxylate. In some embodiments, the photobase generator comprises a chromophore attached to an amine and an anion. In some embodiments, the anion is a borate. In some embodiments, the anion is a phenylglyoxylate.

Also disclosed herein are photobase generator compositions comprising a photobase generator, a polymer, and an amino acid. In some embodiments, the amino acid is an Fmoc-protected amino acid. In some embodiments, the amino acid is present at 0.1 M in said photobase generator composition. In some embodiments, the polymer is present at 0.5-3% by weight in said photobase generator composition. In some embodiments, the polymer is polymethyl methacrylate.

Substrates

Also disclosed herein are substrates. In some embodiments a substrate surface is planar (i.e., 2-dimensional). In some embodiments a substrate surface is functionalized with free carboxylic acid groups. In some embodiments, a substrate surface is functionalized with free amine groups. A surface that is functionalized with free amine groups can be converted to free carboxylic acid groups by reacting with activating the carboxylic acid groups of a molecule comprising at least two free carboxylic acid groups (e.g., converting the carboxylic acid group to a carbonyl group using carbodiimide) and reacting the molecule with the free amine groups attached to the surface of the substrate. In some embodiments, the molecule comprising multiple carboxylic acid groups is succinic anhydride, polyethylene glycol diacid, benzene-1,3,5-tricarboxylic acid, benzenehexacarboxylic acid, or carboxymethyl dextran.

In some embodiments, a substrate can include a porous layer (i.e., a 3-dimensional layer) comprising functional groups for binding a first monomer building block. In some embodiments, a substrate surface comprises pillars for peptide attachment or synthesis. In some embodiments, a porous layer is added to the top of the pillars.

Porous Layer Substrates

Porous layers that can be used are flat, permeable, polymeric materials of porous structure that have a carboxylic acid functional group (that is native to the constituent polymer or that is introduced to the porous layer) for attachment of the first peptide building block. For example, a porous layer can be comprised of porous silicon with functional groups for attachment of a polymer building block attached to the surface of the porous silicon. In another example, a porous layer can comprise a cross-linked polymeric material. In some embodiments, the porous layer can employ polystyrenes, saccharose, dextrans, polyacryloylmorpholine, polyacrylates, polymethylacrylates, polyacrylamides, polyacrylolpyrrolidone, polyvinylacetates, polyethyleneglycol, agaroses, sepharose, other conventional chromatography type materials and derivatives and mixtures thereof. In some embodiments, the porous layer building material is selected from: poly(vinyl alcohol), dextran, sodium alginate, poly(aspartic acid), poly(ethylene glycol), poly(ethylene oxide), poly(vinyl pyrrolidone), poly(acrylic acid), poly(acrylic acid)-sodium salt, poly(acrylamide), poly (N-isopropyl acrylamide), poly(hydroxyethyl acrylate), poly (acrylic acid), poly(sodium styrene sulfonate), poly(2-acrylamido-2-methyl-1-propanesulfonic acid), polysaccharides, and cellulose derivatives. Preferably the porous layer has a porosity of 10-80%. In one embodiment, the thickness of the porous layer ranges from 0.01 m to about 1,000 µm. Pore sizes included in the porous layer may range from 2 nm to about 100 µm.

According to another embodiment of the present invention there is provided a substrate comprising a porous polymeric material having a porosity from 10-80%, wherein reactive groups are chemically bound to the pore surfaces and are adapted in use to interact, e.g. by binding chemically, with a reactive species, e.g., deprotected monomeric building blocks or polymeric chains. In one embodiment the reactive group is a carboxylic acid group. The carboxylic acid group is free to bind, for example, an unprotected amine group of a peptide or polypeptide.

In an embodiment, the porous layer is in contact with a support layer. The support layer comprises, for example, metal, plastic, silicon, silicon oxide, or silicon nitride. In another embodiment, the porous layer can be in contact with a patterned surface, such as on top of pillar substrates described below.

Pillar Substrates

In some embodiments, a substrate can include a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between about 1,000-5,000 angstroms, and wherein the plurality of pillars are present at a density of greater than about 10,000/cm$^2$.

In some embodiments, the distance between the surface of each pillar and the upper surface of the later can be between about less than 1,000, 2,000, 3,000, 3,500, 4,500, 5,000, or greater than 5,000 angstroms (or any integer in between).

In some embodiments, the surface of each pillar is parallel to the upper surface of the layer. In some embodiments, the surface of each pillar is substantially parallel to the upper surface of the layer.

In some embodiments, the plurality of pillars are present at a density of greater than 500, 1,000, 2,000, 3,000, 4,000, 5,000, 6,000, 7,000, 8,000, 9,000, 10,000, 11,000, or 12,000/cm$^2$ (or any integer in between). In some embodiments, the plurality of pillars are present at a density of greater than 10,000/cm$^2$. In some embodiments, the plurality of pillars are present at a density of about 10,000/cm$^2$ to about 2.5 million/cm$^2$ (or any integer in between). In some embodiments, the plurality of pillars are present at a density of greater than 2.5 million/cm$^2$.

In some embodiments, the surface area of each pillar surface is at least 1 µm$^2$. In some embodiments, the surface area of each pillar surface can be at least 0.1, 0.5, 12, 3, 4, 5, 6, 7, 8, 9, 10, 15, 20, 25, 30, 35, 40, 45, or 50 µm$^2$ (or any integer in between). In some embodiments, the surface area of each pillar surface has a total area of less than 10,000 µm$^2$. In some embodiments, the surface area of each pillar surface has a total area of less than 500, 1,000, 2,000, 3,000, 4,000, 5,000, 6,000, 7,000, 8,000, 9,000, 10,000, 11,000, or 12,000 µm$^2$ (or any integer in between).

In some embodiments, the distance between the surface of each pillar and the lower surface of the layer is 2,000-7,000 angstroms. In some embodiments, the distance between the surface of each pillar and the lower surface of the layer is about less than 500, 1,000, 2,000, 3,000, 4,000, 5,000, 6,000, 7,000, 8,000, 9,000, 10,000, 11,000, 12,000, or greater than 12,000 angstroms (or any integer in between). In some embodiments, the distance between the surface of each pillar and the lower surface of the layer is 7,000, 3,000, 4,000, 5,000, 6,000, or 7,000 angstroms (or any integer in between).

In some embodiments, the layer is 1,000-2,000 angstroms thick. In some embodiments, the layer is about less than 500, 1,000, 2,000, 3,000, 4,000, 5,000, 6,000, 7,000, 8,000, 9,000, 10,000, 11,000, 12,000, or greater than 12,000 angstroms thick (or any integer in between).

In some embodiments, the center of each pillar is at least 2,000 angstroms from the center of any other pillar. In some embodiments, the center of each pillar is at least about 500, 1,000, 2,000, 3,000, or 4,000 angstroms (or any integer in between) from the center of any other pillar. In some embodiments, the center of each pillar is at least about 2 µm to 200 µm from the center of any other pillar.

In some embodiments, the metal is chromium. In some embodiments, the metal is chromium, titanium, aluminum, tungsten, gold, silver, tin, lead, thallium, indium, or a combination thereof. In some embodiments, the layer is at least 98.5-99% (by weight) metal.

In some embodiments, the layer is 100% metal. In some embodiments, the layer is at least about greater than 90, 91, 92, 93, 94, 95, 96, 97, 98, 98.5, or 99% metal. In some embodiments, the layer is a homogenous layer of metal.

In some embodiments, at least one or each pillar comprises silicon. In some embodiments, at least one or each pillar comprises silicon dioxide or silicon nitride. In some embodiments, at least one or each pillar is at least 90, 91, 92, 93, 94, 95, 96, 97, 98, 98.5, or 99% (by weight) silicon dioxide.

In some embodiments, a substrate can include a linker molecule having a free amino terminus attached to the surface of each pillar. In some embodiments, a substrate can include a linker molecule having a free amino terminus attached to the surface of at least one pillar. In some embodiments, a substrate can include a linker molecule having a protecting group attached to the surface of each pillar. In some embodiments, a substrate can include a linker molecule having a protecting group attached to the surface of at least one pillar. In some embodiments, a substrate can include a coupling molecule attached to the surface of at least one pillar. In some embodiments, a substrate can include a coupling molecule attached to the surface of each pillar. In some embodiments, a substrate can include a polymer in contact with the surface of at least one of the pillars. In some embodiments, a substrate can include a polymer in contact with the surface of each pillar. In some embodiments, a substrate can include a gelatinous form of a polymer in contact with the surface of at least one of the pillars. In some embodiments, a substrate can include a solid form of a polymer in contact with the surface of at least one of the pillars.

In some embodiments, the surface of at least one of the pillars of the substrate is derivatized. In some embodiments, a substrate can include a polymer chain attached to the surface of at least one of the pillars. In some embodiments, the polymer chain comprises a peptide chain. In some embodiments, the attachment to the surface of the at least one pillar is via a covalent bond.

In some embodiments, the surface of each pillar is square or rectangular in shape. In some embodiments, the substrate can be coupled to a silicon dioxide layer. The silicon dioxide layer can be about 0.5 μm to 3 μm thick. In some embodiments, the substrate can be coupled to a wafer, e.g., a silicon wafer. The silicon dioxide layer can be about 700 μm to 750 μm thick.

Arrays

Also disclosed herein are arrays. In some embodiments, the surface of the array is functionalized with free carboxylic acids. In some embodiments, the free carboxylic acids are activated to bind to amine groups, e.g., during polypeptide synthesis on the surface of the array. In some embodiments, the surface density of free carboxylic acid groups on the array is greater than $10/cm^2$, $100/cm^2$, $1,000/cm^2$, $10,000/cm^2$, $100,000/cm^2$, $1,000,000/cm^2$, or $10,000,000/cm^2$.

In some embodiments, an array can be a three-dimensional array, e.g., a porous array comprising features attached to the surface of the porous array. In some embodiments, the surface of a porous array includes external surfaces and surfaces defining pore volume within the porous array. In some embodiments, a three-dimensional array can include features attached to a surface at positionally-defined locations, said features each comprising: a collection of peptide chains of determinable sequence and intended length. In one embodiment, within an individual feature, the fraction of peptide chains within said collection having the intended length is characterized by an average coupling efficiency for each coupling step of greater than 98%.

In some embodiments, the average coupling efficiency for each coupling step is at least 98.5%. In some embodiments, the average coupling efficiency for each coupling step is at least 99%. In some embodiments, the average coupling efficiency for each coupling step is at least 90, 91, 92, 93, 94, 95, 96, 97, 98, 98.5, 98.6, 98.7, 98.8, 98.9, 99.0, 99.1, 99.2, 99.3, 99.4, 99.5, 99.6, 99.7, 99.8, 99.9, or 100%.

In some embodiments, each peptide chain is from 5 to 60 amino acids in length. In some embodiments, each peptide chain is at least 5 amino acids in length. In some embodiments, each peptide chain is at least 5, 10, 15, 20, 25, 30, 35, 40, 45, 50, 55, or 60 amino acids in length. In some embodiments, each peptide chain is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each peptide chain comprises one or more L amino acids. In some embodiments, each peptide chain comprises one or more D amino acids. In some embodiments, each peptide chain comprises one or more naturally occurring amino acids. In some embodiments, each peptide chain comprises one or more synthetic amino acids.

In some embodiments, an array can include at least 1,000 different peptide chains attached to the surface. In some embodiments, an array can include at least 10,000 different peptide chains attached to the surface. In some embodiments, an array can include at least 100, 500, 1000, 2000, 3000, 4000, 5000, 6000, 7000, 8000, 9000, 10,000, or greater than 10,000 different peptide chains attached to the surface (or any integer in between).

In some embodiments, each of the positionally-defined locations is at a different, known location that is physically separated from each of the other positionally-defined locations. In some embodiments, each of the positionally-defined locations is a positionally-distinguishable location. In some embodiments, each determinable sequence is a known sequence. In some embodiments, each determinable sequence is a distinct sequence.

In some embodiments, the features are covalently attached to the surface. In some embodiments, said peptide chains are attached to the surface through a linker molecule or a coupling molecule.

In some embodiments, the features comprise a plurality of distinct, nested, overlapping peptide chains comprising subsequences derived from a source protein having a known sequence. In some embodiments, each peptide chain in the plurality is substantially the same length. In some embodiments, each peptide chain in the plurality is the same length. In some embodiments, each peptide chain in the plurality is at least 5 amino acids in length. In some embodiments, each peptide chain in the plurality is at least 5, 10, 15, 20, 25, 30, 35, 40, 45, 50, 55, or 60 amino acids in length. In some embodiments, each peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, at least one peptide chain in the plurality is at least 5 amino acids in length. In some embodiments, at least one peptide chain in the plurality is at least 5, 10, 15, 20, 25, 30, 35, 40, 45, 50, 55, or 60 amino acids in length. In some embodiments, at least one peptide chain in the plurality is less than 5, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or greater than 60 amino acids in length. In some embodiments, each polypeptide in a feature is substantially the same length. In some embodiments, each polypeptide in a feature is the same length. In some embodiments, the features comprise a plurality of peptide chains each having a random, determinable sequence of amino acids.

Methods

Methods of Manufacturing Substrates

Also disclosed herein are methods for making substrates. In some embodiments, a method of producing a substrate can include coupling a porous layer to a support layer. The support layer can comprise any metal or plastic or silicon or silicon oxide or silicon nitride. In one embodiment, the substrate comprises multiple carboxylic acid substrates attached to the substrate for binding peptides during peptide synthesis and protein coupling. In some embodiments, a method of producing a substrate can include coupling a porous layer to a plurality of pillars, wherein the porous layer comprises functional groups for attachment of a compound to the substrate, wherein the plurality of pillars are coupled to a planar layer in positionally-defined locations, wherein each pillar has a planar surface extended from the planar layer, wherein the distance between the surface of each pillar and the upper surface of the planar layer is between about 1,000-5,000 angstroms, and wherein the plurality of pillars are present at a density of greater than about $10,000/cm^2$.

In some embodiments, the surface of each pillar is parallel to the upper surface of the planar layer. In some embodiments, the surface of each pillar is substantially parallel to the upper surface of the planar layer.

In some embodiments, a method of preparing a substrate surface can include obtaining a surface comprising silicon dioxide and contacting the surface with a photoactive coupling formulation comprising a photoactive compound, a coupling molecule, a coupling reagent, a polymer, and a solvent; and applying ultraviolet light to positionally-defined locations located on the top of the surface and in contact with the photoactive formulation.

Methods of Manufacturing Arrays

Also disclosed herein are methods for manufacturing arrays. In some embodiments, the arrays disclosed herein can be synthesized in situ on a surface, e.g., a substrate disclosed herein. In some instances, the arrays are made using photolithography. For example, the substrate is contacted with a photoactive coupling solution. Masks can be used to control radiation or light exposure to specific locations on a surface provided with free linker molecules or free coupling molecules having protecting groups. In the exposed locations, the protecting groups are removed, resulting in one or more newly exposed reactive moieties on the coupling molecule or linker molecule. The desired linker or coupling molecule is then coupled to the unprotected attached molecules, e.g., at the carboxylic acid group. The process can be repeated to synthesize a large number of features in specific or positionally-defined locations on a surface (see, for example, U.S. Pat. No. 5,143,854 to Pirrung et al., U.S. Patent Application Publication Nos. 2007/0154946 (filed on Dec. 29, 2005), 2007/0122841 (filed on Nov. 30, 2005), 2007/0122842 (filed on Mar. 30, 2006), 2008/0108149 (filed on Oct. 23, 2006), and 2010/0093554 (filed on Jun. 2, 2008), each of which is herein incorporated by reference).

In some embodiments, a method of producing a three-dimensional (e.g., porous) array of features, can include obtaining a porous layer attached to a surface; and attaching the features to the porous layer, said features each comprising a collection of peptide chains of determinable sequence and intended length, wherein within an individual feature, the fraction of peptide chains within said collection having the intended length is characterized by an average coupling efficiency for each coupling step of at least about 98%. In some embodiments, the features are attached to the surface using a photoactive coupling formulation, comprising a photoactive compound, a coupling molecule, a coupling reagent, a polymer, and a solvent. In some embodiments, the features are attached to the surface using a photoactive coupling formulation disclosed herein. In some embodiments, the photoactive coupling formulation is stripped away using water.

In one embodiment, described herein is a process of manufacturing an array. A surface comprising attached carboxylic acid groups is provided. The surface is contacted with a photoactive coupling solution comprising a photoactive compound, a coupling molecule, a coupling reagent, a polymer, and a solvent. The surface is exposed to ultraviolet light in a deep ultra violet scanner tool according to a pattern defined by a photomask, wherein the locations exposed to ultraviolet light undergo photo base generation due to the presence of a photobase generator in the photoactive coupling solution. The expose energy can be from 1 mJ/cm$^2$ to 100 mJ/cm$^2$ in order to produce enough photobase.

The surface is post baked upon exposure in a post exposure bake module. Post exposure bake acts as a chemical amplification step. The baking step amplifies the initially generated photobase and also enhances the rate of diffusion to the substrate. The post bake temperature can vary between 75° C. to 115° C., depending on the thickness of the porous surface, for at least 60 seconds and not usually exceeding 120 seconds. The free carboxylic acid group is coupled to the deprotected amine group of a free peptide or polypeptide, resulting in coupling of the free peptide or polypeptide to the carboxylic acid group attached to the surface. This surface may be a porous surface. The synthesis of peptides coupled to a carboxylic acid group attached to the surface occurs in an N—C synthesis orientation, with the amine group of free peptides attaching to carboxylic acid groups bound to the surface of the substrate. Alternatively, a diamine linker may be attached to a free carboxylic acid group to orient synthesis in a C→N direction, with the carboxylic acid group of free peptides attaching to amine groups bound to the surface of the substrate.

The photoactive coupling solution can now be stripped away. In some embodiments, provided herein is a method of stripping the photoresist completely with deionized (DI) water. This process is accomplished in a developer module. The wafer is spun on a vacuum chuck for, e.g., 60 seconds to 90 seconds and deionized water is dispensed through a nozzle for about 30 seconds.

The photoactive coupling formulation can be applied to the surface in a coupling spin module. A coupling spin module can typically have 20 nozzles or more to feed the photoactive coupling formulation. These nozzles can be made to dispense the photoactive coupling formulation by means of pressurizing the cylinders that hold these solutions or by a pump that dispenses the required amount. In some embodiments, the pump is employed to dispense 5-8 cc of the photoactive coupling formulation onto the substrate. The substrate is spun on a vacuum chuck for 15-30 seconds and the photoactive coupling formulation is dispensed. The spin speed can be set to 2000 to 2500 rpm.

Optionally, a cap film solution coat is applied on the surface to prevent the unreacted amino groups on the substrate from reacting with the next coupling molecule. The cap film coat solution can be prepared as follows: a solvent, a polymer, and a coupling molecule. The solvent that can be used can be an organic solvent like N methyl pyrrolidone, dimethyl formamide, or combinations thereof. The capping molecule is typically acetic anhydride and the polymer can be polyvinyl pyrrolidone, polyvinyl alcohol, polymethyl methacrylate, poly (methyl iso propenyl) ketone, or poly (2 methyl pentene 1 sulfone). In some embodiments, the capping molecule is ethanolamine.

This process is done in a capping spin module. A capping spin module can include one nozzle that can be made to dispense the cap film coat solution onto the substrate. This solution can be dispensed through pressurizing the cylinder that stores the cap film coat solution or through a pump that precisely dispenses the required amount. In some embodiments, a pump is used to dispense around 5-8 cc of the cap coat solution onto the substrate. The substrate is spun on a vacuum chuck for 15-30 s and the coupling formulation is dispensed. The spin speed can be set to 2000 to 2500 rpm.

The substrates with the capping solution are baked in a cap bake module. A capping bake module is a hot plate set up specifically to receive wafers just after the capping film coat is applied. In some embodiments, provided herein is a method of baking the spin coated capping coat solution in a hot plate to accelerate the capping reaction significantly. Hot plate baking generally reduces the capping time for amino acids to less than two minutes.

The byproducts of the capping reaction are stripped in a stripper module. A stripper module can include several nozzles, typically up to 10, set up to dispense organic solvents such as acetone, iso propyl alcohol, N methyl pyrrolidone, dimethyl formamide, DI water, etc. In some embodiments, the nozzles can be designated for acetone followed by iso propyl alcohol to be dispensed onto the spinning wafer. The spin speed is set to be 2000 to 2500 rpm for around 20 s.

This entire cycle can be repeated as desired with different coupling molecules each time to obtain a desired sequence.

In some embodiments, an array comprising a surface of free carboxylic acids is used to synthesize polypeptides in an N—C orientation. In one embodiment, the carboxylic acids on the surface of the substrate are activated (e.g., converted to a carbonyl) to allow them to bind to free amine groups on an amino acid. In one embodiment, activation of carboxylic acids on the group of the surface can be done by addition of a solution comprising a carbodiimide or succinimide to the surface of the array. In some embodiments, carboxylic acids can be activated by addition of a solution comprising 1-ethyl-3-(3-dimethylaminopropyl)carbodiimide [EDC], N-hydroxysuccinimide [NHS], 1,3-diisopropylcarbodiimide [DIC], hydroxybenzotriazole (HOBt), (O-(7-azabenzotriazol-1-yl)-N,N,N',N'-tetramethyluronium hexafluorophosphate) [HATU], benzotriazol-1-yl-oxytripyrrolidinophosphonium hexafluorophosphate [PyBOP], or N,N-diisopropylethylamine [DIEA] to the surface of the array. The activation solution is washed away and the surface of the array is prepared for addition of an amino acid layer (i.e., one amino acid at each activated carboxylic acid group). Carboxylic acid groups remain activated for up to 2, 3, 4, 5, 6, 7, 8, 9, or 10 hours.

Addition of a solution comprising an amino acid with a free amine group to the activated carboxylic acid surface of the array results in binding of a single amino acid to each carboxylic acid group. In some embodiments, the amino acid comprises an amino acid with protected amine groups. Using a photosensitive chemical reaction, the protecting group can be removed from the amine group of selected amino acids at site-specific locations using a reticle. For example, Fmoc-protected amino acids are mixed in a solution comprising a photobase generator. Upon exposure of the solution on the array to a specific frequency of light at site-specific locations, the photobase generator will release a base which will deprotect the amino acid, resulting in coupling of the amino acid to the activated carboxylic acid group on the surface of the array. Another method involves using a protected base that is then unprotected by a photoacid released by a photoacid generator upon light exposure. In some embodiments, the protected base is N-Boc-piperidine or 1,4-bis(N-Boc)-piperazine.

After a completed layer of amino acids is coupled, remaining uncoupled activated carboxylic acids are capped to prevent nonspecific binding of amino acids on subsequent synthesis steps. The steps of activation, addition of an amino acid layer, and capping are repeated as necessary to synthesize the desired polypeptides at specific locations on the array.

In one embodiment, peptides synthesized in the N—C terminus direction can be capped with a diamine molecule to enhance binding properties of selected polypeptide sequences to a biological molecule, e.g., an antibody. In other embodiments, peptides synthesized in the C→N direction can be capped with a dicarboxylic acid molecule to enhance binding properties of selected sequences to a biological molecule.

While synthesizing polypeptides in parallel on the surface of an array, the method described herein ensures complete activation of carboxylic acid on the surface of the array. Due to stability of the activated ester for an extended period of time, 2, 3, 4, 5, 6, 7, 8, 9, 10, 11, 12, 13, 14, 15, 16, 17, 18, 19, 20, 21, 22, 23, 24, 25 or more coupling cycles may be completed after a single activation step (e.g., to couple an entire layer of 2-25 or more different amino acids at different locations on the array). As the coupling occurs during hard bake (heating in a hot plate at 85-90° Celsius for 90 seconds immediately after coating) and due to the presence of excess amino acid in the solution, complete 100% deprotection of Fmoc-protected amino acid may not be required for significantly high coupling yields. After addition of all amino acids and capping, all free activated carboxylic acids are either coupled or capped, thus resulting in high efficiency and accuracy of polypeptide synthesis.

Methods of Use of Peptide Arrays

Also disclosed herein are methods of using substrates, formulations, and/or arrays. Uses of the arrays disclosed herein can include research applications, therapeutic purposes, medical diagnostics, and/or stratifying one or more patients.

Any of the arrays described herein can be used as a research tool or in a research application. In one aspect, arrays can be used for high throughput screening assays. For example, enzyme substrates (i.e., peptides on a peptide array described herein) can be tested by subjecting the array to an enzyme and identifying the presence or absence of enzyme substrate(s) on the array, e.g., by detecting at least one change among the features of the array.

Arrays can also be used in screening assays for ligand binding, to determine substrate specificity, or for the identification of peptides that inhibit or activate proteins. Labeling techniques, protease assays, as well as binding assays useful for carrying out these methodologies are generally well-known to one of skill in the art.

In some embodiments, an array can be used to represent a known protein sequence as a sequence of overlapping peptides. For example, the amino acid sequence of a known protein is divided into overlapping sequence segments of any length and of any suitable overlapping frame, and peptides corresponding to the respective sequence segments are in-situ synthesized as disclosed herein. The individual peptide segments so synthesized can be arranged starting from the amino terminus of the known protein.

In some embodiments, an array is used in a method wherein the antigenic representation of the array includes at least one region where the whole antigen sequence of a known protein is spanned via epitope sliding; the immunoactive regions of the antigen are determined by contacting one or more clinical samples on the array or a plurality of different arrays, and the set of peptide sequences required to represent the known protein antigen are reduced.

In some embodiments, a sample is applied to an array having a plurality of random peptides. The random peptides can be screened and BLASTed to determine homologous domains with, e.g., a 90% or more identity to a given antigenic sequence. In some aspect, the whole antigenic sequence can then be synthesized and used to identify potential markers and/or causes of a disease of interest.

In some embodiments, an array is used for high throughput screening of one or more genetic factors. Proteins associated with a gene can be a potential antigen and antibodies against these proteins can be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragment of antibodies, antibody like molecules or antibodies. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In another aspect, an array can be used to identify drug candidates for therapeutic use. For example, when one or more epitopes for specific antibodies are determined by an assay (e.g., a binding assay such as an ELISA), the epitopes can be used to develop a drug (e.g., a monoclonal neutralizing antibody) to target antibodies in disease.

In one aspect, also provided are arrays for use in medical diagnostics. An array can be used to determine a response to administration of drugs or vaccines. For example, an individual's response to a vaccine can be determined by detecting the antibody level of the individual by using an array with peptides representing epitopes recognized by the antibodies produced by the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a protein of interest (e.g., an antibody) in a sample can include obtaining an array disclosed herein and contacted with a sample suspected of comprising the protein of interest; and determining whether the protein of interest is present in the sample by detecting the presence or absence of binding to one or more features of the array. In some embodiments, the protein of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining an array disclosed herein contacted with a sample derived from a subject previously administered the vaccine candidate, wherein the sample comprises a plurality of antibodies; and determining the binding specificity of the plurality of antibodies to one or more features of the array. In some embodiments, the features comprise a plurality of distinct, nested, overlapping peptide chains comprising subsequences derived from a source protein having a known sequence.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); Methods In Enzymology (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* 3$^{rd}$ *Ed.* (Plenum Press) Vols A and B (1992).

COMPOUND EXAMPLES

Example 1

1-(diethylamino-methyl)-4-phenyl-1,4-dihydro-5H-tetrazole-5-thione

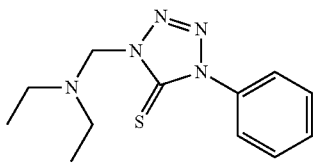 [SMILES: CCN(CC)Cn1nnn(-c2ccccc2)c1=S]

1-(diethylamino-methyl)-4-phenyl-1,4-dihydro-5H-tetrazole-5-thione is commercially available from Sigma Aldrich.

Example 2

1-(3-(diethylamino)-propyl)-4-(2-methoxyphenyl)-1,4-dihydro-5H-tetrazole-5-thione

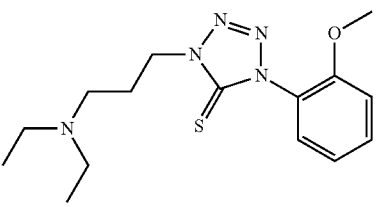 [SMILES: CCN(CC)CCCn1nnn(-c2ccccc2OC)c1=S]

1-(3-(diethylamino)-propyl)-4-(2-methoxyphenyl)-1,4-dihydro-5H-tetrazole-5-thione was prepared according to Scheme 1.

$^1$H NMR (400 MHz, CDCl3): 7.47-7.38 (m, 2H), 7.01-6.95 (m, 2H), 4.43 (t, 2H), 3.83 (s, 3H), 2.62-2.54 (m, 6H), 2.14-2.11 (m, 2H), 1.07-1.04 (t, 6H). MS, m/z, calculated for $C_{15}H_{23}N_5OS$ [MH$^+$] 322.44, observed 322.

Example 3

1,3-Bis [(2-nitrobenzyl)oxycarbonyl-4-piperidyl]propane

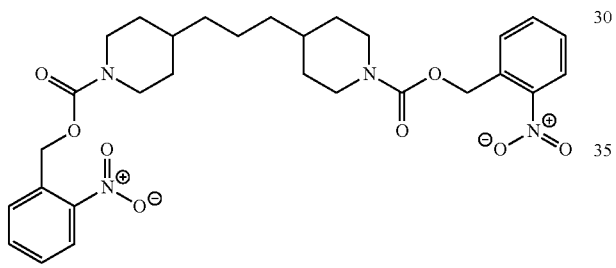

1,3-Bis[(2-nitrobenzyl)oxycarbonyl-4-piperidyl]propane is commercially available from Sigma Aldrich.

Example 4

1,3-Bis [1-(9-fluorenylmethoxycarbonyl)-4-piperidyl]propane

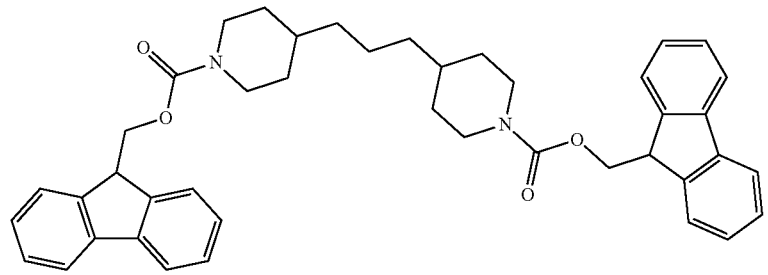 [SMILES: O=C(OCC1c2ccccc2-c2ccccc21)N1CCC(CCCC2CCN(C(=O)OCC3c4ccccc4-c4ccccc43)CC2)CC1]

1,3-Bis[1-(9-fluorenylmethoxycarbonyl)-4-piperidyl]propane is commercially available from Sigma Aldrich.

Example 5

1-Phenacyl-(1-azonia-4-azabicyclo[2,2,2]octane) bromide

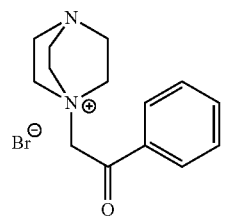 [SMILES: [Br-] ; O=C(C[N+]12CCN(CC1)CC2)c1ccccc1]

To a solution of the 2-bromoacetophenone in toluene one equivalent of ethereal solution of 1,4-diazabicyclo[2.2.2]octane was added at room temperature. The reaction mixture was stirred at room temperature for one hour. The precipitated bromide was filtered, washed with diethyl ether thrice and dried to give the title compound in 91% yield.

$^1$H NMR (400 MHz, D$_2$O): 7.88 (d, 2H, ArH), 7.67 (t, 1H, ArH), 7.50 (t, 2H, ArH), 4.70 (s, 2H, CH$_2$), 3.70 (t, 6H, NCH$_2$), 3.20 (t, 6H, NCH$_2$).

Example 6

1-Phenacyl-(1-azonia-4-azabicyclo[2,2,2]octane) tetraphenylborate

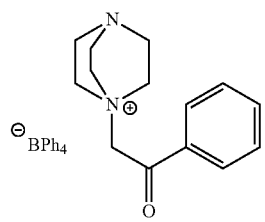 [SMILES: O=C(C[N+]12CCN(CC1)CC2)c1ccccc1 ; "BPh4"]

To an aqueous solution of the 1-phenacyl-(1-azonia-4-azabicyclo[2,2,2]octane) bromide one equivalent of an aqueous solution of sodium tetraphenylborate was added. The reaction mixture was stirred for one hour. The solid was filtered, washed with water, ether and dried to give the title compound in 40% yield.

$^1$H NMR (400 MHz, DMSO-d$_6$): 8.00 (d, 2H, ArH), 7.75 (t, 1H, ArH), 7.62 (t, 2H, ArH), 7.18-7.16 (br s, 8H, ArH), 6.92 (t, 8H, ArH), 6.79 (t, 4H, ArH), 4.70 (s, 2H, CH₂), 3.58 (t, 6H, NCH₂), 3.12 (t, 6H, NCH₂).

Example 7

1-Naphthoylmethyl-(1-azonia-4-azabicyclo[2,2,2]octane) bromide

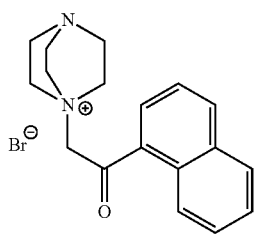 [SMILES: [Br-] ; O=C(C[N+]12CCN(CC1)CC2)c1cccc2ccccc12]

To a solution of the 2-bromo-2'-acetonaphthone in toluene one equivalent of ethereal solution of 1,4-diazabicyclo[2.2.2]octane was added at room temperature. The reaction mixture was stirred at room temperature for one hour. The precipitated bromide was filtered, washed with diethyl ether till the filtrate was colorless and dried to give the title compound in 91% yield.

$^1$H NMR (400 MHz, D₂O): 8.44 (br s, 1H, ArH), 7.99-7.89 (m, 3H, ArH), 7.83 (dd, 1H, ArH), 7.67-7.62 (m, 1H, ArH), 7.60-7.56 (m, 1H, ArH), 4.70 (s, 2H, CH₂), 3.72 (t, 6H, NCH₂), 3.21 (t, 6H, NCH₂).

Example 8

1-Naphthoylmethyl-(1-azonia-4-azabicyclo[2,2,2]octane) tetraphenylborate

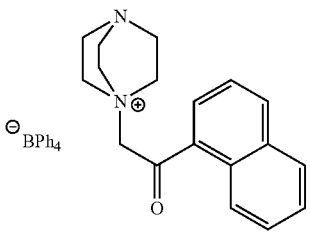 [SMILES: O=C(C[N+]12CCN(CC1)CC2)c1cccc2ccccc12 ; "BPh4"]

To an aqueous solution of the 1-naphthoylmethyl-(1-azonia-4-azabicyclo[2,2,2]octane) bromide one equivalent of an aqueous solution of sodium tetraphenylborate was added. The reaction mixture was stirred for one hour. The solid was filtered, washed with water, ether and dried to give the title compound in 88% yield.

$^1$H NMR (400 MHz, DMSO-d₆): 8.74 (br s, 1H, ArH), 8.17-8.11 (m, 2H, ArH), 8.07-8.00 (m, 2H, ArH), 7.77-7.70 (m, 2H, ArH), 7.25-7.23 (m, 1H, ArH), 7.18-7.15 (m, 8H, ArH), 6.92 (t, 8H, ArH), 6.79 (t, 4H, ArH), 5.31 (s, 2H, CH₂), 3.63 (t, 6H, NCH₂), 3.16 (t, 6H, NCH₂).

Example 9

1,5,7-triazabicyclo[4.4.0]dec-5-enylphenylglyoxylate

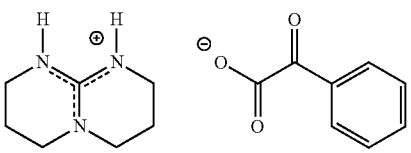

A solution of the phenylglyoxylic acid (0.25 g, 1.66 mmol) and 1,5,7-triazabicyclo[4.4.0]dec-5-ene (0.24 g 1.75 mmol) were stirred in ethanol at room temperature for 18 hours. Evaporation of solvent under vacuum yielded a solid that was recrystallized from hexane/ethanol to give the title compound (0.32 g) in 66% yield.

$^1$H NMR (400 MHz, DMSO-d₆): 8.63 (s, 2H), 7.83 (d, 2H), 7.61-7.57 (m, 1H), 7.51-7.48 (m, 2H), 3.28 (t, 4H), 3.18 (t, 4H), 1.91-1.85 (m, 4H).

Example 10

1,5,7-triazabicyclo[4.4.0]dec-5-enyl-4-nitrophenylglyoxylate

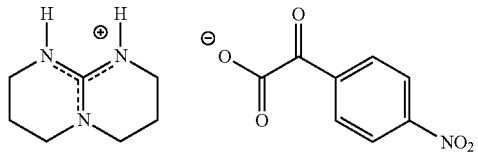

A solution of the 4-nitrophenylglyoxylic acid (0.25 g, 1.28 mmol) and 1,5,7-triazabicyclo[4.4.0]dec-5-ene (0.0.18 g 1.34 mmol) were stirred in ethanol at room temperature. A solid precipitated out, washed with hexane and recrystallized from hexane/ethanol to give the title compound (0.3 g) in 70% yield.

$^1$H NMR (400 MHz, DMSO-d₆): 8.34-8.32 (m, 2H), 8.07-8.04 (m, 2H), 7.99 (br s, 2H), 3.28 (t, 4H), 3.18 (t, 4H), 1.91-1.85 (m, 4H).

Example 11

1,5,7-triazabicyclo[4.4.0]dec-5-enyltetraphenylborate

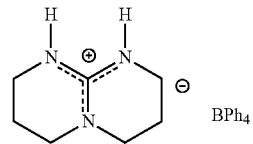

1,5,7-Triazabicyclo[4.4.0]dec-5-ene (61 mmol) was dissolved in 61 mL of 10% HCl (aq), followed by addition of a suspension of NaBPh₄ (67 mmol, 1.1 equivalent) in 85 ml water. A white precipitate was formed that was filtered and washed several times with water, methanol, and diethyl ether. The solid obtained was dried under vacuum to give the title compound in 82% yield.

$^1$H NMR (400 MHz, DMSO-d$_6$): 7.40 (s, 2H), 7.20-7.17 (m, 8H), 6.93 (t, 8H), 6.80 (t, 4H), 3.25 (t, 4H), 3.17 (t, 4H), 1.88-1.83 (m, 4H).

Example 12

1,8-Diazabicyclo[5.4.0]undec-7-enyltetraphenylborate

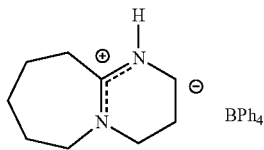

1,8-Diazabicyclo[5.4.0]undec-7-ene (9.85 mmol) was dissolved in 10 mL of 10% HCl (aq), followed by addition of a suspension of NaBPh$_4$ (10.85 mmol, 1.1 equivalent) in 13 ml water. A white precipitate was formed that was filtered and washed several times with water, methanol and diethyl ether. The solid obtained was dried under vacuum to give the title compound in 64% yield.

$^1$H NMR (400 MHz, DMSO-d$_6$): 9.48 (s, 1H), 7.20-7.16 (m, 8H), 6.93 (t, 8H), 6.80 (t, 4H), 3.55-3.52 (m, 2H), 3.46 (t, 2H), 3.24 (t, 2H), 2.64-2.61 (m, 2H), 1.93-1.87 (m, 2H) 1.67-1.60 (m, 6H).

ARRAY EXAMPLES

Example 13: Production of a COOH Coated Substrate Using Bis-Polyethylene Glycol Carboxy Methyl Ether This example describes how to construct a substrate comprising COOH groups. Silicon wafers deposited with Nickel 1000 Å on a silicon substrate were obtained from University Wafers. Dextran Bio Xtra (MW40000) was obtained from Sigma Aldrich. Bis-Polyethylene glycol carboxy methyl ether was obtained from Sigma Aldrich. Poly vinyl pyrollidone 1000000 was obtained from Poly Sciences Inc. The above three polymers were dissolved in a solvent composition of 50% Ethyl lactate/50% water by weight in a ratio of 2:2:1 by weight along with 2% by weight photoacid generator dimethyl-2,4-dihydroxyphenylsulfonium triflate obtained from Oakwood Chemicals Inc. This solution was spin-coated onto the silicon wafer.

The coated silicon wafer was spun at 3000 rpm to obtain a uniform coat of thickness 100 nm. The wafer was then exposed in a deep UV scanner Nikon S 203 at 250 mJ/cm$^2$ and then baked at 650 Celsius for 90 seconds in a hot plate. The coating was then stripped off the wafer with acetone and isopropyl alcohol followed by a deionized water rinse. The substrate had a matrix of free COOH groups ready to be activated and coupled with a protein or an amino acid for peptide synthesis. The 2-dimensional concentration of COOH groups along the layer is increased on a porous dextran substrate as compared to a planar substrate.

Example 14: Production of a COOH Coated Substrate Using Silane-PEG-COOH

Production of a COOH coated substrate was performed as follows: Silane-PEG-COOH was obtained from Nanocs. Pure ethyl alcohol was obtained from EMD Millipore. A mixture of 99.5% by weight ethyl alcohol and 0.5% by weight of Silane-PEG-COOH was dissolved and layered on a silica wafer for 48 hours at room temperature. The silica wafer was then washed with ethyl alcohol for 5 minutes followed by washing with deionized water for 5 minutes.

Example 15: Production of a COOH Coated Substrate Using Succinic Anhydride

Wafer with an NH$_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 1100 Celsius nitrogen bake oven to grow a mono silane layer with a —NH$_2$ group to attach a linker molecule.

Production of a COOH coated substrate was performed as follows: Succinic Anhydride was obtained from Sigma-Aldrich. N,N-dimethylformamide [DMF] was obtained from VWR International. A mixture of 50% by weight DMF and 50% by weight Succinic Anhydride was dissolved and reacted with a silica wafer containing NH$_2$ surface for 48 hours. The wafer was then washed with DMF for 5 minutes followed by washing with deionized water for 5 minutes.

Example 16: Production of a COOH Coated Substrate Using PEG Diacid

Wafer with an NH$_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 110° Celsius nitrogen bake oven to grow a mono silane layer with a —NH$_2$ group to attach a linker molecule.

Production of a COOH coated substrate was performed as follows: Poly(ethylene glycol) diacid (i.e., PEG-dipropionic acid) was obtained from Sigma-Aldrich. PEG diacid comprises 2 carboxylic acid groups. 1,3-diisopropylcarbodiimide [DIC] was obtained from Advanced ChemTech. Hydroxybenzotriazole [HOBt] was obtained from Anaspec. N-Methyl-2-Pyrrolidone [NMP] was obtained from VWR International. A mixture comprising of 2% by weight of DIC, 1% by weight of HOBt, 1% by weight of Poly(ethylene glycol) diacid dissolved in NMP was reacted with the silica wafer containing an NH$_2$ surface for 60 minutes. The wafer was then washed with NMP for 5 minutes. This was followed by reaction with a capping solution containing 50% Acetic Anhydride and 50% NMP to react with the unreacted NH$_2$ remaining on the surface for 15 minutes. This was followed by washing the wafer in NMP for 5 minutes.

Example 17: Production of a COOH Coated Substrate Using Trimesic Acid

Wafer with an NH$_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 110° Celsius nitrogen bake oven to grow a mono silane layer with a —NH$_2$ group to attach a linker molecule.

Production of a COOH coated substrate was performed as follows: Trimesic acid (Benzene-1,3,5-tricarboxylic acid, H3BTC) [TMA] was obtained from Sigma-Aldrich. Trimesic acid comprises 3 carboxylic acid groups. A mixture comprising of 2% by weight of DIC, 1% by weight of HOBt, 1% by weight of TMA dissolved in NMP was reacted with the silica wafer containing $NH_2$ surface for 12 hours. The wafer was then washed with NMP for 5 minutes. This was followed by reaction with a capping solution containing 50% by weight Acetic Anhydride and 50% by weight NMP to react with the unreacted $NH_2$ remaining on the surface for 15 minutes. This was followed by washing the wafer in NMP for 5 minutes.

Example 18: Production of a COOH Coated Substrate Using Mellitic Acid

Wafer with an $NH_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 110° C. nitrogen bake oven to grow a mono silane layer with a —$NH_2$ group to attach a linker molecule.

Production of a COOH coated substrate was performed as follows: Mellitic acid (Benzenehexacarboxylic acid) [MA] was obtained from Sigma Aldrich. Mellitic acid comprises 6 carboxylic acid groups. A mixture comprising of 2% by weight of DIC, 1% by weight of HOBt, 1% by weight of MA dissolved in NMP was reacted with the silica wafer containing $NH_2$ surface for 8 hours. The wafer was then washed with NMP for 5 minutes. This was followed by reaction with a capping solution containing 50% by weight Acetic Anhydride and 50% by weight NMP to react with the unreacted $NH_2$ remaining on the surface for 15 minutes. This was followed by washing the wafer in NMP for 5 minutes.

Example 19: Production of a COOH Coated Substrate Using Dextran and Benzophenone (Dextran 1)

Wafer with an $NH_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 110° Celsius nitrogen bake oven to grow a mono silane layer with a —$NH_2$ group to attach a linker molecule.

Production of a 3-dimensional COOH coated substrate was performed as follows: CM-Dextran (i.e., carboxy methyl dextran) salt was obtained from Sigma Aldrich. Benzophenone-4-carboxylic acid and 4-Aminobenzophenone were obtained from Sigma Aldrich. A mixture of 4% by weight EDC, 2% by weight of NHS and 2.5% by weight of benzophenone-4-carboxylic acid dissolved in ethanol was reacted with a silica wafer containing $NH_2$ surface for 60 minutes. A solution containing 3% by weight 4-Aminobenzophenone and 2% by weight of CM Dextran was generated by mixing with each other in solution phase for 120 minutes in the presence of EDC and NHS. EDC and NHS activated the COOH on the CM dextran, allowing coupling of the activated carboxylic acid group to the 4-aminobenzophenone. The resulting solution was then filtered to select for the portion containing coupled aminobenzophenone and CM Dextran. A solution comprising the portion containing coupled aminobenzophenone and CM Dextran along with a suitable polymer was then spin-coated onto the wafer reacted with benzophenone previously and exposed at 248 nm. Benzophenone on the wafer surface coupled with the benzophenone in solution which was coupled to CM Dextran. This linked the CM Dextran to the array surface via a benzophenone-benzophenone interaction, thus creating a substrate with a 3-dimensional arrangement of carboxylic acids on the surface.

Example 20: Production of a COOH Coated Substrate Using Dextran and an Amine Surface (Dextran 2)

Wafer with an $NH_2$ surface was prepared as follows: Aminopropyl triethoxy silane (APTES) was obtained from Sigma Aldrich. 100% Ethanol was obtained from VWR. The wafers were first washed with ethanol for 5 minutes and then in 1% by weight APTES/Ethanol for 20-30 minutes to grow the silane layer. Then the wafers were cured in a 110° Celsius nitrogen bake oven to grow a mono silane layer with a —$NH_2$ group to attach a linker molecule.

Production of a 3-dimensional COOH coated substrate was performed as follows: A mixture comprising of 2% by weight of DIC, 1% by weight of HOBt, 2.5% by weight of CM Dextran (i.e., carboxy methyl dextran) dissolved in NMP was reacted with the silica wafer containing $NH_2$ surface for 60 minutes. The wafer was then washed with NMP for 5 minutes. This was followed by reaction with a capping solution containing 50% by weight acetic anhydride and 50% by weight NMP to cap the unreacted $NH_2$ remaining on the surface for 15 minutes. This was followed by washing the wafer in NMP for 5 minutes. This created a substrate with a 3-dimensional arrangement of carboxylic acids on the surface.

Example 21: Carboxyl Surface Density on COOH Coated Substrates

Wafers with carboxyl surface were derivatized using different methods described in Examples 14-20 (Example 14: Silane PEG COOH, Example 15: Succinic Anhydride, Example 16: PEG diacid, Example 17: Trimesic acid, Example 18: Mellitic acid, Example 19: Dextran 1, and Example 20: Dextran 2). Surface density of the array generated by each method was tested. 4'-(Aminomethyl) Fluorescein, Hydrochloride was obtained from Life Technologies. 1-Ethyl-3-(3-dimethylaminopropyl) carbodiimide [EDC] and N-hydroxysuccinimide [NHS] were obtained from Sigma Aldrich. The carboxyl surface of each array was activated with an activation mixture of 4% by weight EDC and 2% by weight NHS dissolved in deionized water for 10 minutes. This was followed by washing the carboxyl surface of each array with deionized water for 3 minutes. A mixture containing 1% by weight of 4'-(Aminomethyl) fluorescein dissolved in deionized water was then added to the array and allowed to react for 30 minutes. This was followed by washing the array with deionized water for 5 minutes. Intensity of fluorescein was then checked using a 488 nm laser for all COOH substrates. The resulting fluorescein intensity correlating to carboxyl surface density is shown in FIG. 1.

Peptide synthesis and antibody binding as described in the methods below were performed. Results indicated a higher density of peptides synthesized on the 3-dimensional COOH surfaces generated in Example 19 and 20 (i.e., Dextran 1 and Dextran 2; data not shown).

Example 22: Production of a Substrate with Pillars

This example describes how to construct a substrate comprising pillars. Silicon wafers with 2.4 μm thermally grown oxide were obtained from University Wafers. The surface of the silicon wafer was cleaned with deionized water to remove contaminants from the wafer surface. The surface of the silicon wafer was primed for chemical adhesion of an organic compound to the wafer by applying vapors of hexamethyldisilizane (HMDS) onto a heated wafer substrate using a spray module at 200-220° Celsius for 30-50 seconds. HMDS was obtained from Sigma Aldrich Inc. HMDS acts as a "bridge" with properties to bind to both the wafer surface and the photoresist. The wafers were spun coat in a photoresist coat module with a commercially available deep Ultra violet photoresist, P5107 obtained from Rohm and Haas or AZ DX7260p 700 from AZ Electronic Materials, to obtain a thickness of 6000 Å. The wafers were then baked in a hot plate at 1200 Celsius for 60 seconds.

Photomasks that have the patterned regions to create the features were used to image the array on to the substrate surface. The wafers were then exposed in a 248 nm deep ultra violet radiation scanner tool, Nikon S203, with expose energy of 18 mJ/cm$^2$. The wafers were then post-exposure baked at 110° Celsius for 120 seconds in a hot plate and developed with commercially available NMD-3 developer, obtained from Tokyo Ohka Kogyo Co., Ltd., for 60 seconds.

After this the oxide was etched by using either a wet etch process or dry plasma etch process. Standard semiconductor etch techniques were used. Oxide etch depths were from 1000 Å to 2000 Å.

After etching, chromium was deposited to a thickness of 500 Å to 1500 Å by a physical deposition method. Standard etching and metal deposition techniques were employed.

After the chromium was deposited, the resist was lifted off with the following process: The wafers were left in Nanostrip obtained from Cyantek Inc. overnight and then dipped in Piranha solution for 90 min. Piranha solution is a 50:50 mixture of sulfuric acid and hydrogen peroxide. Sulfuric acid and hydrogen peroxide were obtained from Sigma Aldrich Corp. Plasma ashing was performed to oxidize the remaining impurities. This process produced a substrate having pillars of silicon dioxide separated by metal.

Alternatively, the deposited chromium was also polished to a depth of 500 Å to 1500 Å, depending on the deposition. The polishing was performed to obtain pillars of silicon dioxide separated by metal.

Derivatization: The wafers were then surface derivatized using the methods provided in Examples 13-21 to coat the pillar surface with free carboxylic acid attachment groups (i.e., COOH groups).

Example 23: Synthesis of Homopolymers and Heteropolymers from Fmoc-Protected Amino Acids This example illustrates the method of C→N synthesis of peptides on a chip array using carbodiimide activation of free carboxylic acid groups. Wafers with COOH groups were prepared as explained in Example 13. COOH groups were activated, and peptides deprotected and added to the activated COOH groups in a site and sequence-specific manner according to the method described below. The solutions used for the coupling reaction were prepared as follows:

Carboxylic Acid Activation Solution:

To prepare the carboxylic acid activation solution, 4% by weight of 1-ethyl-3-(3-dimethylaminopropyl) carbodiimide and 2% by weight of N-hydroxysuccinimide (NHS) were dissolved in deionized water.

Coupling Photobase Amino Acid Solution 1 (Table 5):

A solution containing the Fmoc-protected amino acid coupling molecule Alanine was prepared as follows: The polymer poly(methyl methacrylate) (i.e., PMMA) was dissolved in a 1:1 solvent solution of N-methylpyrrollidone and ethyl lactate. The final concentration of PMMA in solution was 1% by weight. Fmoc-Ala-OH was the coupling molecule and added to the solution to a final concentration of 2% by weight. Any other Fmoc protected amino acid can be used in place of Fmoc-Ala-OH for coupling of another amino acid. Photobase generators 1,3-Bis[(2-nitrobenzyl)oxycarbonyl-4-piperidyl]propane and 1,3-Bis[(1-(9-fluorenylmethoxycarbonyl)-4-piperidyl]propane were each added to the solution for a final concentration of 1% by weight.

Coupling Photobase Amino Acid Solution 2 (Table 5):

Another solution containing the Fmoc-protected amino acid coupling molecule Alanine was prepared as follows: The polymer PMMA was dissolved in the solvent N-methylpyrrollidone. The final concentration of PMMA in solution was 1% by weight. Fmoc-Ala-OH was the coupling molecule and added to the solution to a final concentration of 2% by weight. Any other Fmoc protected amino acid can be used in place of Fmoc-Ala-OH for coupling of another amino acid. Photobase generator 1,3-Bis[(2-nitrobenzyl)oxycarbonyl-4-piperidyl]propane was added to the solution for a final concentration of 1% by weight.

Coupling Photobase Amino Acid Solution 3 (Table 5):

A solution containing the Fmoc-protected amino acid coupling molecule Alanine was prepared as follows: The polymers PMMA and polyvinylpyrrolidone were each dissolved in the solvent N-methylpyrrolidone. The final concentration of PMMA and polyvinylpyrrolidone in solution were each 1% by weight. Fmoc-Ala-OH was the coupling molecule and added to the solution to a final concentration of 2% by weight. Any other Fmoc protected amino acid can be used in place of Fmoc-Ala-OH for coupling of another amino acid. Photobase generator 1,3-Bis [(2-nitrobenzyl)oxycarbonyl-4-piperidyl]propane was added to the solution for a final concentration of 1% by weight.

All Fmoc-protected amino acids were obtained from Anaspec. Polymethyl methacrylate (PMMA) and poly vinyl pyrrollidone were obtained from Polysciences Inc.

TABLE 5

| | | Photoactive Coupling Formulations | | |
| --- | --- | --- | --- | --- |
| Formulation | Polymer | Photoactive Compound | Coupling Molecule | Solvent |
| 1 | Polymethyl methacrylate | 1,3-Bis[(2-nitrobenzyl)oxycarbonyl-4-piperidyl]propane 1,3-Bis[(1-(9- | Fmoc-Ala-OH | Ethyl lactate/N-methyl-pyrrollidone (1:1 by weight) |

TABLE 5-continued

Photoactive Coupling Formulations

| Formulation | Polymer | Photoactive Compound | Coupling Molecule | Solvent |
|---|---|---|---|---|
| 2 | Polymethyl methacrylate | fluorenylmethoxycarbonyl)-4-piperidyl]propane 1,3-Bis[(2-nitrobenzyl)oxycarbonyl-4-piperidyl]propane | Fmoc-Ala-OH | N-methyl-pyrrollidone |
| 3 | Polymethyl methacrylate | 1,3-Bis[(2-nitrobenzyl)oxycarbonyl-4-piperidyl]propane | Fmoc-Ala-OH | N-methyl-pyrrollidone |

Solid-Phase N→C Synthesis Methodology

Figure 2:
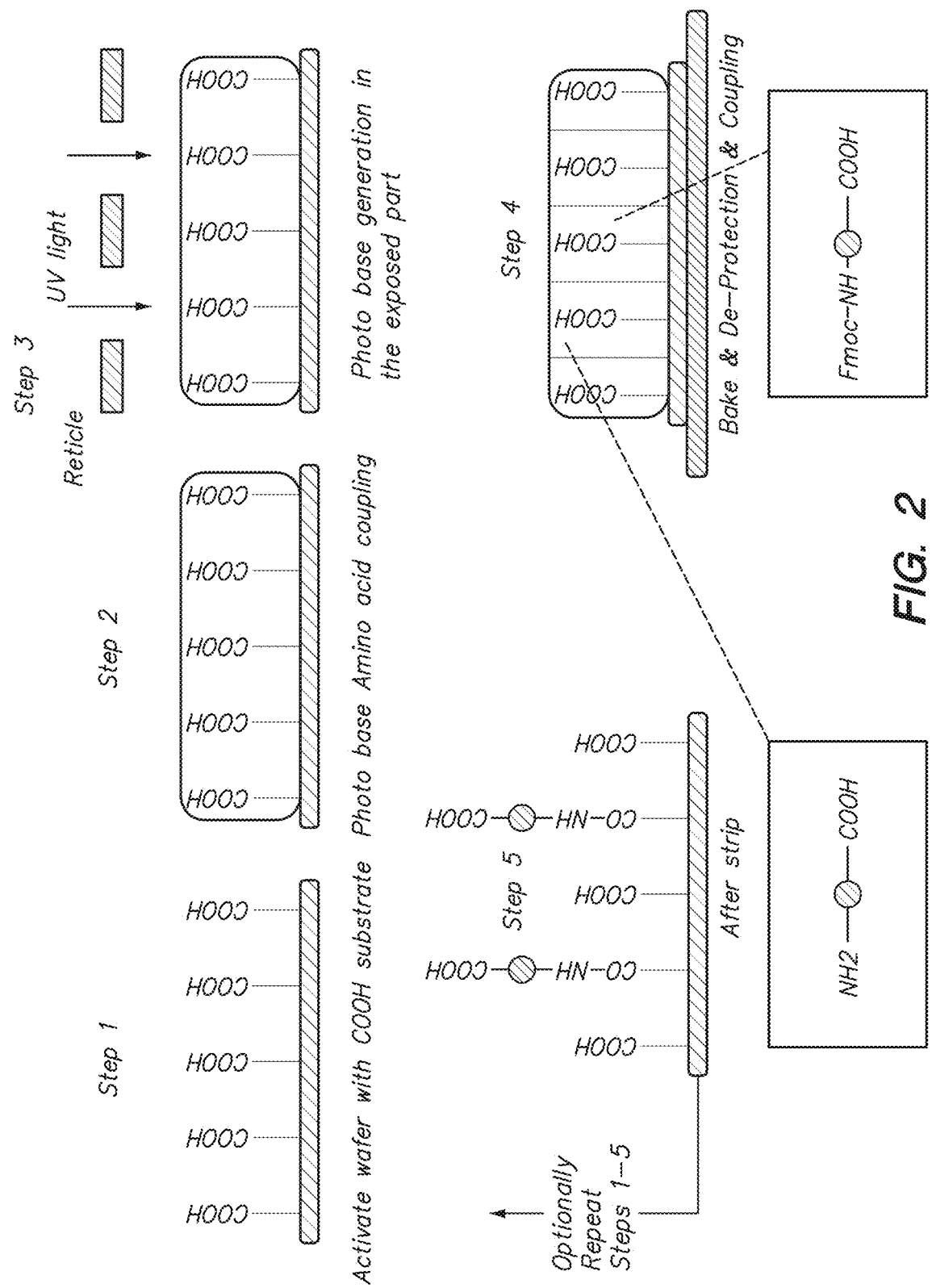
FIG. 2 shows a method of manufacturing an array.

Attachment of a free amino acid to the free carboxylic acid group attached to the surface of the substrate is shown in FIG. 2. As shown in step 1, the COOH-coated wafer substrate was activated by adding carboxylic acid activation solution to the surface of the wafer and spinning the wafer to form a layer of carboxylic activation solution on the surface of the wafer. Carbodiimide in the carboxylic acid activation solution reacted with the free carboxylic acid groups to generate a free carbonyl group (e.g., an "activated carboxylic acid group"). The carboxylic acid group activation solution was then washed from the surface of the wafer. As shown in step 2, one of the three coupling photobase amino acid solutions described above (also see Table 5) was then spin-coated onto a wafer at 3000 rpm and baked at 65° Celsius for 1 minute on a hot plate. The wafer was then selectively exposed to electromagnetic radiation at 248 nm and at 80 mJ/cm$^2$ using a reticle (Step 3) and then hard baked at 850 Celsius for 90 seconds in a hot plate (Step 4). Fmoc-Ala-OH was deprotected by photoactivated release of a base from the photobase generator of the coupling photobase amino acid solution only in the region where it is exposed to radiation. The amino acid was coupled to the activated carboxylic acid group simultaneously with deprotection of the Fmoc-protected amine group. The solution was then stripped from the wafer, leaving the newly coupled amino acid bound to the activated carboxylic acid at site-specific locations (Step 5). Steps 2-5 were repeated to couple different amino acids to remaining activated carboxylic acid groups. After an amino acid had been coupled at each desired location, carboxylic acid group activation as performed in step 1 was optionally repeated to activate carboxylic acid groups on the entire surface of the array to add another layer of amino acids (cycle of steps 2-5). The process generated sequence-specific peptide chains at specific locations on the substrate. Results obtained for selected sequences are described in further detail below.

20 Mer Homopolymer Synthesis and Coupling Step Efficiency

The photoactive coupling step described above was performed for synthesizing 20-mer peptides with the following sequences:

Ala-Ala-Ala-Ala-Ala-Ala-Ala-Ala-Ala-Ala-Ala-Ala-Ala-Ala-Ala-Ala-Ala-Ala-Ala-Ala

In this example the step yield data for each of the above 20-mer amino acid sequences was measured. To measure step yield via fluorescence, uncoupled activated carboxylic acids were exposed to a capping solution comprising ethanolamine to prevent addition of another amino acid or fluorescein dye molecule. After capping, the fluorescent dye molecule was coupled to the sequence of amino acids in order to determine the coupling efficiency according to the following protocol: 5-(Aminomethyl) Fluorescein, Hydrochloride was obtained from Life tech. 0.1 M Boc-Gly-OH (from AAPPTeC), 0.05 M 5-AFH and 0.1 M HoNb (Sigma Aldrich) and 0.1 M EDC (Sigma Aldrich) was dissolved in water along with 5-10% by weight Poly vinyl pyrrolidone (Polysciences). This solution is referred to herein as the "fluorescein coupling solution." The COOH-coated wafer substrate comprising capped uncoupled carboxylic acids was activated by adding carboxylic acid activation solution to the surface of the wafer and spinning the wafer to form a layer of carboxylic activation solution on the surface of the wafer. Carbodiimide in the carboxylic acid activation solution reacted with the free carboxylic acid groups to generate a free carbonyl group (e.g., an "activated carboxylic acid group"). The carboxylic acid group activation solution was then washed away. The fluorescein coupling solution was then spin coated on the wafer at 2000 rpm to form a coupling dye coat. Next the wafers were baked at 650 Celsius for 2 minutes and then the fluorescein coupling solution was washed away with water. This completed the coupling of fluorescein dye to measure the proportion of uncapped: capped peptide chains to measure synthesis efficiency. The signal was then read off a fluorescence microscope. For all the experiments, the measured signal intensity was directly correlated to the coupling yield. The deprotection yield can be calculated by the amount of fluorescein coupled to the COOH on the substrate after each synthesis step.

The amount of fluorescein dye coupled gives a direct measure of the amount of sequence grown. The formula used to calculate average n-th step yield (i.e., "F") was: $F=(F_n/F_1)/n-1$, where $F_1$ and $F_n$ denotes the fluorescein coupling intensity read out from a fluorescent scanner device at the first step and the nth step. The average coupling yield (i.e., average coupling efficiency, or "E") was calculated using the formula $E=10\hat{}((\log F)/C)$ where F equals fraction of full length and C=number of couplings=length−1. The step yield at each step was calculated by the equation $F_{n+1}/F_n$, wherein, after the first coupling, n=1, after the second coupling, n=2, and so on. The coupling yield at each step was given by the same formula, as fluorescence directly correlates to synthesis efficiency at each step.

Figure 3A:
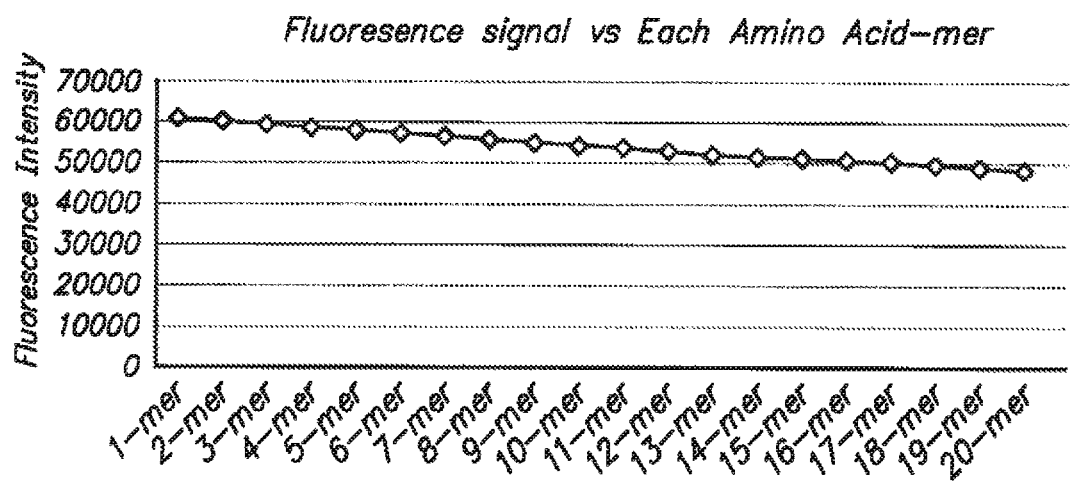
FIG. 3A shows the readout of fluorescence signal from each step of the synthesis of a 20-mer homopolymer.
Figure 3B:
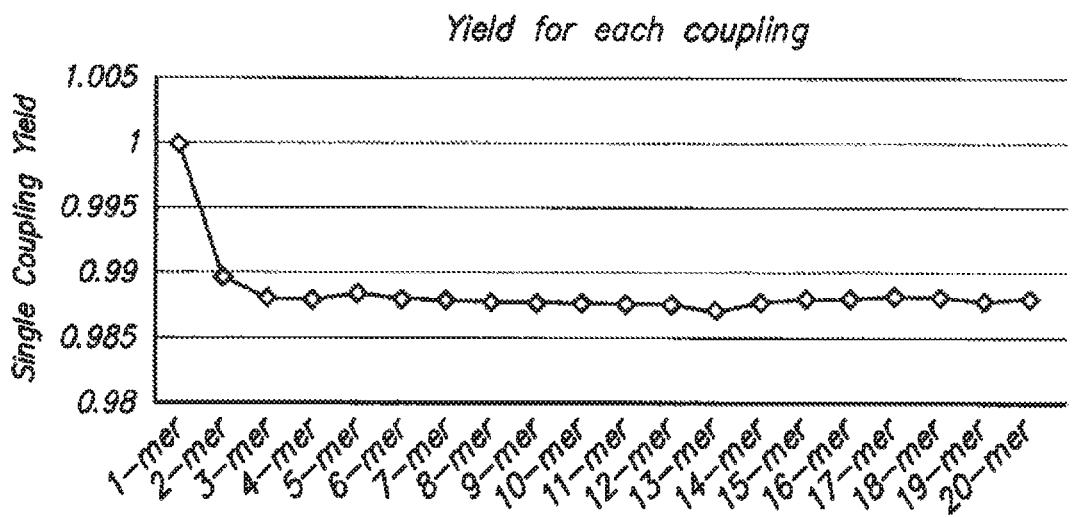
FIG. 3B shows the coupling efficiency for each addition of a peptide to the homopolymer.

FIG. 3A shows a graph of fluorescence signal intensity versus each amino acid layer. FIG. 3B shows a graph of overall step yield versus each amino acid layer. Table 6 shows the yield efficiency for each coupling step. The coupling efficiency of each amino acid was calculated to be greater that 98.5% in each instance across the entire length of the 20-mer peptide.

TABLE 6

20-mer homopolymer coupling yield

| Amino Acid | Fluorescence | Coupling Efficiency | n-th Step Yield |
|---|---|---|---|
| 1-mer | 61000 | 1.00000 | 1.00000 |
| 2-mer | 60363.4 | 0.98956 | 0.98956 |
| 3-mer | 59558.98 | 0.98812 | 0.97638 |
| 4-mer | 58826 | 0.98798 | 0.96436 |
| 5-mer | 58231 | 0.98845 | 0.95461 |
| 6-mer | 57436.8 | 0.98803 | 0.94159 |
| 7-mer | 56705.9 | 0.98791 | 0.92960 |
| 8-mer | 56001.23 | 0.98786 | 0.91805 |
| 9-mer | 55289.1 | 0.98779 | 0.90638 |
| 10-mer | 54576.6 | 0.98771 | 0.89470 |
| 11-mer | 53888.2 | 0.98768 | 0.88341 |
| 12-mer | 53212.3 | 0.98766 | 0.87233 |
| 13-mer | 52247.8 | 0.98718 | 0.85652 |
| 14-mer | 51987.6 | 0.98778 | 0.85226 |
| 15-mer | 51545.7 | 0.98804 | 0.84501 |
| 16-mer | 50928.9 | 0.98804 | 0.83490 |
| 17-mer | 50526.9 | 0.98830 | 0.82831 |
| 18-mer | 49818.6 | 0.98816 | 0.81670 |
| 19-mer | 48959.4 | 0.98786 | 0.80261 |
| 20-mer | 48543.4 | 0.98805 | 0.79579 |

12 Mer Heteropolymer Synthesis and Coupling Step Efficiency

The photoactive coupling step described above was performed for synthesizing up to 12-mer polypeptides. Amino acids used in this example were Fmoc-Lys-OH, Fmoc-Leu-OH, Fmoc-Met-OH, Fmoc-Thr-OH, Fmoc-Ser-OH, Fmoc-Asp-OH, Fmoc-Gly-OH, Fmoc-Ile-OH, Fmoc-Ala-OH, Fmoc-Arg-OH, Fmoc-Val-OH. All amino acids were obtained from Anaspec. These amino acids were added to the coupling photobase amino acid solution in place of Fmoc-Ala-OH in the coupling photobase amino acid solutions described previously.

The sequence was synthesized using the carbodiimide activated COOH and Fmoc-protected peptide coupling method described above. Fluorescein coupling was performed to the final product to measure synthesis efficiency as described above.

The 12 mer polypeptide was synthesized according to the following steps:
1. Lys
2. Lys-Leu
3. Lys-Leu-Glu
4. Lys-Leu-Glu-Arg
5. Lys-Leu-Glu-Arg-Ser
6. Lys-Leu-Glu-Arg-Ser-Thr
7. Lys-Leu-Glu-Arg-Ser-Thr-Val
8. Lys-Leu-Glu-Arg-Ser-Thr-Val-Met
9. Lys-Leu-Glu-Arg-Ser-Thr-Val-Met-Ile
10. Lys-Leu-Glu-Arg-Ser-Thr-Val-Met-Ile-Lys
11. Lys-Leu-Glu-Arg-Ser-Thr-Val-Met-Ile-Lys-Gly
12. Lys-Leu-Glu-Arg-Ser-Thr-Val-Met-Ile-Lys-Gly-Asp The formula used to calculate average n-th step yield (i.e., "F") was: $F=(F_n/F_1)/n-1$, where $F_1$ and $F_n$ denotes the fluorescein coupling intensity read out from a fluorescent scanner device at the first step and the nth step. The average coupling yield (i.e., average coupling efficiency, or "E") was calculated using the formula $E=10\wedge((\log F)/C)$ where F equals fraction of full length and C=number of couplings=length−1. The step yield at each step was calculated by the equation $F_{n+1}/F_n$, wherein, after the first coupling, n=1, after the second coupling, n=2, and so on. The coupling yield at each step was given by the same formula, as fluorescence directly correlates to synthesis efficiency at each step.

Figure 4A:
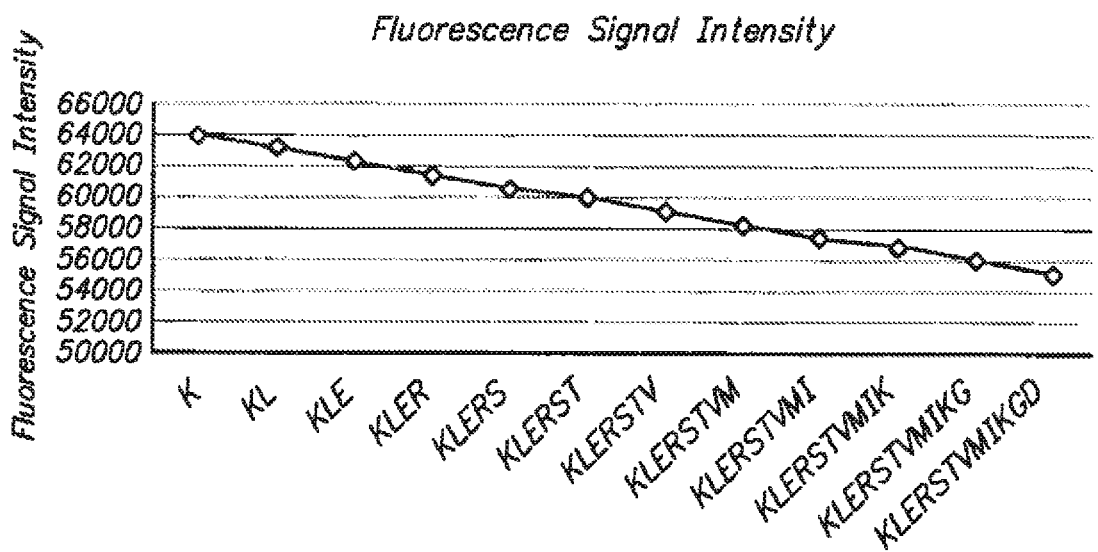
FIG. 4A shows the readout of fluorescence signal from each step of the synthesis of a 12-mer heteropolymer.
Figure 4B:
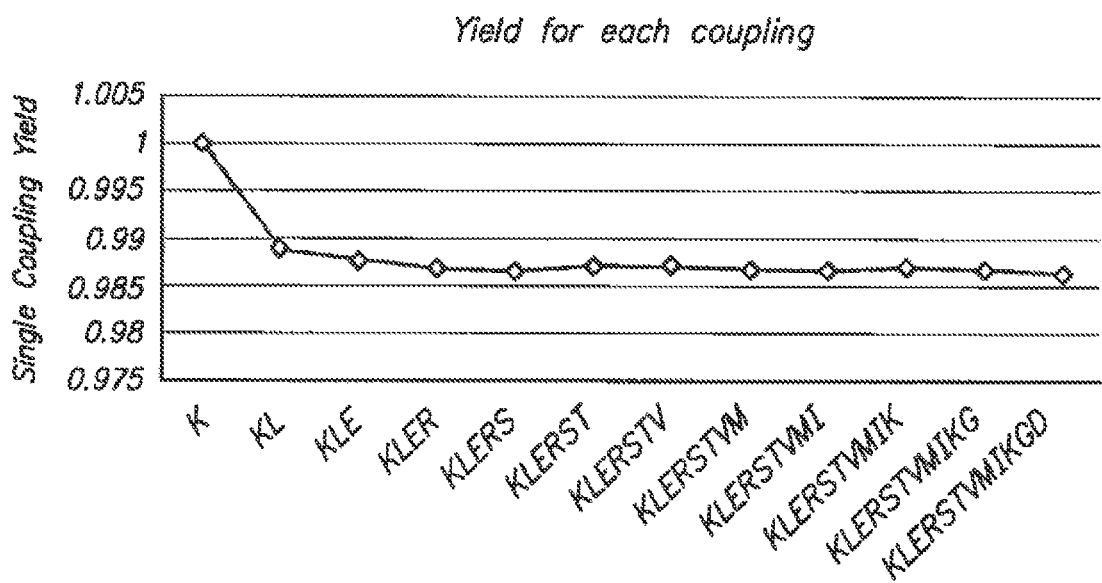
FIG. 4B shows the coupling efficiency for each addition of a peptide to the heteropolymer.

FIG. 4A shows a graph of fluorescence signal intensity versus each amino acid layer. FIG. 4B shows a graph of overall step yield for each amino acid addition. The columns contain the sequence synthesized such that one amino acid is added in each column.

The coupling efficiency of each amino acid was calculated to be greater than 98.5% in each instance across the entire 12-mer peptide and the overall yield of the full length 12 amino acid polypeptide was calculated as 86.13%. Table 7 shows the results of the synthesis reaction.

TABLE 7

12-mer heteropolymer yield

| Amino Acid | Peptide Sequence | Fluorescence | Coupling Efficiency | n-th Step Yield |
|---|---|---|---|---|
| 1-mer | K | 63987 | 1.00000 | 1.00000 |
| 2-mer | KL | 63276 | 0.98889 | 0.98889 |
| 3-mer | KLE | 62431.5 | 0.98777 | 0.97569 |
| 4-mer | KLER | 61504.8 | 0.98690 | 0.96121 |
| 5-mer | KLERS | 60648 | 0.98669 | 0.94782 |
| 6-mer | KLERST | 60000 | 0.98722 | 0.93769 |
| 7-mer | KLERSTV | 59198 | 0.98712 | 0.92516 |
| 8-mer | KLERSTVM | 58307.5 | 0.98681 | 0.91124 |
| 9-mer | KLERSTVMI | 57446.3 | 0.98661 | 0.89778 |
| 10-mer | KLERSTVMIK | 56874.1 | 0.98699 | 0.88884 |
| 11-mer | KLERSTVMIKG | 56088.8 | 0.98691 | 0.87657 |
| 12-mer | KLERSTVMIKGD | 55113.4 | 0.98652 | 0.86132 |

Example 24: Carboxylic Acid Surface Activation Lifetimes

Wafers with carboxylic acid surfaces were prepared as explained in Example 17 (Trimesic acid coating). Different coupling reagents were then tested for determining the lifetime of an activated ester. 1-Ethyl-3-(3-dimethylamino-propyl) carbodiimide [EDC] and N-hydroxysuccinimide [NHS] were obtained from Sigma Aldrich. 1,3-Diisopropylcarbodiimide [DIC] was obtained from Advanced ChemTech. Hydroxybenzotriazole (HOBt) was obtained from Anaspec. (O-(7-azabenzotriazol-1-yl)-N,N,N',N'-tetramethyluronium hexafluorophosphate) [HATU] and Benzotriazol-1-yl-oxytripyrrolidinophosphonium hexafluorophosphate [PyBOP] were obtained from Aapptec. N,N-Diisopropylethylamine [DIEA] was obtained from Alfa Aesar.

The wafer was activated with the different combinations of reagents yielding the following activation solutions: (1) EDC and NHS with 4% by weight of EDC and 2% by weight of NHS were dissolved in deionized water and reacted with the wafer at room temperature for 10 minutes. The wafer was then washed with deionized water; (2) DIC and HOBt with 4% by weight of DIC and 2% by weight of HOBt were dissolved in NMP and reacted with the wafer at room temperature for 10 minutes. The wafer was then washed with NMP; (3) HATU and N,N-Diisopropylethyl-amine (DIEA) with 4% by weight of HATU and 2% by weight of DIEA were dissolved in NMP and reacted with the wafer at room temperature for 8 minutes. The wafer was then washed with NMP; and (4) PyBOP and DIEA with 4% by weight of PyBOP and 2% by weight of DIEA were dissolved in NMP and reacted with the wafer at room temperature for 25 minutes. The wafer was then washed with NMP.

Figure 5:
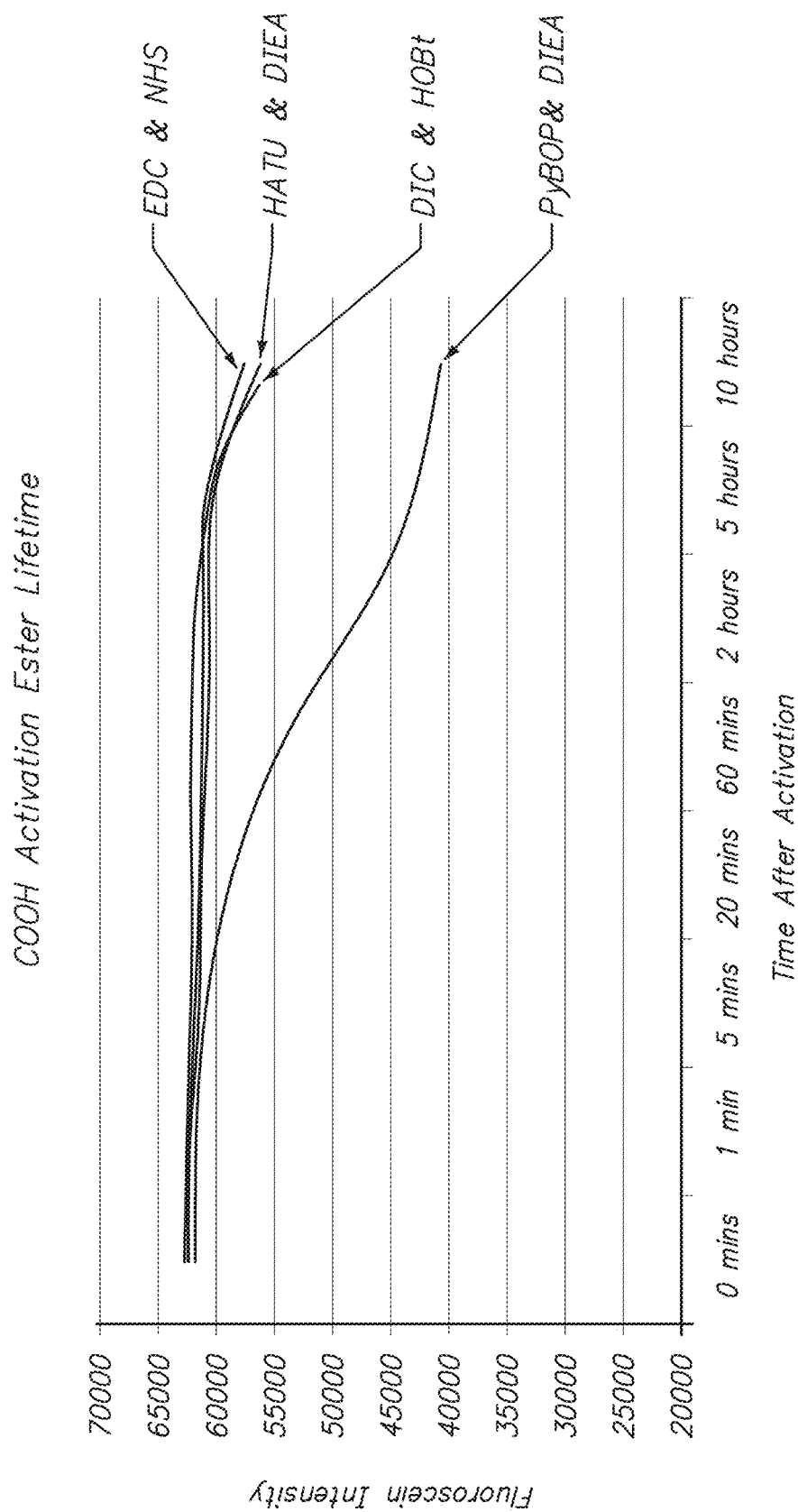
FIG. 5 shows a graph of activation lifetimes of carboxylic acids on the surface of a wafer activated by different activation solvents.

After washing the wafers were checked for activation lifetime of each reagent for different time periods (1 minute, 5 minutes, 20 minutes, 60 minutes, 2 hours, 5 hours and 10 hours). For each activation reagent, after each time period, the amount of free carboxylic acid on each array was measured by measuring fluorescence intensity using 4'-Aminomethyl fluorescein as explained above. Results indicating the lifetime of activation of carboxylic acids on the surface of each array are shown in FIG. 5.

PyBOP and DIEA activation ester were susceptible to faster hydrolysis. The other esters showed stability for 5-6 hours. Thus, a single activation step can be used for multiple coupling cycles for sequence-specific addition at multiple locations. The above experiment was also performed with the COOH wafer generated in Example 18 (Mellitic acid). Results (not shown) were similar, demonstrating stability of activation for 5-6 hours with the above activation solutions (1)-(4).

Example 25: Peptide Synthesis on a COOH Substrate Using Fmoc Protected Amino Acids Wafers with carboxylic acid surfaces were prepared as explained above using trimesic acid (Example 17). Fluorenylmethyloxycarbonyl [Fmoc] protected amino acids were obtained from Anaspec, including Histidine (H), Arginine (R), Serine (S), Valine (V) and Glycine (G). Ethanolamine was obtained from Sigma Aldrich.

The carboxylic acid surface was activated as follows: 4% by weight of EDC and 2% by weight of NHS were dissolved in deionized water and reacted with the wafer at room temperature for 10 minutes. The wafer was then washed with deionized water.

The deprotection and coupling to the carboxylic acids on the wafer was checked by binding a sequence-specific antibody to known amino acid sequence (RHSVV). Amino acid coupling was performed as follows: a photobase coupling solution containing a copolymer (2.5% by weight of PMMA added to 1.5% by weight of Poly ethylene glycol), 1% by weight of amino acid and 2.5% by weight of photobase generator was spin-coated onto a wafer and baked. Next, the wafer was exposed to 248 nm light using a reticle and then hard baked. Fmoc was removed from the amino acid only in the region, where photobase was exposed to light and the deprotected amino acid was coupled simultaneously. The wafer was stripped with acetone and isopropyl alcohol [IPA].

After the first layer of amino acid was coupled, ethanolamine was used for capping the activated COOH that have not been coupled. This was done by spin coating a mixture of polymer and ethanolamine in deionized water and then baking. The wafer was then stripped with deionized water. The process of carboxylic acid activation, deprotection and coupling for each amino acid at selected sites on the wafer, and capping was repeated for coupling each of the next layers of amino acid to the wafer. Two sequences were synthesized on the wafer: RHSVV (natural sequence) and GHSVV (mutant sequence).

After completion of polypeptide synthesis, any protecting groups on the side chains of the polypeptide were removed. Trifluoroacetic Acid [TFA] was obtained from Sigma Aldrich. Pentamethylbenzene [PMB] and Thioanisole were obtained from VWR. A hydrogen bromide solution of 33% by weight hydrogen bromide in acetic acid [HBr] was obtained from Sigma Aldrich.

The wafer was washed with TFA for 10 minutes. A solution comprising of 0.4% by weight PMB and 0.4% by weight thioanisole was dissolved in TFA. After stirring thoroughly, 4% by weight of HBr was added and the wafer was washed with this solution for 60 minutes. The same process was repeated again for a further 60 minutes. The wafer was then washed with TFA for 5 minutes, IPA for 5 minutes, then DMF for 5 minutes. The wafer was then neutralized with 5% DIEA in DMF for 5 minutes, then washed with DMF for 5 minutes, and finally washed with IPA for 5 minutes.

Anti-p53 antibody specific to the RHSVV polypeptide and Goat anti-mouse IgG for detection of binding of the anti-p53 antibody to the RHSVV polypeptide were obtained from ABCAM. TBS Buffer, PBST Buffer and BSA were obtained from VWR International. The assay to detect polypeptide synthesis on the peptide array (e.g., the bioassay) was performed as follows: The chip containing the natural and mutated sequence grown was washed with methanol for 5 mins followed by washing with TBS Buffer for 5 mins. Primary antibody solution containing PBST, 1% BSA, and Anti-p53 antibody was incubated on the chip at 37° Celsius for 1 hour. The chip was then washed with PBST for 5 minutes thrice. (Throughout this specification, the absence of a recited temperature indicates that a step was carried out at room temperature, i.e., approximately 23° Celsius.) This was followed by secondary antibody incubation at 370 Celsius for 1 hour. The secondary antibody solution contained PBST, 1% BSA, and Goat Anti-mouse IgG. The chip was then washed with PBST for 5 minutes thrice. This was followed by washing with deionized water for 5 minutes twice. The concentration of anti-p53 antibody was varied and the results of antibody binding were measured to validate the efficiency of synthesis using the single step deprotection and coupling process described above.

Figure 6:
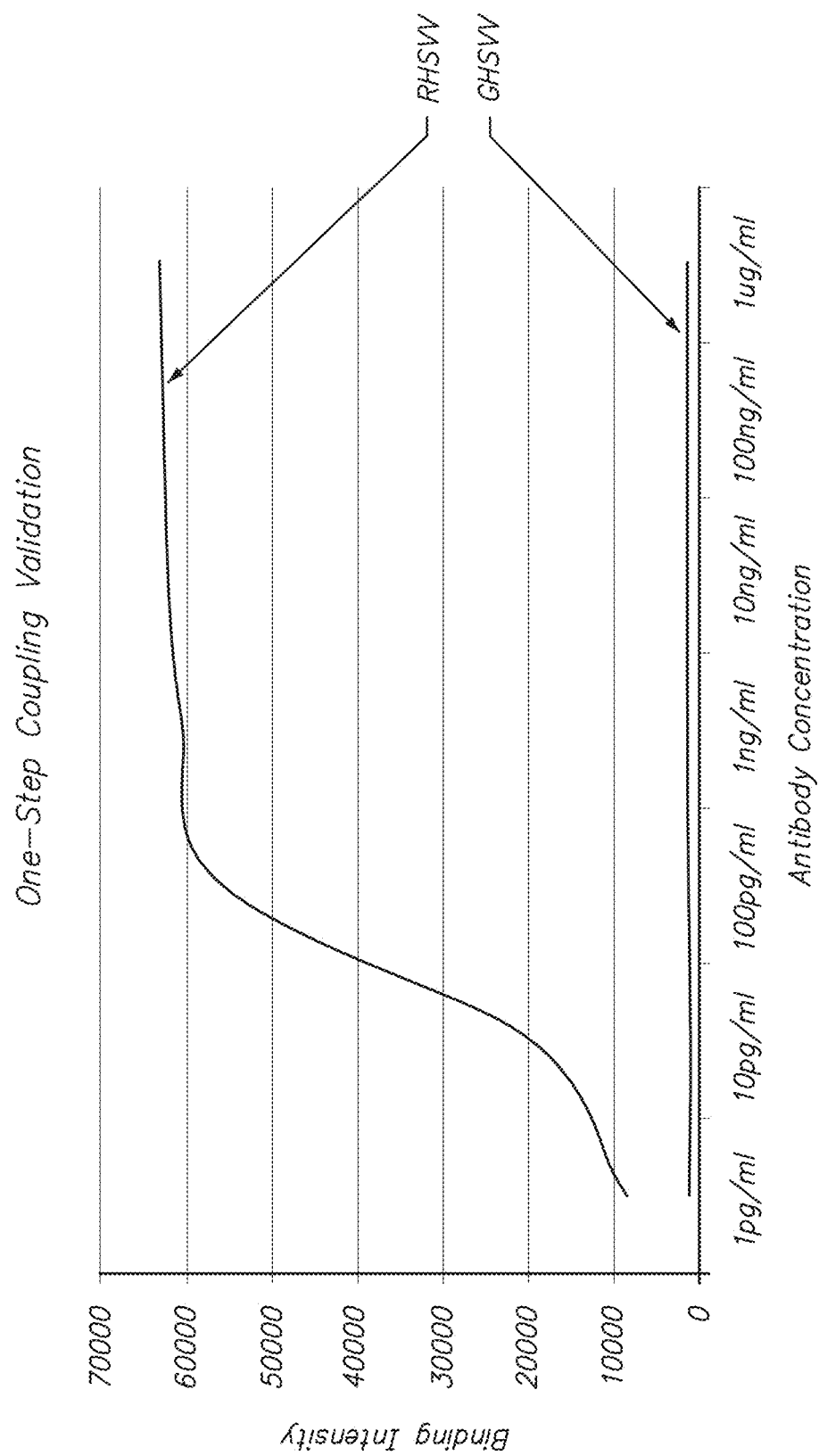
FIG. 6 shows binding of antibodies specific for RHSVV to a peptide array with RHSVV and GHSVV sequences synthesized by the methods described herein.

Results of antibody binding to the chip comprising RHSVV (normal) versus GHSVV (mutant) sequences are shown in FIG. 6. As shown, antibody concentration of 1 pg/ml can be detected using this method and the binding intensity showed log-linear increase with increasing antibody concentration over the lower end of the tested range and plateaus from 100 pg/ml to 1 µg/ml.

In the coupling solution, a scavenger can be added to ensure complete scavenging of the deprotection product. Examples of such scavengers include, but are not limited to, alkyl thiols, such as dithiothreitol, 1-propanethiol or 1-decanethiol.

C-terminal amidation can be performed on selective peptides if necessary. This process can take place in a solution containing ammonium chloride, ethylammonium chloride and semicarbazide hydrochloride in the presence of HATU and DIEA at room temperature.

Example 26: Photobase Generator Compositions

Photobase generator compositions were prepared and tested to determine their performance for polypeptide synthesis on an array as described above. Each photobase generator composition comprised a photobase generator having a structure and general formula as shown in Tables 2 and 3. The photobase generators were commercially available or synthesized as described above.

Preparation of photobase generator compositions was performed as follows: a mixture of 1-3% by weight of polymethyl methacrylate [PMMA] was added to cyclohexanone and stirred thoroughly for 24 hours. After 24 hours stirring, 1.5-5% by weight of photobase generator, depending on the molecular weight of the photobase generator, was mixed in the solution and stirred thoroughly for 24 hours. Then, 0.1 M of the suitable amino acid was added to the solution and stirred for 10 hours at room temperature.

Wafer with carboxylic acid surfaces were prepared as explained above in Example 17 (Trimesic acid). Different coupling reagents were then tested for determining the lifetime of an activated ester. 1-Ethyl-3-(3-dimethylaminopropyl) carbodiimide [EDC] and N-hydroxysuccinimide [NHS] were obtained from Sigma Aldrich. 1,3-Diisopropylcarbo-diimide [DIC] was obtained from Advanced ChemTech. Hydroxybenzotriazole (HOBt) was obtained from Anaspec. (O-(7-azabenzotriazol-1-yl)-N,N,N',N'-tetramethyluronium hexafluorophosphate) [HATU] and Benzotriazol-1-yl-oxytripyrrolidinophosphonium hexafluorophosphate [PyBOP] were obtained from Aapptec. N,N-Diisopropylethylamine [DIEA] was obtained from Alfa Aesar.

Performance of the photobase generator compositions was tested as follows: Amino acid coupling was performed as described above. Each composition containing a polymer, amino acid and photobase generator was spin-coated onto a wafer and baked. Next, the wafer was exposed to 248 nm radiation and then hard baked. Fmoc amino acids were deprotected only in the region where the amino acids were exposed to the radiation. The amino acid was coupled to the activated carboxylic acid groups immediately after exposure to the 248 nm radiation with a list of used amino acids shown in Table 8. The wafer was then stripped with acetone and IPA.

TABLE 8

List of amino acids used in photobase generator assay.

| Amino Acid | Description |
| --- | --- |
| CIT—Citrulline | Fmoc-L-Citrulline |
| A—Alanine | Fmoc-Ala-OH |
| C—cysteine | Fmoc-Cys(Bzl)-OH |
| D—aspartic acid | Fmoc-Asp(Obzl)-OH |
| E—glutamic acid | Fmoc-Glu(Obzl)-OH |
| F—phenylalanine | Fmoc-Phe-OH |
| G—glycine | Fmoc-Gly-OH |
| H—histidine | Fmoc-His(Trt)-OH |
| I—isoleucine | Fmoc-Ile-OH |
| K—lysine | Fmoc-Lys(Boc)-OH |
| L—leucine | Fmoc-Leu-OH |
| M—methionine | Fmoc-Met-OH |
| N—asparagine | Fmoc-Asn(Trt)-OH |
| P—proline | Fmoc-Pro-OH |
| Q—glutamine | Fmoc-Gln(Trt)-OH |
| R—arginine | Fmoc-Arg(Tos)-OH |
| S—serine | Fmoc-Ser(Bzl)-OH |
| T—threonine | Fmoc-Thr(Bzl)-OH |
| V—valine | Fmoc-Val-OH |
| W—tryptophan | Fmoc-Trp(Boc)-OH |
| Y—tryosine | Fmoc-Tyr(Bzl)-OH |

Ethanolamine was used for capping any activated COOH groups which had not been coupled. This was done by spin coating a mixture of polymer, ethanolamine and deionized water onto the wafer and then baking the coated wafer. The wafer was then stripped with deionized water and the same process was repeated for coupling the next amino acid.

A sequence of amino acids was synthesized at predetermined locations on a chip by repeating the method above with selected Fmoc-protected amino acids and polypeptide synthesis performance was determined by using measurements of yield at each step of synthesis. This was done by coupling one amino acid at a time and finally activating the carboxylic acid groups on the wafer and coupling aminomethyl fluorescein for each step yield.

Example 27: Efficiency of Synthesis for Protected and Unprotected Amino Acids

One-step deprotection and coupling was validated in comparison with coupling of unprotected amino acids and unprotected amino acids in the presence of a photobase. A wafer with carboxylic acid surface was prepared as explained above in Example 17 (Trimesic acid).

Amino acids used during synthesis were Citrulline (CIT), Alanine (A), Cysteine (C), Aspartic acid (D), Glutamic acid (E), Phenylalanine (F), Glycine (G), Histidine (H), Isoleucine (I), Lysine (K), Leucine (L), Methionine (M), Asparagine (N), Proline (P), Glutamine (Q), Arginine (R), Serine (S), Threonine (T), Valine (V), Tryptophan (W) and Tryosine (Y). Unprotected amino acids and Fmoc-protected amino acids were obtained from Anaspec.

The carboxylic acid surface on a wafer was activated with an activation mixture of 4% by weight EDC and 2% by weight NHS dissolved in deionized water for 10 minutes. This was followed by washing the wafer with deionized water for 3 minutes.

Experiment 1 [E1]

Amino Acid coupling was performed as follows: a coupling solution containing a copolymer (2.5% by weight of PMMA added to 1.5% by weight of Poly Ethylene Glycol) and 1% by weight of unprotected amino acid was spin-coated onto a wafer and baked. The reaction resulted in the unprotected amino group in the amino acid coupling to the activated carboxylic acid present on the surface. Ethanolamine was used for capping any activated COOH groups on the surface of the wafer, which did not couple to the amino acid. This was done by spin coating a mixture of polymer, ethanolamine, and deionized water onto the wafer and then baking the coated wafer. The wafer was then stripped with deionized water.

Experiment 2 [E2]

Amino Acid coupling was performed as follows: a photoresist coupling solution containing a copolymer (2.5% by weight of PMMA added to 1.5% by weight of Poly Ethylene Glycol), 5% by weight of photobase generator, and 1% by weight of unprotected amino acid was spin-coated onto a wafer, baked and the wafer was exposed to 248 nm radiation. The reaction resulted in the unprotected amino group in amino acid coupling to the activated carboxylic acid present on the surface. Ethanolamine was used for capping any activated COOH groups on the surface of the wafer which did not couple to the amino acid. This was done by spin coating a mixture of polymer, ethanolamine, and deionized water onto the wafer and then baking the coated wafer. The wafer was then stripped with deionized water. This experiment tested the effect of base on the activated ester and tested the effect of base in the coupling process.

Experiment 3 [E3]

Amino Acid coupling was performed as follows: a photoresist coupling solution containing a copolymer (2.5% by weight of PMMA added to 1.5% by weight of Poly Ethylene Glycol), 1% by weight of unprotected amino acid and 2.5% by weight of photobase generator was spin-coated onto a wafer and baked. The Fmoc-protected amino acid was deprotected, when exposed to 248 nm radiation, allowing the amino group in amino acid to couple to the activated carboxylic acid present on the surface with spatial specificity. Ethanolamine was used for capping any activated COOH groups on the surface of the wafer which did not couple to the amino acid. This was done by spin coating a mixture of polymer, ethanolamine, and deionized water onto the wafer and then baking the coated wafer. The wafer was then stripped with deionized water.

Figure 7:
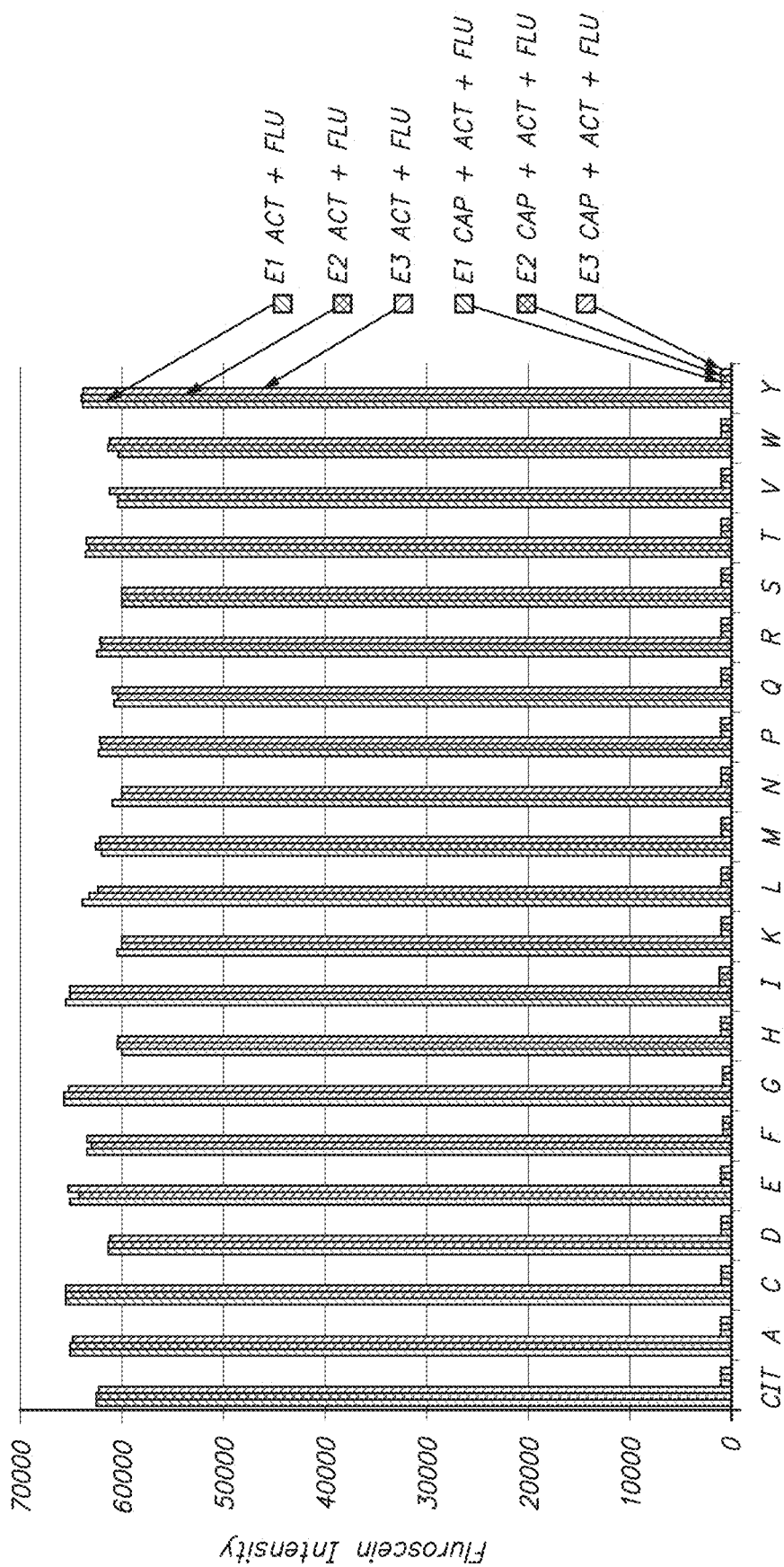
FIG. 7 shows fluorescein intensity to measure coupling efficiency of each amino acid under different experimental conditions as described herein.

Experiments E1, E2 and E3 were performed for all amino acids. Coupling efficiency for each experiment was determined by adding aminomethyl fluorescein directly on the wafer that had been capped before activation as a baseline (CAP+ACT+FLU), and also by activating the wafer and coupling aminomethyl fluorescein (ACT+FLU) for each experiment. The results obtained are shown in FIG. 7.

As seen from the results, the fluorescence intensity appeared relatively uniform across the all three experiments. Coupling of unprotected amino acids and Fmoc protected amino acids showed similar coupling efficiency, and coupling under basic conditions present in E2 and E3 did not affect the yield or the activation ester adversely.

Example 28: Effect of Photobase Generator Concentration on Coupling Yield

Concentration of photobase generator in a photoresist solution can be in the range of 1-30%, preferably in the range 5-15% by weight. The weight percentage of photobase generator used in the photoresist solution for peptide coupling was varied to measure the coupling yield. The amino acid Fmoc-Ala-OH was coupled to the wafer. Amino acid coupling was performed as explained above in Example 25 under different concentrations of photobase generator in photoresist solution. Unreacted carboxylic acids were capped using ethanolamine. Carboxylic acid groups from newly coupled alanine were activated as follows: 4% by weight EDC and 2% by weight NHS were dissolved in deionized water for 10 minutes and coated on the wafer. The wafer was then washed with deionized water for 3 minutes. Coupling yield was checked by coupling aminomethyl fluorescein to newly coupled alanine.

Figure 8:
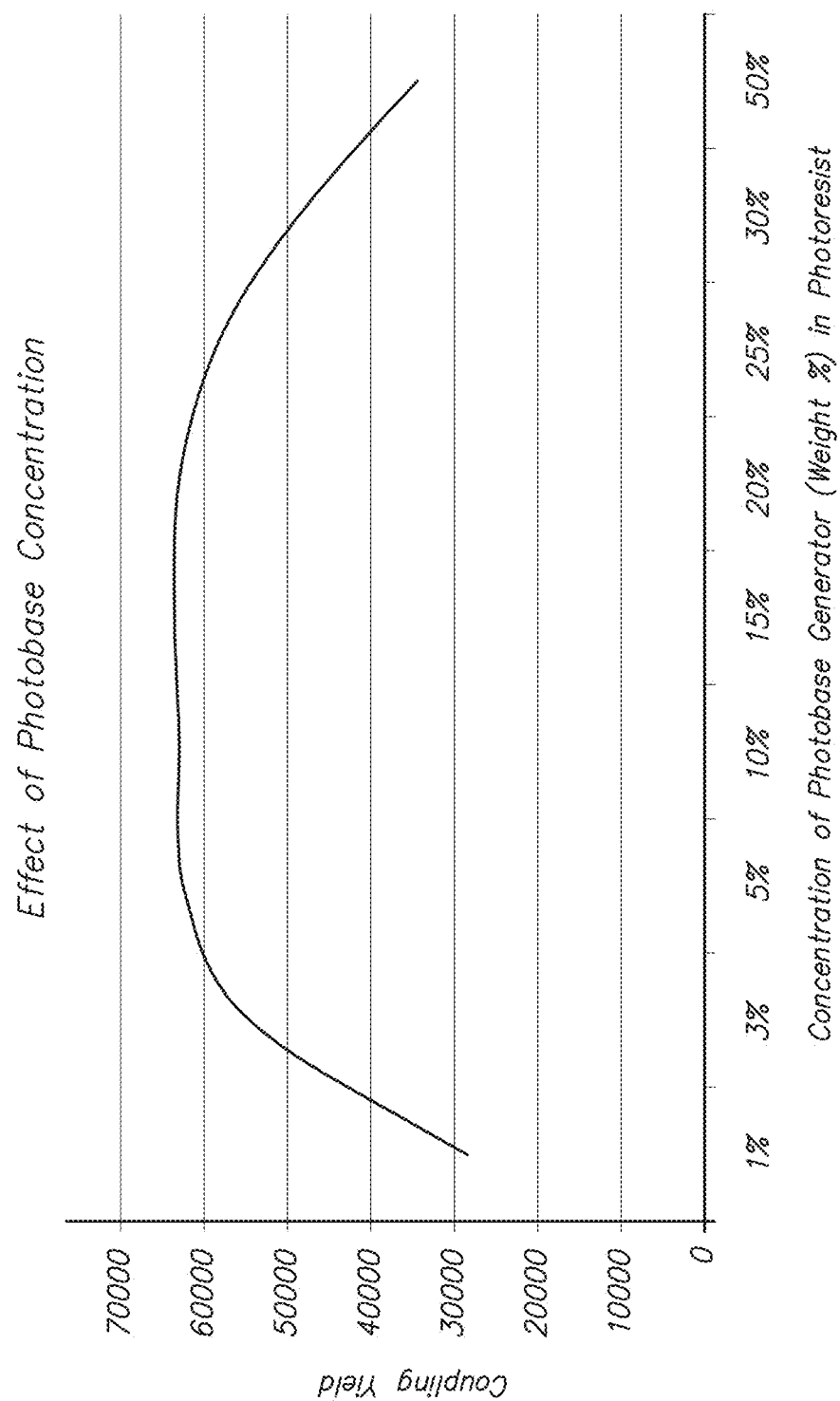
FIG. 8 shows the effect of photobase generator concentration in the photoresist on coupling efficiency of amino acids to the wafer as described herein.

As seen in FIG. 8, low concentration of photobase generator led to low deprotection and low coupling yield. Similarly high concentration of photobase generator led to good deprotection but poor coupling yield. Optimal concentrations of photobase generator were in the range of 5-25%.

Example 29: Coupling of Multiple Amino Acids after a Single Activation Step

Due to stability of the activated ester of the carboxylic acid for an extended period of time, 25 or more coupling cycles can be completed after a single activation step to form a complete layer of amino acids attached to an array. After addition of all amino acids, the wafer was capped, and the activation, coupling, and capping cycle was optionally repeated. The ability to perform multiple couplings at different times and locations on a wafer after a single activation step was validated by the following experiment:

The carboxylic acid surface on a wafer was activated by coating with an activation mixture of 4% by weight EDC and 2% by weight NHS dissolved in deionized water for 10 minutes. This was followed by washing the wafer with deionized water for 3 minutes.

Amino acid coupling was performed as follows: A photoresist coupling solution containing a polymer, amino acid with amino group protected with a light sensitive protecting group was spin-coated onto a wafer and baked. Next, the wafer was exposed to 248 nm radiation and then hard baked. Protecting group was removed from the amino acid only in the region, where the wafer was exposed to the 248 nm radiation. At this radiation-exposed region, activated carboxylic acid on the surface was coupled to the deprotected amine group of the amino acid. The wafer was then stripped with acetone and IPA. A photoresist coupling solution containing the next amino acid was then used and the same steps as described above were followed to couple this next amino acid to the previous amino acid.

For consecutive cycles of addition to the activated carboxylic acid, the capping step described earlier was not performed after each addition, but only after all additions were performed to complete amino acid layer. Amino acid coupling to the activated carboxylic acid was controlled by exposure to light. Coupling did not occur at non-exposed regions of the wafer.

Amino acid coupling yield was calculated for individual activation and capping and compared to multiple coupling of different amino acid to different sites in one activation cycle that was followed by capping. Coupling efficiency was determined by activating and coupling aminomethyl fluorescein to the wafer, where the unbound activated carboxylic acids were capped after all coupling steps were completed.

Figure 9:
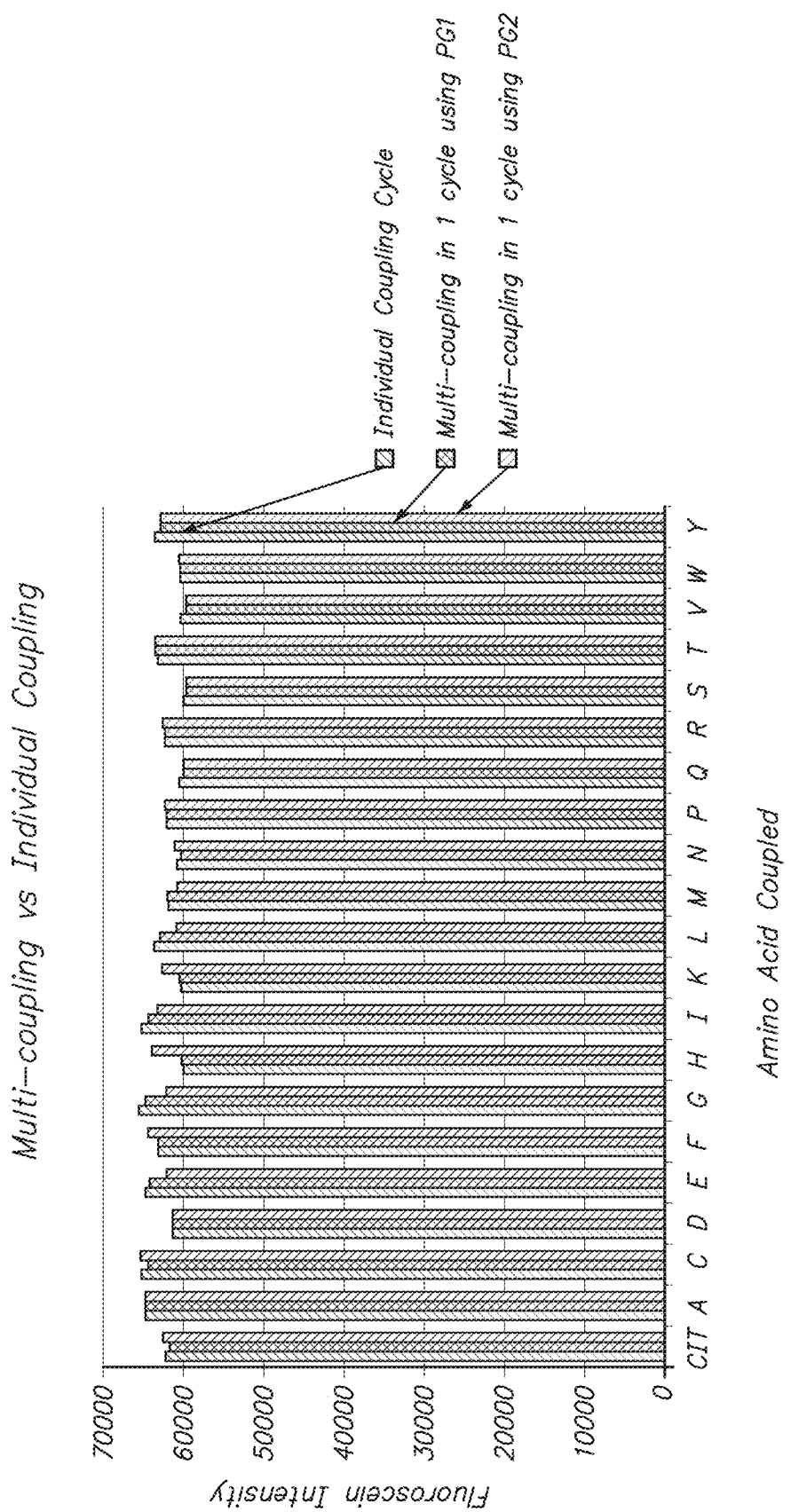
FIG. 9 shows coupling efficiency of individual coupling after carboxylic acid group activation versus multiple coupling after carboxylic acid group activation.

The fluorescent intensity measurements in FIG. 9 showed that individual coupling of each amino acid in 1 activation cycle was similar to multiple amino acids coupling in one activation cycle. This demonstrated that multi-coupling process by our method using a stable activated ester resulted in increased throughput compared to traditional peptide synthesis methodologies.

Example 30: Peptide Synthesis on a COOH Substrate Using Photolabile Group Protected Amino Acids Wafers with carboxylic acid surfaces were prepared as explained above using trimesic acid (Example 17) and activated with an activation mixture of 4% by weight EDC and 2% by weight NHS dissolved in deionized water for 10 minutes. This was followed by washing the carboxyl surface of each array with deionized water for 3 minutes. 2,2-Dimethyl-3,5-dimethyoxy-benzyloxy-benzocarbonate [DDZ] protected amino acids were obtained from Anaspec.

Amino Acid coupling was performed as follows: a photoresist coupling solution containing a copolymer (2.5% by weight of PMMA added to 1.5% by weight of Poly Ethylene Glycol) and 1% by weight of amino acid was spin-coated onto a wafer and baked. Next, the wafer was selectively exposed using a reticle to 248 nm radiation and then hard baked. DDZ-protected amino acids are deprotected only in the region where the wafer was exposed to 248 nm radiation. Deprotected amino acids were coupled to activated carboxylic acids attached to the wafer simultaneously during bake. Next, the wafer was stripped with acetone and IPA.

Ethanolamine was used for capping any activated COOH which were not coupled. This was done by spin coating a mixture of polymer, ethanolamine and deionized water onto the wafer and then baking the coated wafer. The wafer was then stripped by washing with deionized water. The same coupling and capping process was repeated for coupling each of the next amino acids. All individual amino acids were coupled to selected spots on a chip using a reticle. A range of radiation exposure energies were used to check coupling yield of each amino acid. This was done by coupling one acid at a time and finally activating and coupling aminomethyl fluorescein.

Example 31: Peptide Synthesis Using Fmoc Protected Amino Acids and a Photoacid Generator The sequence specificity and final yield of polypeptides on a wafer with a carboxylic acid surface was tested as follows:

Wafers with carboxylic acid surfaces were prepared as explained above using trimesic acid (Example 17). The carboxylic acid surface on a wafer was activated with an activation mixture of 4% by weight EDC and 2% by weight NHS dissolved in deionized water for 10 minutes. This was followed by washing the wafer with deionized water for 3 minutes.

Amino acid coupling was performed as follows: a photoresist coupling solution containing a copolymer (2.5% by weight of PMMA added to 1.5% by weight of Poly Ethylene Glycol), 1% by weight of Fmoc-protected amino acid, 5% of N-Boc-piperidine and 2.5% of a photoacid generator was spin-coated onto a wafer and baked. Next, the wafer was exposed to 248 nm radiation and then hard baked. The protecting group Boc was removed from piperidine only in the region where it is exposed. Piperidine removed Fmoc protection from the amino acid and the activated carboxylic acid on the surface was coupled to the amine group of the deprotected amino acid in the exposed regions. The wafer was then stripped with acetone and IPA. For multiple couplings, the cycle of activation and coupling described above is repeated with a new photoresist coupling solution containing the next amino acid.

The accuracy and efficiency of peptide synthesis using this method was measured by synthesizing the sequence RHSVV (Natural Sequence) and its mutated sequence GHSVV (Mutant Sequence) on a carboxylic acid wafer using the method described above.

After synthesis, the side chains of the amino acid were deprotected according to the following protocol: Trifluoroacetic Acid [TFA] was obtained from Sigma Aldrich. Pentamethylbenzene [PMB] and thioanisole was obtained from VWR. A solution of 33% by weight hydrogen bromide dissolved in acetic acid [HBr] was obtained from Sigma Aldrich.

The wafer was washed with TFA for 10 minutes. A solution comprising 0.4% by weight of PMB and 0.4% thioanisole was dissolved in TFA. After stirring thoroughly, 4% of HBr was added to the solution and the wafer was washed twice with this solution for 60 minutes each. The wafer was then washed with TFA for 5 minutes, IPA for 5 minutes, then DMF for 5 minutes. The wafer was then neutralized with 5% DIEA in DMF for 5 minutes, then washed with DMF for 5 minutes, and finally washed with IPA for 5 minutes.

The sequence specific binding of antibodies to the chip was performed as follows: The chips containing the synthesized natural and mutated sequences were washed with methanol for 5 minutes, then were washed with TBS Buffer for 5 minutes. The primary antibody solution containing PBST, 1% BSA and anti-p53 antibody was incubated on the surface of the wafer at 370 Celsius for 1 hour. The chip was washed with PBST for 5 minutes thrice. This was followed by incubating the chip with secondary antibody solution at 37° Celsius for 1 hour. The secondary antibody contained PBST, 1% BSA, and Goat anti-mouse IgG. The chip was washed with PBST for 5 minutes thrice. This was followed by washing with deionized water twice for 5 minutes each. The concentration of anti-p53 antibody was varied to validate the efficiency of coupling using the above process.

Figure 10:
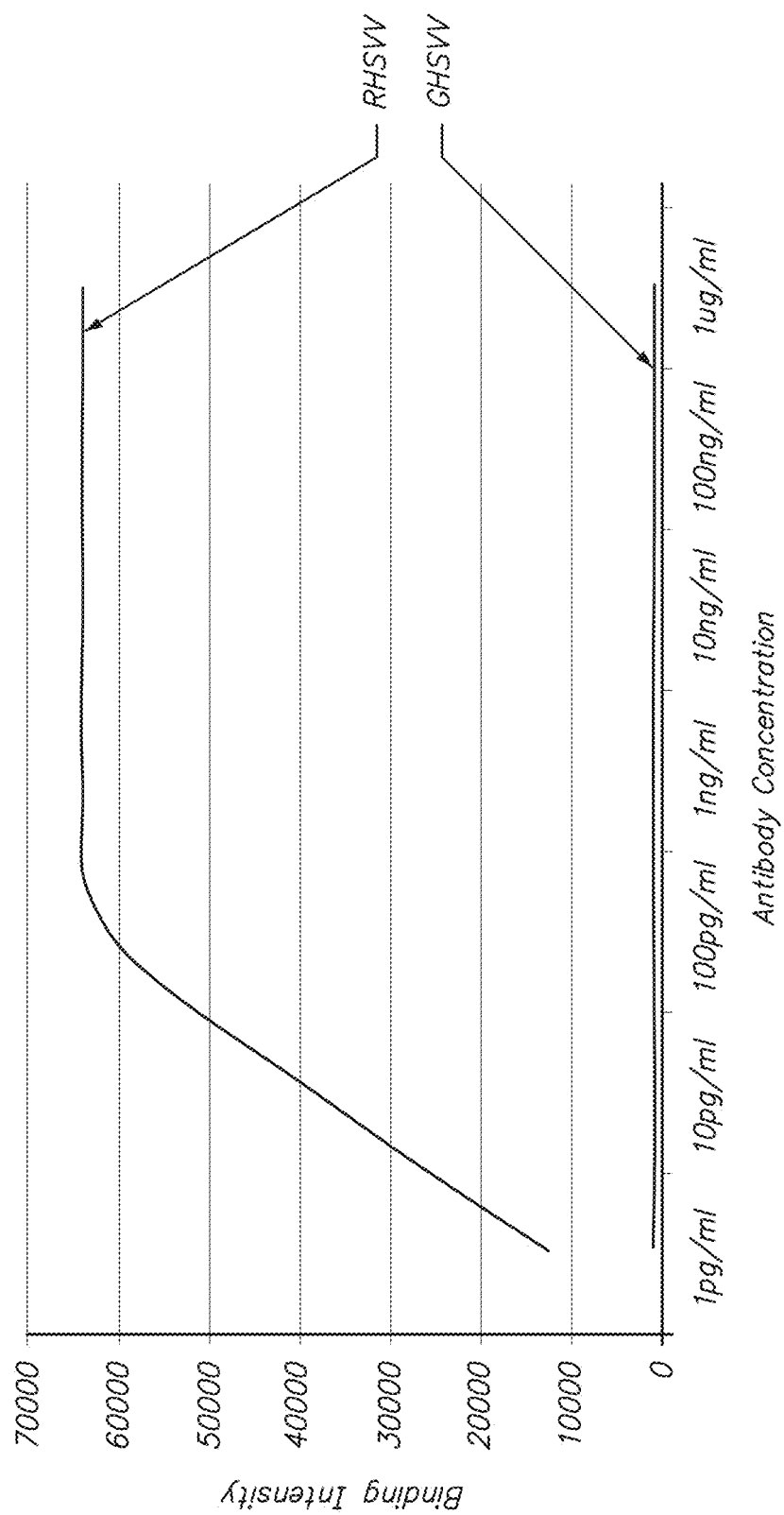
FIG. 10 shows binding of antibodies specific for RHSVV to a peptide array with RHSVV and GHSVV sequences synthesized by the methods described herein using a photoacid and a Boc-protected piperidine base in the photoresist composition.

The results as shown in FIG. 10 were consistent with the sequences grown using one-step deprotection and coupling validation process above. The binding of antibody concentration of 1 pg/mL to the correct sequence can be detected using this method. The binding intensity showed a log-linear increase with increasing antibody concentration over the lower end of the range tested and plateaus from 100 pg/mL to 1 µg/mL. This demonstrated the use photoacid generator instead of a photobase generator in a coupling solution using a protected piperidine base.

Example 32: Photoinduced Carbodiimides for Peptide and Protein Microarray Preparation This example did not rely on amino protecting groups and enabled carboxylic acids attached to the surface of an array to be selectively activated using photoinduced carbodiimide chemistry with selective photo irradiation through a photomask or automatic exposure method like a micromirror. The general activation chemistry for a tetrazole thione to form a carbodiimide is given in Scheme 2. After activation of the carboxylic acid groups by the photoactivated carbodiimide, amino acids or peptide chains having an unprotected amine group were added to the array and coupled to the activated carboxylic acid.

Process Flow for Preparing a Protein Array:

Wafers were prepared with COOH substrate as described in Example 13. One of three activation solutions was prepared as described below. 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, and 1,4-Bis (2,2-dimethyl-1,3-dioxolan-4-ylmethyl)-1,4-dihydro-5H-tetrazole-5-thione were obtained from Sigma Aldrich Inc. Polyvinyl pyrrollidone was obtained from Polysciences Inc.

Photoactivated Carboxylic Acid Activation Solution 1: 2.5% by weight of 4,5-dihydro-4-(hydroxymethyl)-1-phenyl-1H-tetrazole-5-thione was dissolved in 95% DI water along with 2.5% by weight of polyvinyl pyrrollidone and spun in a magnetic stirrer overnight to dissolve completely.

Photoactivated Carboxylic Acid Activation Solution 2: 2.5% by weight of 1-(3-(dimethylamino)propyl)-4-ethyl-1,4-dihydro-5H-tetrazole-5-thione was dissolved in 95% DI water along with 2.5% by weight of Polyvinyl pyrrollidone and spun in a magnetic stirrer overnight to dissolve completely.

Photoactivated Carboxylic Acid Activation Solution 3: 2.5% by weight of 1,4-Bis(2,2-dimethyl-1,3-dioxolan-4-ylmethyl)-1,4-dihydro-5H-tetrazole-5-thione was dissolved in 95% DI water along with 2.5% by weight of Polyvinyl pyrrollidone and spun in a magnetic stirrer overnight to dissolve completely.

Figure 11:
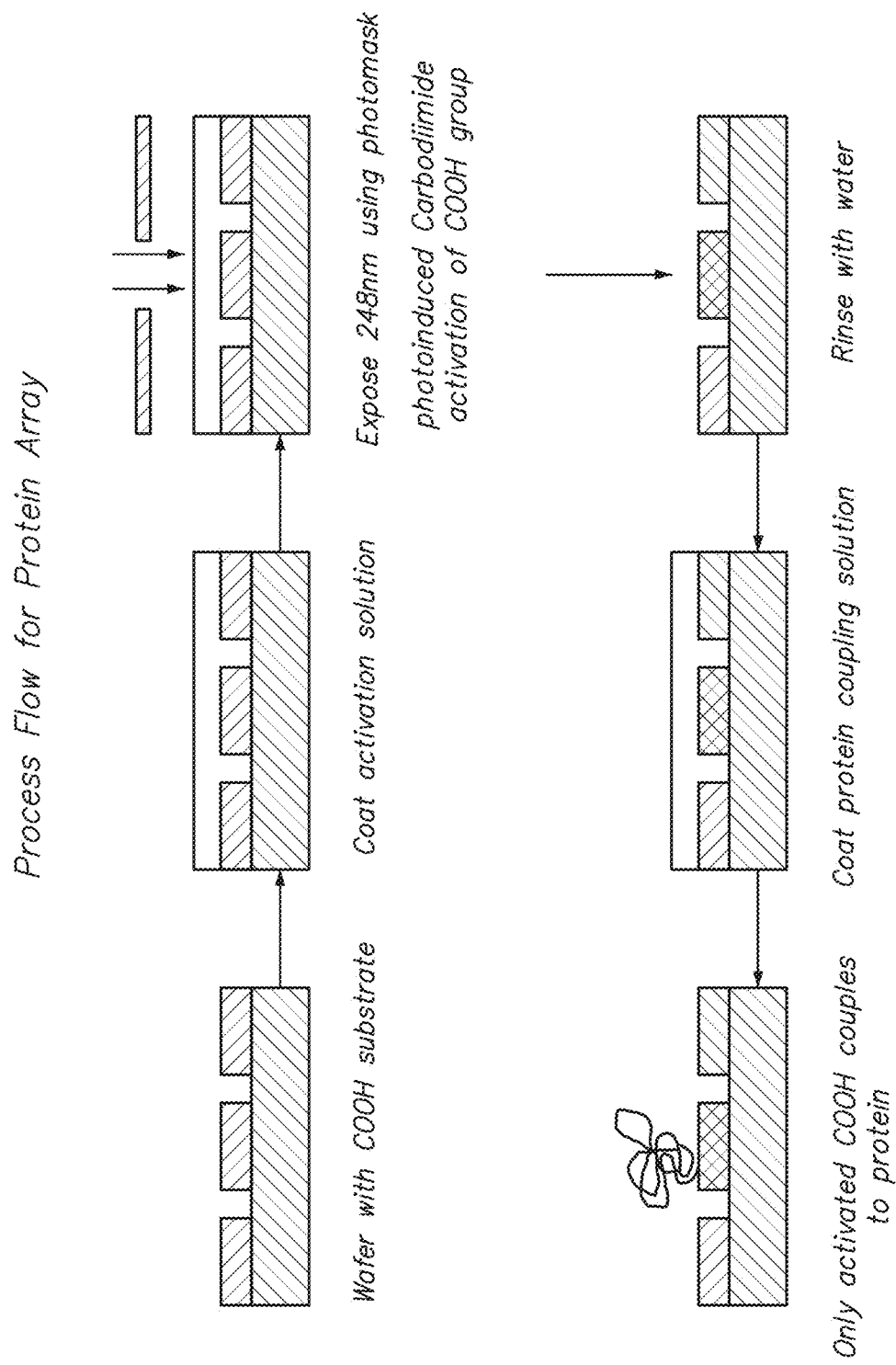
FIG. 11 shows a process flow for developing a protein array using photoactivated carbodiimide.

One of the above activation solutions comprising a thione was coated onto the wafer and baked at 850 Celsius for 90 seconds. The coat was exposed at 248 nm at 10-100 mJ/cm$^2$ using a photomask to choose regions to couple protein. In the exposed regions, the thione was converted into a carbodiimide (see, e.g., Scheme 2). Photoactivated conversion of 1,4-Bis(2,2-dimethyl-1,3-dioxolan-4-ylmethyl)-1,4-dihydro-5H-tetrazole-5-thione to 1,3-Bis(2,2-dimethyl-1,3-dioxolan-4-ylmethyl)-carbodiimide of activation solution 3 occurred at 248 nm and at 10-100 mJ/cm$^2$ (see, e.g., Scheme 3). The carbodiimide activated the carboxylic acid groups attached to the array by forming carbonyl groups ready to bind to an amino group. The activation solution was then washed from the chip, and the carboxylic acid groups remain activated for a certain amount of time. Protein coupling solution comprising 50 g/mL of TNF-alpha dissolved in 5% polyvinyl pyrrollidone in deionized water was prepared and was coated on the wafer at 2000 rpm. Then, the wafers were baked at 37° Celsius for 5 minutes to complete the TNF alpha coupling to the activated carboxylic acid comprising regions of the chip. The process above was repeated using IL-6 in place of TNF alpha and activating different regions on the chip. The complete process for site-specific activation of carboxylic acid groups via site-specific photoactivation of carbodiimide, and the attachment of protein to the activated sites, is depicted in FIG. 11.

To confirm attachment of TNF alpha and IL-6 to the correct locations on the chip, anti-TNF alpha and Anti IL-6 antibodies were added to the chip. All antibodies and buffer solutions were obtained from Life Technologies. The assay was performed as follows: anti-TNF alpha and Anti IL-6 antibodies were diluted 1:1000 in PBST buffer. Chips were washed in PBST buffer thrice for 5 minutes. The antibody solution was added to the chip and incubated for 1 hour at 370 Celsius in the dark. The chips were then washed with PBST buffer thrice for 5 min followed by deionized water thrice for 5 minutes. The chips were then scanned in a fluorescent scanner.

Figure 12:
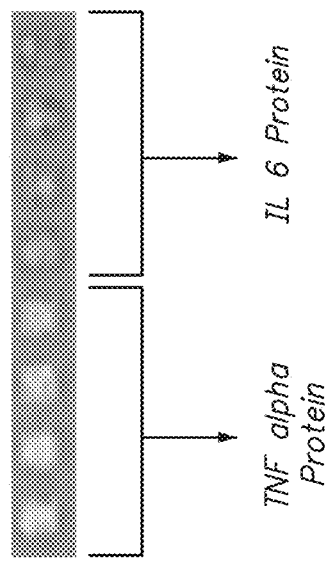
FIG. 12 shows the binding data for TNF alpha and IL-6 protein array formed via carbodiimide activation of carboxylic acid bound to the substrate.

Data for the two proteins on the array is shown in FIG. 12. Signal Intensities are represented in a scale from 0 to 65000. Binding to each protein was performed in quadruplicate (i.e., features 1-4). As shown in FIG. 12, TNF-alpha and IL-6 proteins each bound to their respective sites that were photoactivated by the method above before addition of the proteins. Therefore, photoactivated carbodiimide chemistry for attachment of polypeptides to activated carboxylic acid groups provided location-specific attachment of IL-6 and TNF-alpha to the array.

Example 33: Photoinduced Carbodiimides for Peptide Synthesis

In this example, method of C→N synthesis of peptides on a chip array using site-specific photoactivated carbodiimide activation of free carboxylic acid groups and attachment of unprotected amino acids to photoactivated carboxylic acid sites was performed. Wafers with COOH groups were prepared as explained in Example 13. The solutions used for the coupling reaction were as follows:

One of three activation solutions was prepared as described below. 4,5-dihydro-4-(hydroxymethyl)-1-phenyl-1H-tetrazole-5-thione, 1-(3-(dimethylamino)propyl)-4-ethyl-1,4-dihydro-5H-tetrazole-5-thione, and 1,4-Bis(2,2-dimethyl-1,3-dioxolan-4-ylmethyl)-1,4-dihydro-5H-tetrazole-5-thione were obtained from Sigma Aldrich Inc. Polyvinyl pyrrollidone was obtained from Polysciences Inc.

Activation Solution 1: 2.5% by weight of 4,5-dihydro-4-(hydroxymethyl)-1-phenyl-1H-tetrazole-5-thione was dissolved in 95% DI water along with 2.5% by weight of polyvinyl pyrrollidone and spun in a magnetic stirrer overnight to dissolve completely.

Activation Solution 2: 2.5% by weight of 1-(3-(dimethylamino)propyl)-4-ethyl-1,4-dihydro-5H-tetrazole-5-thione was dissolved in 95% DI water along with 2.5% by weight of polyvinyl pyrrollidone and spun in a magnetic stirrer overnight to dissolve completely.

Activation Solution 3: 2.5% by weight of 1,4-Bis(2,2-dimethyl-1,3-dioxolan-4-ylmethyl)-1,4-dihydro-5H-tetrazole-5-thione was dissolved in 95% DI water along with 2.5% by weight of polyvinyl pyrrollidone and spun in a magnetic stirrer overnight to dissolve completely.

Coupling Solutions were Prepared as Follows:

Coupling amino acid solution 1: A solution containing the amino acid coupling molecule alanine was prepared as follows: The polymer poly(methyl methacrylate) (i.e., PMMA) was dissolved in a 1:1 solvent solution of N-methylpyrrollidone and ethyl lactate. The final concentration of PMMA in solution was 1% by weight. Alanine was the coupling molecule and added to the solution for a final concentration of 2% by weight. Any other amino acid may be used in place of alanine for coupling of this other amino acid.

Coupling amino acid solution 2: Another solution containing the amino acid coupling molecule alanine was prepared as follows: The polymer PMMA was dissolved in the solvent N-methylpyrrollidone. The final concentration of PMMA in solution was 1% by weight. Alanine was the coupling molecule and added to the solution for a final concentration of 2% by weight. Any other amino acid may be used in place of alanine for coupling of this other amino acid.

Coupling amino acid solution 3: A solution containing the amino acid coupling molecule alanine was prepared as follows: The polymers PMMA and polyvinylpyrrolidone were each dissolved in the solvent N-methylpyrrollidone. The final concentration of PMMA and polyvinylpyrrolidone in solution were each 1% by weight. Alanine was the coupling molecule and added to the solution for a final concentration of 2% by weight. Any other amino acid may be used in place of alanine for coupling of this other amino acid.

Polymethyl methacrylate (PMMA) and poly vinyl pyrrollidone were obtained from Polysciences Inc.

Solid-Phase N→C Synthesis Methodology

One of the above activation solutions comprising a thione was coated onto the wafer and baked at 850 Celsius for 90 seconds. The coat was exposed at 248 nm at 10-100 mJ/cm$^2$ using a photomask to choose regions to couple the protein to. In the exposed regions, the thione was converted into a carbodiimide (see, e.g., Scheme 2). Photoactivated conversion of 1,4-Bis(2,2-dimethyl-1,3-dioxolan-4-ylmethyl)-1,4-dihydro-5H-tetrazole-5-thione to 1,3-Bis(2,2-dimethyl-1,3-dioxolan-4-ylmethyl)-carbodiimide of activation solution 3 occurred at 248 nm and at 10-100 mJ/cm$^2$ (see, e.g., Scheme 3). The carbodiimide activated the carboxylic acid groups attached to the array by forming carbonyl groups ready to bind to an amino group. The activation solution was then washed from the chip, and the carboxylic acid groups remained activated for at least 15 minutes.

One of the three amino acid coupling solutions described above was then layered on top of the wafer to allow reaction between the activated carboxylic acid groups and the amino acids. The amino acid was coupled to the activated carboxylic acid group. The solution was then washed, leaving the newly coupled amino acid bound to the activated carboxylic acid at site-specific location. The process was repeated to add desired amino acids at reticle-specified activated carboxylic acid locations to generate sequence-specific peptide chains at specific locations on the substrate.

What is claimed is:

1. A method of using a photobase generator for attaching a coupling molecule on a surface of an array, comprising:
   obtaining a substrate of an array comprising a plurality of carboxylic acid groups for linking to a coupling molecule;
   contacting the substrate with a carboxylic acid activating compound formulation comprising a carboxylic acid activating compound and a solvent;
   contacting the carboxylic acid activated substrate with a photoactive coupling formulation comprising a coupling molecule, a polymer and a solvent;
   selectively exposing the photoactive coupling formulation to light; and
   coupling the coupling molecule to at least one of the plurality of carboxylic acid groups at the selectively exposed area,
   wherein the photoactive coupling formulation further comprises:
   (a) a photobase generator comprising a compound of formula (II):

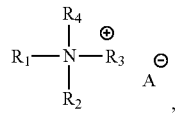
(II)

wherein

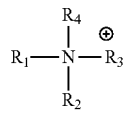

is a nitrogen-containing cation comprising

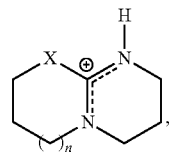

X is NH or $CH_2$, n is 0 to 3,

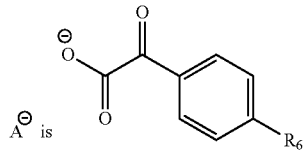

or tetraphenylborate, $R_6$ is hydrogen or $-NO_2$; and (b) the coupling molecule is an amino acid which has a protecting group attached to an amine group;

and wherein upon exposure of said photoactive coupling formulation to light, said protecting group is removed from said coupling molecule, and said unprotected coupling molecule binds to at least one of the plurality of carboxylic acid groups that are attached to the carboxylic acid activated substrate, and wherein said coupling step has a coupling efficiency of at least 98.5%; and repeating said contacting and coupling steps above to produce a desired polypeptide at said at least one carboxylic acid group, wherein said coupling step is performed multiple times at different selectively exposed areas on said substrate.

2. The method of claim 1, wherein said anion $A^\ominus$ is tetraphenylborate.

3. The method of claim 1, wherein said anion $A^\ominus$ is a phenylglyoxylate.

4. The method of claim 1, wherein said compound of formula (II) is selected from the group consisting of compounds of the formula:

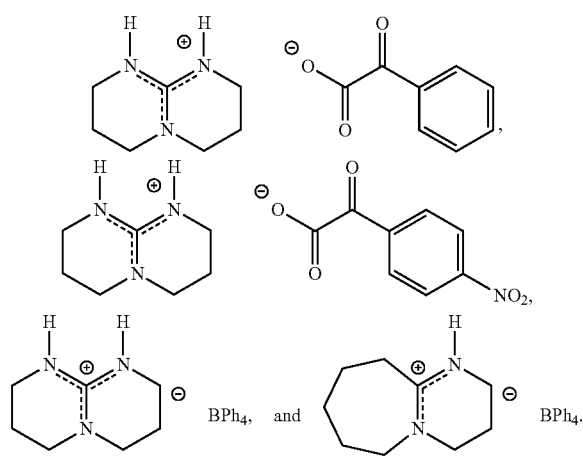

5. The method of claim 1, wherein said protecting group is base labile.

6. The method of claim 1, wherein said protecting group is Fmoc.

7. The method of any of claims 1-4, wherein said amino acid is present at 0.1M in said photobase composition.

8. The method of claim 1, wherein contacting the substrate with the carboxylic acid activating compound formulation comprises activating each of the plurality of carboxylic acid groups of the substrate.

9. The method of any of claims 1-4, wherein said polymer is polymethyl methacrylate.

10. The method of any of claims 1-4, wherein said substrate comprises a planar layer comprising a metal and having an upper surface and a lower surface; and a plurality of pillars operatively coupled to the layer in positionally-defined locations, wherein each pillar has a planar surface extended from the layer, wherein the distance between the surface of each pillar and the upper surface of the layer is between 1,000-5,000 angstroms, wherein the surface of each pillar is parallel to the upper surface of the layer, and wherein the plurality of pillars are present at a density of greater than 10,000/cm$^2$, and wherein the attachment site is coupled to the upper surface of the pillar.

* * * * *

SEQUENCE LISTING

<160> NUMBER OF SEQ ID NOS: 12

<210> SEQ ID NO 1
<211> LENGTH: 5
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg His Ser Val Val
1               5

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly His Ser Val Val
1               5

<210> SEQ ID NO 3
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ala Ala Ala Ala Ala Ala Ala Ala Ala Ala Ala Ala Ala Ala Ala Ala
1               5                   10                  15

Ala Ala Ala Ala
            20

<210> SEQ ID NO 4
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Leu Glu Arg
1

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Lys Leu Glu Arg Ser
1               5

<210> SEQ ID NO 6
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 6

Lys Leu Glu Arg Ser Thr
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Lys Leu Glu Arg Ser Thr Val
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Lys Leu Glu Arg Ser Thr Val Met
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Lys Leu Glu Arg Ser Thr Val Met Ile
1               5

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Lys Leu Glu Arg Ser Thr Val Met Ile Lys
1               5                   10

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 11

Lys Leu Glu Arg Ser Thr Val Met Ile Lys Gly
1               5                   10

<210> SEQ ID NO 12
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Lys Leu Glu Arg Ser Thr Val Met Ile Lys Gly Asp
1               5                   10
```